(12) United States Patent
Veves et al.

(10) Patent No.: US 10,130,661 B2
(45) Date of Patent: Nov. 20, 2018

(54) DEVICES FOR WOUND HEALING

(71) Applicants: President and Fellows of Harvard College, Cambridge, MA (US); Beth Israel Deaconess Medical Center, Inc., Boston, MA (US); Trustees of Tufts College, Medford, MA (US)

(72) Inventors: Aristidis Veves, Quincy, MA (US); David J. Mooney, Sudbury, MA (US); Jonathan Garlick, Brookline, MA (US)

(73) Assignees: President and Fellows of Harvard College, Cambridge, MA (US); Beth Israel Deaconess Medical Center, Inc., Boston, MA (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 14/709,258

(22) Filed: May 11, 2015

(65) Prior Publication Data

US 2017/0266236 A1  Sep. 21, 2017

Related U.S. Application Data

(60) Provisional application No. 61/991,201, filed on May 9, 2014.

(51) Int. Cl.

| | |
|---|---|
| *A61K 35/33* | (2015.01) |
| *A61L 27/22* | (2006.01) |
| *A61L 27/38* | (2006.01) |
| *A61L 27/52* | (2006.01) |
| *A61L 27/54* | (2006.01) |
| *A61L 27/56* | (2006.01) |
| *A61L 27/20* | (2006.01) |
| *A61K 38/18* | (2006.01) |
| *C12N 5/00* | (2006.01) |

(52) U.S. Cl.
CPC .............. *A61K 35/33* (2013.01); *A61K 38/18* (2013.01); *A61L 27/20* (2013.01); *A61L 27/3804* (2013.01); *A61L 27/52* (2013.01); *A61L 27/54* (2013.01); *A61L 27/56* (2013.01); *C12N 5/00* (2013.01); *A61L 2300/414* (2013.01)

(58) Field of Classification Search
None
See application file for complete search history.

(56) References Cited

PUBLICATIONS

Vats, et al. (2013) "Dynamic Manipulation of Hydrogels to Control Cell Behavior: A Review", Tissue Engineering. Part B, Reviews, 19(6): 455-69.*
Fu, et al. (2002) "Comparative study of fibronectin gene expression in tissues from hypertrophic scars and diabetic foot ulcers", Chinese Medical Science Journal, 17(2): 90-94.*
Gerami-Naini et al., Generation of Induced Pluripotent Stem Cells from Diabetic Foot Ulcer Fibroblasts Using a Nonintegrative Sendai Virus. Cell Reprogram. Aug. 2016;18(4):214-23.
Maione et al., Altered ECM deposition by diabetic foot ulcer-derived fibroblasts implicates fibronectin in chronic wound repair. Wound Repair Regen. Jul. 2016;24(4):630-43.
Maione et al., Three-dimensional human tissue models that incorporate diabetic foot ulcer-derived fibroblasts mimic in vivo features of chronic wounds. Tissue Eng Part C Methods. May 2015;21(5):499-508.
Park et al., Genome-wide DNA methylation analysis identifies a metabolic memory profile in patient-derived diabetic foot ulcer fibroblasts. Epigenetics. Oct. 2014;9(10):1339-49.

* cited by examiner

*Primary Examiner* — Robert M Kelly
(74) *Attorney, Agent, or Firm* — McCarter & English, LLP; Maria Laccotripe Zacharakis; Wei Song

(57) ABSTRACT

The present invention provides devices and methods for improving wound healing, in particular, in diabetic subjects.

19 Claims, 2 Drawing Sheets

Specification includes a Sequence Listing.

DEVICES FOR WOUND HEALING

RELATED APPLICATIONS

This application claims the benefit of priority under 35 U.S.C. § 119(e) to U.S. Provisional Application No. 61/991,201, filed May 9, 2014, which is incorporated herein by reference in its entirety.

GOVERNMENT SUPPORT

The invention was supported, in whole, or in part, by NIH grant numbers 1 R24 DK091210-01A1, RO1 DE017413-01A1, and RO1 DK98055-06A1. The Government has certain rights in the invention.

FIELD OF THE INVENTION

The present invention relates to hydrogels for cell therapy and their use in wound healing.

SEQUENCE LISTING

The instant application contains a Sequence Listing which has been submitted electronically in ASCII format and is hereby incorporated by reference in its entirety. Said ASCII copy, created on Dec. 5, 2016, is named 117823-09102_SL.txt and is 57,081 bytes in size.

BACKGROUND OF THE INVENTION

Diabetes is a chronic disease in which the body cannot properly regulate glucose metabolism. An estimated 9% of the U.S. population has been diagnosed with diabetes. Because of complications associated with diabetes, such as neuropathy, a weakened immune system, and narrowed arteries, wounds in diabetic subjects are particularly difficult to heal—they are prone to infection and either do not heal or heal slowly. Thus, there is a need for compositions that are effective in healing wounds such as those from diabetic subjects.

Cell transplantation has been used in regenerative medicine for musculoskeletal disorders as well as degenerative conditions such as diabetes with limited success. Limitations of earlier approaches include loss of cell viability and function following transplantation.

Currently available products for the management of diabetic foot ulceration include the growth factor, becaplermin (REGRANEX™), and bioengineered skins, APLIGRAF™ and DERMAGRAFT™. However, efficiency of these products to heal ulcers has been limited. Thus, there is a need for a more efficient therapy that is also easier and less expensive to produce. This invention addresses these needs.

SUMMARY OF THE INVENTION

The invention overcomes the drawbacks of earlier products described above and features a device comprising a structural composition (e.g., a hydrogel scaffold or cell delivery vehicle) and a population of fibroblasts, where the hydrogel comprises pores, and where the population of fibroblasts is seeded into or onto the hydrogel, e.g., an alginate hydrogel. Preferably, the fibroblasts are derived from or isolated from a subject diagnosed with or suffering from diabetes. For example, the fibroblasts are derived from or isolated from an ulcer, e.g., a foot ulcer, on a subject diagnosed with or suffering from diabetes. As described herein, hydrogels comprising diabetic ulcer fibroblast cells from diabetic wounds, e.g., foot ulcers, promote diabetic wound healing better than nondiabetic, nonulcerated foot-derived fibroblasts.

The device contains nanopores, micropores, macropores, or a combination thereof. The size of the pores permits cell migration or movement (e.g., fibroblast migration into and/or egress out of the delivery vehicle) through the pores. For example, the composition comprises pores that are characterized by a diameter of 20-500 µm (e.g., 50-500 µm, or 20-300 µm).

The population of fibroblasts comprises a fibroblast that is derived from or isolated from a subject diagnosed as suffering from diabetes. In some embodiments, the population of fibroblasts comprises a fibroblast that is derived from or isolated from a subject having a wound, e.g., at or near the site of a skin ulcer. For example, a site near a skin ulcer is about 0.1 mm, 0.5 mm, 1 mm, 2.5 mm, 5 mm, 10 mm, 15 mm, 20 mm, or 40 mm away from a perimeter or margin of the ulcer. For example, the wound is located in an extremity (e.g., an arm, hand, leg, foot, toe, or finger), and the cells are explanted or obtained directly from the ulcerated skin or lesion itself or about 0.1 mm, 0.5 mm, 1 mm, 2.5 mm, 5 mm, 10 mm, 15 mm, 20 mm, or 40 mm from a perimeter or margin of the ulcer. In some cases, the wound is a diabetic wound. Optionally, the diabetic wound is characterized by inflammation (e.g., presence of pro-inflammatory immune cells and pro-inflammatory cytokines). Exemplary pro-inflammatory immune cells include macrophages, dendritic cells, T cells (helper T cells, CD8+ cytotoxic T cells), and natural killer cells. Exemplary pro-inflammatory cytokines include tumor necrosis factor-α(TNFα), IL-1, IL-2, and interferon-γ (IFN-γ). In some cases, the wound is an ulcer (e.g., a foot ulcer).

The subject in need of a device of the invention has been diagnosed with diabetes and suffers from a wound, e.g., a dermal wound.

In some cases, the fibroblast of the device is derived from or isolated from the site of the wound or a site adjacent to the wound. In some examples, fibroblasts derived from or isolated from diabetic wounds have an altered production (e.g., expression level and/or expression pattern) of proteins that are important for making a well-structured wound bed. In some cases, fibroblasts derived from diabetic wounds have an absence of stimulatory factors that are linked to the non-healing features of these wounds.

At least 5% (e.g., at least 5%, 10%, 20%, 30%, 40%, 50%, 60%, 70%, 80%, 90%, 95%, 98%, or more) of the fibroblasts in the population are derived from or isolated from the site of a wound or a site adjacent to the wound. For example, the population of fibroblasts comprises a fibroblast that is derived from a portion of the skin of the subject. In some cases, the population of fibroblasts is derived from or isolated from a foot ulcer from a subject suffering from diabetes.

A diabetic ulcer fibroblast is identified by differential expression of biomarkers or differential cell signaling responses compared to normal fibroblasts or fibroblasts taken or derived from non-ulcerous tissue. For example, the population of fibroblasts derived from diabetic foot ulcers expresses fibronectin at a level at least 1.1 fold more than nondiabetic, nonulcerated foot-derived fibroblasts, e.g., at least 1.2 fold more, at least 1.3 fold more, at least 1.4 fold more, at least 1.5 fold more, at least 1.6 fold more, at least 1.7 fold more, at least 1.8 fold more, at least 1.9 fold more, at least 2 fold more, at least 3 fold more, at least 4 fold more, at least 5 fold more, at least 6 fold more, at least 7 fold more, at least 8 fold more, at least 9 fold more, at least 10 fold more, at least 11 fold more, at least 12 fold more, at least 13 fold more, at least 14 fold more, at least 15 fold more, at least 20 fold more, at least 30 fold more, at least 40 fold more, at least 50 fold more, at least 60 fold more, at least 70 fold more, at least 80 fold more, at least 90 fold more, or at least 100 fold more.

For example, the subject is a mammal, e.g., a human, dog, cat, pig, or horse. Preferably, the subject is a human.

In some cases, the population of fibroblasts comprises fibroblasts that have been cultured and optionally expanded in vitro.

In some embodiments, the population of fibroblasts includes a fibroblast comprising metabolic memory. For example, the metabolic memory is associated with an epigenetic alteration or is due to an epigenetic alteration compared to a fibroblast derived from a subject i) not suffering from diabetes, ii) not having a wound, or both i) and ii).

In some embodiments, the population of fibroblasts includes a fibroblast comprising an epigenetic alteration compared to a fibroblast derived from a subject i) not suffering from diabetes, ii) not having a wound, or both i) and ii). In some examples, fibroblasts of diabetic patients, in particular, in fibroblasts from foot ulcers of diabetic patients, comprise epigenetic changes, e.g., methylation changes.

Optionally, the population of fibroblasts comprises a genetically modified fibroblast. For example, the fibroblasts are modified to overexpress growth factors or cytokines that enhance wound healing (e.g., angiogenic factors such as vascular endothelial growth factor (VEGF), placental growth factor (PlGF), fibroblast growth factor (FGF)), increase epithelial or fibroblast migration (e.g., hepatocyte growth factor (HGF)), modify the inflammatory/immune response (e.g., transforming growth factor beta (TGF-β), interleukin-10 (IL-10)), or inhibit scarring.

Some devices of the invention further comprise a bioactive composition. Exemplary bioactive compositions include cell growth and/or cell differentiation factors. For example, a bioactive composition includes a growth factor, morphogen, differentiation factor, and/or chemoattractant. For example, the device includes vascular endothelial growth factor (VEGF), hepatocyte growth factor (HGF), or fibroblast growth factor 2 (FGF2) or a combination thereof. Other bioactive compositions include hormones, neurotransmitters, neurotransmitter or growth factor receptors, interferons, interleukins, chemokines, MMP-sensitive substrate, cytokines, colony stimulating factors and phosphatase inhibitors. Growth factors used to promote angiogenesis, wound healing, and/or tissue regeneration can be included in the device.

In some embodiments, the device is implantable or injectable into a subject.

In addition, the invention features a method of treating a wound in a patient in need thereof comprising administering a device described herein. For example, the method includes the step of providing a diabetic ulcer fibroblast, seeding a hydrogel such as an alginate hydrogel with the fibroblast and administering the cell-seeded hydrogel to a diabetic skin wound. For example, the cell-seeded hydrogel is administered to or near the wound, e.g., skin ulcer. A site near a skin ulcer is about 0.1 mm, 0.5 mm, 1 mm, 2.5 mm, 5 mm, 10 mm, 15 mm, 20 mm, or 40 mm away from a perimeter or margin of the ulcer. For example, the wound is located in an extremity (e.g., an arm, hand, leg, foot, toe, or finger), and the cell seeded hydrogel is administered directly to the ulcerated skin or lesion itself or about 0.1 mm, 0.5 mm, 1 mm, 2.5 mm, 5 mm, 10 mm, 15 mm, 20 mm, or 40 mm from a perimeter or margin of the ulcer.

For example, the patient suffers from diabetes. For example, the patient suffers from a wound that is resistant to healing. In some cases, the wound is located in an extremity of the patient (e.g., an arm, leg, foot, hand, toe, or finger). For example, the patient suffers from an ulcer, e.g., in an extremity such as a foot. Exemplary ulcers have a diameter of at least about 25 mm, 50 mm, 1 cm, 2 cm, 3 cm, 4 cm, 5 cm, 6 cm, 7 cm, 8 cm, 9 cm, 10 cm, or greater.

Routes of administration of the device include injection or implantation. Alternate routes include topical application, e.g., applying the device in the form of a coating, covering, or bandage contacting a wound. Other routes of administration comprise spraying the device, e.g., hydrogel, onto a wound, e.g., as a fluid or aerosol, followed by solidification of the device, e.g., hydrogel, once in contact with the wound.

The dermal diabetic ulcer-associated fibroblasts are purified, e.g., by separating the fibroblasts from other cellular or non-cellular material. The fibroblasts can be purified or in a heterologous mixture of cells taken from or adjacent to a diabetic wound. In some embodiments, the population of fibroblasts comprises an autologous fibroblast (e.g., at least 10%, 20%, 30%, 40%, 50%, 60%, 70%, 80%, 90%, 95%, 98%, or more autologous fibroblasts). Alternatively or in addition, the population of fibroblasts comprises an allogeneic or xenogeneic fibroblast. For example, the population of fibroblasts comprises at least 10% (e.g., at least 20%, 30%, 40%, 50%, 60%, 70%, 80%, 90%, 95%, 98%, or more) allogeneic fibroblasts. For example, the population of fibroblasts comprises at least 10% (e.g., at least 20%, 30%, 40%, 50%, 60%, 70%, 80%, 90%, 95%, 98%, or more) xenogeneic fibroblasts.

The fibroblasts preferably elicit a minimal adverse host response (e.g., minimal harmful inflammation and/or minimal host immune rejection of the transplanted fibroblasts).

The devices of the invention enhance the viability of passenger cells (e.g., fibroblasts) and induce their outward migration to populate injured or defective bodily tissues enhance the success of tissue regeneration, e.g., the regeneration of muscle tissue or other tissues, as well as angiogenesis. Such a device that controls cell function and/or behavior, e.g., locomotion, contains a scaffold composition and one or more bioactive compositions. The bioactive composition is incorporated into or coated onto the scaffold composition. The scaffold composition and/or bioactive composition temporally and spatially (directionally) controls egress of a resident cell (e.g., fibroblast) or progeny thereof. At the end of a treatment period, the device is has release a substantial number of the passenger cells that were originally used to seed the device, e.g., there is a net efflux of passenger cells. For example, the device releases 10% or more (e.g., 10%, 20%, 30%, 40%, 50%, 60%, 70%, 80%, 90%, 100%, 200%, 300%, 400%, or more) of the seeded passenger cells by the end of a treatment period compared to at the commencement of treatment. In another example, the device contains 50% or less (e.g., 50%, 40%, 30%, 25%, 20%, 15%, 10%, 5%, 2.5%, 1%, or less) of the seeded passenger cells at the end of a treatment period compared to at the commencement of treatment. In some cases, a greater number of cells can be released than originally loaded if the cells proliferate after being placed in contact with the scaffold.

In some cases, the devices mediate modification and release of host cells from the material in vivo, thereby improving the function of cells that have resided in the scaffold composition. For example, the scaffold composition temporally and spatially (directionally) controls fibroblast migration. For example, the scaffold composition mediates release of fibroblasts from the material in vivo.

This device includes a scaffold composition which incorporates or is coated with a bioactive composition; the device regulates the egress of resident cells. Egress is regulated spatially and temporally. Depending on the application for which the device is designed, the device regulates egress through the physical or chemical characteristics of the scaffold composition itself. For example, the scaffold composition is differentially permeable, allowing cell egress only in certain physical areas of the scaffold composition. The permeability of the scaffold composition is regulated, for example, by selecting or engineering a material for greater or smaller pore size, density, polymer cross-linking, stiffness, toughness, ductility, or viscoelascticity. The scaffold composition contains physical channels or paths through which cells can move more easily towards a targeted area of egress of the device or of a compartment within the device. The scaffold composition is optionally organized into compartments or layers, each with a different permeability, so that the time required for a cell to move through the device is precisely and predictably controlled. Migration is also regulated by the degradation, de- or re-hydration, oxygenation, chemical or pH alteration, or ongoing self-assembly of the scaffold composition. These processes are driven by diffusion or cell-secretion of enzymes or other reactive chemicals.

Alternatively or in addition, egress is regulated by a bioactive composition. By varying the concentration of growth factors, homing/migration factors, morphogens, differentiation factors, oligonucleotides, hormones, neurotransmitters, neurotransmitter or growth factor receptors, interferons, interleukins, chemokines, cytokines, colony stimulating factors, chemotactic factors, extracellular matrix components, adhesion molecules and other bioactive compounds in different areas of the device. The device controls and directs the migration of cells through its structure. Chemical affinities are used to channel cells towards a specific area of egress. For example, adhesion molecules are used to attract or retard the migration of cells. By varying the density and mixture of those bioactive substances, the device controls the timing of the migration and egress. The density and mixture of these bioactive substances is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/excretion of compositions by resident support cells. The physical or chemical structure of the scaffold composition also regulates the diffusion of bioactive agents through the device.

The bioactive composition includes one or more compounds that regulate cell function and/or behavior. For example, the bioactive composition includes cell adhesion ligands (e.g., RGD-containing peptides) and growth factors (e.g., FGF and HGF). The bioactive composition is covalently linked to the scaffold composition or non-covalently associated with the scaffold. For example, the bioactive composition is an extracellular matrix (ECM) component that is chemically crosslinked to the scaffold composition. Regardless of the tissue of origin, ECM components generally include three general classes of macromolecules: collagens, proteoglycans/glycosaminoglycans (PG/GAG), and glycoproteins, e.g., fibronectin (FN), laminin, and thrombospondin. ECM components associate with molecules on the cell surface and mediate adhesion and/or motility. Preferably, the ECM component associated with the scaffold composition is a proteoglycan attachment peptide or cyclic peptide containing the amino acid sequence arginine-glycine-aspartic acid (RGD). Proteoglycan attachment peptides are selected from the group consisting of G$_4$RGDSP (SEQ ID NO: 1), XBBXBX (SEQ ID NO: 2), PRRARV (SEQ ID NO: 3), YEKPGSPPREVVPRPRPGV (SEQ ID NO:4), RPSLAKKQRFRHRNRKGYR-SQRGHSRGR (SEQ ID NO: 5), and RIQNLLKITNLRIK-FVK (SEQ ID NO: 6), and cell attachment peptides are selected from the group consisting of RGD, RGDS (SEQ ID NO: 7), LDV, REDV (SEQ ID NO: 8), RGDV (SEQ ID NO: 9), LRGDN (SEQ ID NO: 10), IKVAV (SEQ ID NO: 11), YIGSR (SEQ ID NO: 12), PDSGR (SEQ ID NO: 13), RNIAEIIKDA (SEQ ID NO: 14), RGDT (SEQ ID NO: 15), DGEA (SEQ ID NO: 16), and VTXG (SEQ ID NO: 17).

Components of the ECM, e.g., FN, laminin, and collagen, interact with the cell surface via the integrin family of receptors, a group of divalent cation-dependent cell surface glycoproteins that mediate cellular recognition and adhesion to components of the ECM and to other cells. Ligands recognized by integrins typically contain an RGD amino acid sequence that is expressed in many ECM proteins. Exemplary molecules that mediate cell adhesion and/or movement include FN, laminin, collagen, thrombospondin 1, vitronectin, elastin, tenascin, aggrecan, agrin, bone sialoprotein, cartilage matrix protein, fibronogen, fibrin, fibulin, mucins, entactin, osteopontin, plasminogen, restrictin, serglycin, SPARC/osteonectin, versican, von Willebrand Factor, polysaccharide heparin sulfate, cell adhesion molecules including connexins, selectinsinclude collagen, RGD (Arg-Gly-Asp) and YIGSR (Tyr-Ile-Gly-Ser-Arg) (SEQ ID NO: j peptides, glycosaminoglycans (GAGs), hyaluronic acid (HA), integrins, selectins, cadherins and members of the immunoglobulin superfamily. Carbohydrate ligands of the ECM include the polysaccharides hyaluronic acid, and chondroitin-6-sulfate.

Signal transduction events that participate in the process of cell motility are initiated in response to cell growth and/or cell differentiation factors. Thus, the device optionally contains a second bioactive composition that is a growth factor, morphogen, differentiation factor, or chemoattractant. For example, the device includes vascular endothelial growth factor (VEGF), hepatocyte growth factor (HGF), or fibroblast growth factor 2 (FGF2) or a combination thereof. Other factors include hormones, neurotransmitters, neurotransmitter or growth factor receptors, interferons, interleukins, chemokines, MMP-sensitive substrate, cytokines, colony stimulating factors. Growth factors used to promote angiogenesis, bone regeneration, wound healing, and other aspects of tissue regeneration are listed herein and are used alone or in combination to induce colonization or regeneration of bodily tissues by cells that have migrated out of an implanted device.

The scaffold composition is biocompatible. The composition is bio-degradable/erodable or resistant to breakdown in the body. Relatively permanent (degradation resistant) scaffold compositions include metals and some polymers such as silk. Preferably, the scaffold composition degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

In one example, cells mediate degradation of the scaffold matrix, i.e., the scaffold composition is enzymatically digested by a composition elicited by a resident cell, and the egress of the cell is dependent upon the rate of enzymatic digestion of the scaffold composition. In this case, polymer main chains or cross-links contain compositions, e.g., oligopeptides, that are substrates for collagenase or plasmin, or other enzymes produced by within or adjacent to the scaffold composition.

Exemplary scaffold compositions include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly(uronic acids), poly(vinylpyrrolidone) and copolymers or graft copolymers of any of the above. One preferred scaffold composition includes an RGD-modified alginate.

Porosity of the scaffold composition influences migration of the cells through the device and egress of the cells from the device. Pores are nanoporous, microporous, or macroporous. In some cases, the pores are a combination of these sizes. For example, the pores of the scaffold composition are large enough for a cell, e.g., fibroblast, to migrate through. For example, the diameter of nanopores are less than about 10 nm; micropore are in the range of about 100 nm-20 µm in diameter; and, macropores are greater than about 20 µm (preferably greater than about 100 µm and even more preferably greater than about 400 µm). In one example, the scaffold composition is macroporous with aligned pores of about 400-500 µm in diameter.

The devices are manufactured in their entirety in the absence of cells or can be assembled around or in contact with cells (the material is gelled or assembled around cells in vitro or in vivo in the presence of cells and tissues) and then contacted with cells to produce a cell-seeded structure. Alternatively, the device is manufactured in two or more (3, 4, 5, 6, . . . 10 or more) stages in which one layer or compartment is made and seeded with cells followed by the construction of a second, third, fourth or more layers, which are in turn seeded with cells in sequence. Each layer or compartment is identical to the others or distinguished from one another by the number, genotype, or phenotype of the seed cell population as well as distinct chemical, physical and biological properties. Prior to implantation, the device is contacted with purified populations cells or characterized mixtures of cells as described above. Preferably, the cells are human; however, the system is adaptable to other eukaryotic animal cells, e.g., canine, feline, equine, bovine, and porcine as well as prokaryotic cells such as bacterial cells.

A method of making a device is carried out by providing a scaffold composition and covalently linking or noncovalently associating the scaffold composition with a first bioactive composition. The first bioactive composition preferably contains a cell adhesion ligand. The scaffold composition is also contacted with a second bioactive composition. The second bioactive composition is preferably non-covalently associated with the scaffold composition to yield a doped scaffold, i.e., a scaffold composition that includes one or more bioactive substances. The contacting steps are optionally repeated to yield a plurality of doped scaffolds, e.g., each of the contacting steps is characterized by a different amount of the second bioactive composition to yield a gradient of the second bioactive composition in the device. Rather than altering the amount of composition, subsequent contacting steps involve a different bioactive composition, i.e., a third, fourth, fifth, sixth . . . , composition or mixture of compositions, that is distinguished from the prior compositions or mixtures of prior doping steps by the structure or chemical formula of the factor(s). The method optionally involves adhering individual niches, layers, or components to one another and/or insertion of semi-permeable, permeable, or nonpermeable membranes within or at one or more boundaries of the device to further control/regulate locomotion of cells or bioactive compositions. As described above, the device is seeded with cells after completion of the construction of the device or in an iterative manner throughout the construction of each component.

Therapeutic applications of the device include tissue generation, regeneration/repair, as well as augmentation of function of a mammalian bodily tissue in and around a wound. For example, the method includes the steps of providing a device that includes scaffold composition with a bioactive composition incorporated therein or thereon and a mammalian cell (e.g., fibroblast) bound to the device. A mammalian tissue is contacted with the device. The scaffold composition temporally controls egress of the cell and the bioactive composition spatially or directionally regulates egress of the cell. In another example, the device that is provided contains a scaffold composition with a bioactive composition incorporated therein or thereon and a mammalian cell immobilized within the device. In the latter case, the cell remains immobilized within the device, and the scaffold composition temporally controls egress of a progeny cell of the immobilized cell and the bioactive composition spatially regulates egress of the progeny cells.

In some cases, the cells (e.g., fibroblasts) remain resident in the device for a period of time, e.g., minutes; 0.2. 0.5, 1, 2, 4, 6, 12, 24 hours; 2, 4, 6, days; weeks (1-4), months (2, 4, 6, 8, 10, 12) or years, during which the cells are exposed to structural elements and bioactive compositions that lead to proliferation of the cells, and/or a change in the activity or level of activity of the cells. The cells are contacted with or exposed to a deployment signal that induces egress of the optionally altered (re-educated or reprogrammed) cells and the cells migrate out of the device and into surrounding tissues or remote target locations.

The deployment signal is a composition such as protein, peptide, or nucleic acid. In some cases, the deployment signal is a nucleic acid molecule, e.g., a plasmid containing sequence encoding a protein that induces migration of the cell out of the device and into surrounding tissues. The deployment signal occurs when the cell encounters the plasmid in the device, the DNA becomes internalized in the cell (i.e., the cell is transfected), and the cell manufactures the gene product encoded by the DNA. In some cases, the molecule that signals deployment is an element of the device and is released from the device in delayed manner (e.g., temporally or spatially) relative to exposure of the cell to the recruitment composition.

Cells (e.g., fibroblasts) contained in the devices described herein promote regeneration of a tissue or organ (e.g., a wound) immediately adjacent to the material, or at some distant site.

In some cases, the invention described herein provides an inverse opal hydrogel scaffold device comprising a polymer matrix and a sacrificial porogen in which the porogen comprises an ionically-crosslinked polymer, a thermosensitive polymer, a thermoresponsive polymer, a pH-sensitive polymer, or a photocleavable polymer (US 2014-0178964, incorporated herein by reference). The polymer matrix is made of a durable polymer relative to the sacrificial porogen such that the polymer matrix withstands physical or chemical changes that cause porogen sacrifice. For example, polymer matrix is covalently crosslinked, withstands a change (e.g., increase) in temperature, withstands a pH change (e.g., decrease) or change in ionic strength or composition (e.g., contact with a divalent cation chelator), or withstands exposure to light (e.g., UV light).

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Similarly, cell populations are substantially free of other cellular material, or culture medium. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
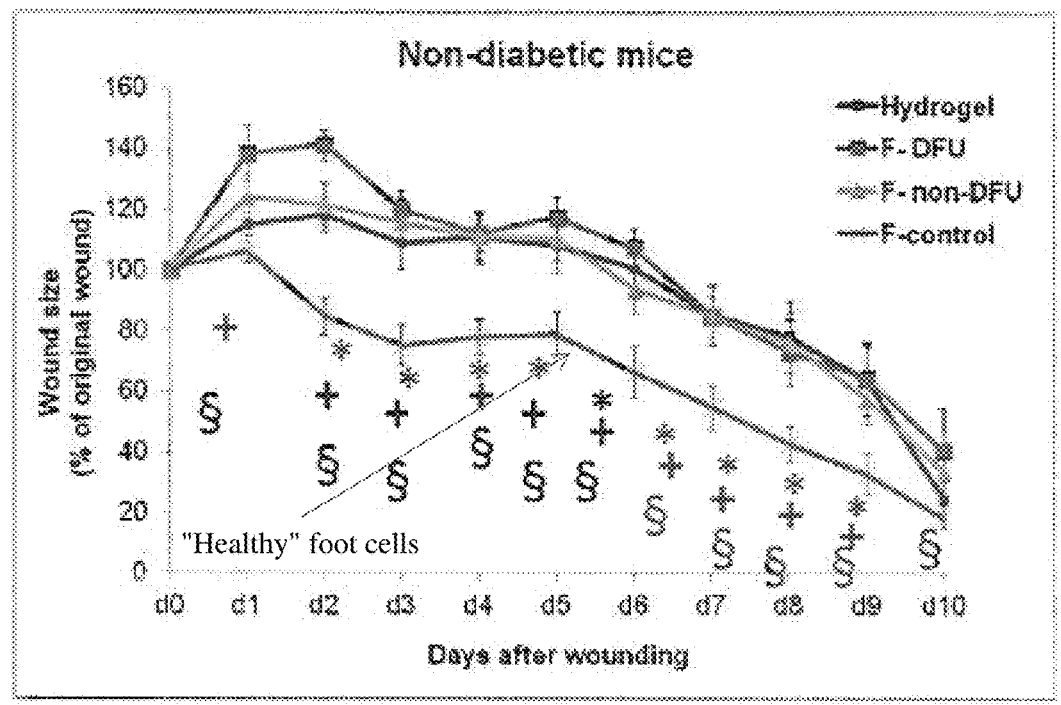
FIG. 1 is a line graph depicting the effect of hydrogels containing fibroblasts (originating from the skin area adjacent to an existing diabetic foot ulcer, originating from the skin of a foot of a diabetic subject without a foot ulcer, or originating from the skin of the foot of a non-diabetic subject) on wound size and time for wound closure in non-diabetic mice.

The present invention features compositions comprising hydrogels and fibroblasts and their use in wound healing, e.g., in diabetic subjects.

Diabetes is classified into four clinical classes: Type 1, Type 2, gestational, and diabetes due to other causes. Type 1 diabetes is caused by destruction of beta cells in the pancreas, typically leading to insulin deficiency. Type 2 diabetes is characterized by insulin resistance or hyperinsulinemia and patients often develop a progressive defect in insulin secretion. Gestational diabetes is characterized by glucose intolerance during pregnancy. Other types diabetes are due to or associated with other causes, e.g., genetic defects in insulin activity (e.g., genetic defects in the insulin receptor), pancreatic disease, hormonal diseases, genetic defects of beta cell function, or drug/chemical exposure. See, e.g., "Standards of Medical Care in Diabetes—2013." *Diabetes Care*. 36.S1(2013):S11-S66; and Harris. "Classification, Diagnostic Criteria, and Screening for Diabetes." *Diabetes in America*. National Institutes of Health, NIH Publication No. 95-1468. Chapter 2 (1995):15-36, incorporated herein by reference.

A subject is diagnosed as having diabetes if he or she meets one or more of following criteria: a hemoglobin A1C (A1C) level of 6.5% or higher, a fasting plasma glucose (FPG) concentration of 126 mg/dL or greater, a 2-h plasma glucose concentration of 200 mg/dL or greater during an oral glucose tolerance test (OGTT), or for subjects having symptoms of hyperglycemia or hyperglycemic crisis, a random plasma glucose concentration of 200 mg/dL or greater. Thus, by "high glucose" tissue is meant tissue from a subject diagnosed with diabetes. Fasting is typically defined as no caloric intake for at least 8 hours prior to testing. The tests described herein are performed under conditions and standards generally known in the art, e.g., recommended by the World Health Organization and/or American Diabetes Association. See, e.g., "Standards of Medical Care in Diabetes—2013." *Diabetes Care*. 36.S1(2013):S11-S66, incorporated herein by reference.

Because of the complications associated with diabetes (e.g., neuropathy, a weakened immune system, and narrowed arteries), even minor wounds in diabetic subjects are challenging to heal, and they either do not heal or heal slowly. Non-healing wounds progress to infection, necrosis, tissue loss, and gangrene, and eventually, amputation is necessary. As a result, more than 60% of amputations in the U.S. occurred in subjects with diabetes.

Diabetic foot ulcers are chronic, non-healing wounds on the feet of diabetic patients. These foot ulcers affect between 15-25% of Americans who have diabetes. Diabetic foot ulcers are associated with significant morbidities, a decrease in the quality of life, and often, amputation of a lower extremity.

Before the invention, previous studies showed that fibroblasts from diabetic wounds (e.g., taken from an area adjacent to a diabetic foot ulcer) were senescent and failed to grow in cultures. These characteristics were thought to be major factors in the impairment of wound healing. Surprisingly and unexpectedly, the results herein show that fibroblasts from diabetic skin near ulcers are superior in their ability to mediate wound healing, e.g., in diabetic patients. These results indicate that fibroblasts from diabetic foot ulcers retain a metabolic memory that allows them to perform better in diabetic wounds (such as those characterized by excessive inflammation) compared to fibroblasts from non-diabetic subjects. Thus, contrary to previous findings, these results show that fibroblasts taken from the area that is adjacent to diabetic foot ulcers are not senescent and can be isolated and grown in cultures.

In some examples, metabolic memory refers to the persistence of a diabetic phenotype when cells are removed from a diabetic patient (e.g., the site of a diabetic foot ulcer) and grown extensively (e.g., 4-10 passages) in a normal glucose environment (e.g., normal culture media as distinguished from high glucose culture media). See, e.g., Ceriello. Vascular Pharmacol. 57(2012):133-138; Aschner et al. Diabetes Technol. Ther. 14.1(2012):S68-S74 (e.g., at page S-72); Ceriello et al. J. Clin. Endocrinol. Metab. 94.2(2009): 410-415; Cooper. Pediatric Diabetes. 10(2009):343-346; and Ihnat et al. Diabet. Med. 24(2007):582-586, each of which is incorporated herein by reference in its entirety.

For example, a fibroblast from a diabetic wound has metabolic memory, e.g., with an epigenetic basis or associated with an epigenetic change compared to a non-diabetic fibroblast or a fibroblast in a diabetic patient that is derived from a site located away from a diabetic wound.

A "diabetic phenotype" in this context, is defined as the expression profile of one or more protein/gene markers and/or the epigenetic alterations in cells derived from a diabetic patient (e.g., the site of a diabetic foot ulcer).

In some embodiments, epigenetic alterations include methylation of a gene.

Protein/gene markers and/or epigenetic alterations are determined by standard methods in the art, e.g., real-time polymerase chain reaction (RT-PCR) or gene expression arrays, such as microarrays.

Specifically, hydrogels developed by Mooney et al. (see, e.g., U.S. Pat. No. 8,067,237, US 2012-0100182, US 2013-0177536, US 2012-0121539, US 2013-0302396, US 2013-0331343, US 2014-0178964, US 2015-0072009, WO 12/048165, WO 12/149358, WO 12/148684, and WO 12/167230, incorporated herein by reference) were used to deliver the fibroblasts of the invention into the wounds of diabetic mice. Fibroblasts from the skin of non-diabetic subjects or diabetic subjects without foot ulceration were injected in the wounds of diabetic mice. Fibroblasts taken from the area adjacent to foot ulcers of diabetic patients performed better at wound healing than fibroblasts from the skin of non-diabetic subjects or diabetic patients without foot ulceration when injected in the wounds of diabetic mice. In contrast, fibroblasts from non-diabetic subjects performed better than fibroblasts from diabetic subjects, with or without ulceration, in non-diabetic mice.

Fibroblasts from the diabetic skin adjacent to the foot ulcer area likely retain their epigenetic changes when isolated and grown in culture. The metabolic memory that these cells retain from their original diabetic wound environment and likely underlying epigenetic changes enable them to perform better (e.g., survive longer, proliferate faster, and mediate healing) in diabetic wounds than fibroblasts from non-diabetic subjects or diabetic patients without foot ulceration. As chronic diabetic wounds are characterized by chronic inflammation, the metabolic memory (e.g., associated with epigenetic changes) in fibroblasts from diabetic foot ulcers likely facilitate improved adjustment and survival of these cells in the diabetic wound environment. Thus, the invention harnesses this metabolic memory of the fibroblasts to develop more efficient therapeutic approaches for the management of diabetic wounds (e.g., foot ulcers).

The devices of the invention provide scaffold compositions containing hydrogels that deliver these fibroblasts having superior wound-healing capabilities to a subject in need thereof. The methods and data presented herein demonstrate that these compositions are useful for the treatment of wounds, e.g., in diabetic subjects.

The invention also provides a wound product that is used for the management of diabetic foot ulceration and other chronic wounds.

In some embodiments, the invention provides a device containing a hydrogel, a fibroblast, and a stem cell for use in wound healing therapy. For example, the composition is used with induced pluripotent stem cell (iPSC) technologies to generate new stem cells for wound therapy. A stem cell is an undifferentiated cell that differentiates into a mature functional tissue specific cell upon contact with appropriate microenvironment, e.g., growth factors and other differentiating agents. In some cases, the devices described herein represent such a microenvironment. Each device constitutes a factory that attracts/accepts, reproduces, sustains, educates, and sends forth to surrounding bodily tissues tissue-specific cells that are capable of colonizing and regenerating damaged tissue. In some examples, the wound repair potency of foot ulcer fibroblasts is enhanced following their reprogramming to induced pluripotent stem cells (iPSC), e.g., in ways that enhance the cells' repair-promoting functions, e.g., functions that are mediated by epigenetic control.

Hydrogel structures are seeded with one or more populations of purified or isolated cells (e.g., isolated fibroblasts). The term "isolated" used in reference to a cell type, e.g., a fibroblast, means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS). Optionally, the device is seeded with two or more substantially pure populations of cells. The populations are spatially or physically separated, e.g., one population is encapsulated, or the cells are allowed to come into with one another. The scaffold composition or structural support not only provides a surface upon which cells are seeded/attached but indirectly affects production/education of cell populations by housing a second (third, or several) cell population(s) with which a first population of cells associates (cell-cell adhesion).

The scaffolds compositions are seeded in vitro or in vivo. For example, scaffolds compositions are seeded by incubating the structure in a solution containing the cells. Alternatively, cells are injected/titrated into the scaffold composition or recruited to migrate into the device. In yet another example, the scaffold composition is built in stages with each layer of the multicomponent scaffold being seeded prior to laying down of another layer or before adherences of another pre-formed component. Different cell types, e.g., stem vs. differentiated, support vs. therapeutic, are optionally co-resident in the scaffold housing. Cells optionally vary in phenotype, e.g., differentiation state, activation state, metabolic state, or functional state. In general scaffolds of the invention may comprise any cell population competent to participate in regeneration, replacement or repair of a target tissue or organ. For example, the cells are fibroblasts for use in wound healing.

Cells are optionally genetically manipulated by the introduction of exogenous genetic sequences or the inactivation or modification of endogenous sequences. For example, recombinant genes are introduced to cause the cells to make proteins that are otherwise lacking in the host or target tissue. Production of scarce but desirable proteins (in the context of certain tissues) is augmented by transplanting genetically engineered cells. Cells used to seed the scaffold are capable of degrading the scaffold matrix over a desired period time in order to migrate through and out of the scaffold matrix. Scaffold matrices are selected such that they are susceptible to degradation by certain cell types seeded within the matrix. For example, scaffold materials and cells are selected and designed such that all or some of the cells seeded within the scaffold compositions require a certain desired period of time degrade the scaffold matrix sufficiently to migrate through it and reach the surrounding tissue. The delay in the release of the cells to the surrounding tissue is controlled by varying the composition of the scaffold, to allow optimal time to signal the cells to multiply, differentiate, or achieve various phenotypes. General mammalian cell culture techniques, cell lines, and cell culture systems are described in Doyle, A., Griffiths, J. B., Newell, D. G., (eds.) *Cell and Tissue Culture: Laboratory Procedures*, Wiley, 1998, the contents of which are incorporated herein by reference.

Cells secrete enzymes that degrade the material of the scaffold composition, thereby controlling the rate at which cells exit the scaffold. For example, migrating cells typically secrete collagenases and plasmin to degrade their matrix and allow cell movement. The rate of cells exiting may thus be regulated by controlling the density and susceptibility to these enzymes of oligopeptides used as either cross-links in the material or as components of the main chains. Certain materials are degraded in a preprogrammed manner independent of cell action (e.g. hydrolytic degradation of poly (lactide-co glyolide) as a degradable scaffold matrix. The scaffold compositions may be prepared such that the degradation time may be controlled by using a mixture of degradable components in proportions to achieve a desired degradation rate. Alternatively, the cells themselves aid in the degradation. For example, scaffold compositions are sensitive to degradation by materials secreted by the cells themselves that are seeded within the scaffold matrix. One example of this is the use of metalloproteinase (MMP)-sensitive substrate in the scaffold matrix; cells exit when the seeded cells have secreted sufficient MMP to begin degradation of the matrix.

Cells incubated in the scaffold composition are educated and induced to migrate out of the scaffold to directly affect a target tissue, e.g., and injured tissue site. For example, stromal vascular cells and smooth muscle cells are useful in sheetlike structures are used for repair of vessel-like structures such as blood vessels or layers of the body cavity. Such structures are used to repair abdominal wall injuries or defects such as gastroschisis. Similarly, sheetlike scaffold compositions seeded with dermal stem cells and/or keratinocytes are used in bandages or wound dressings for regeneration of dermal tissue.

Scaffold Compositions and Architecture

Components of the scaffold compositions are organized in a variety of geometric shapes (e.g., beads, pellets), niches, planar layers (e.g., thin sheets). For example, multicomponent scaffold compositions are constructed in concentric layers each of which is characterized by different physical qualities (% polymer, % crosslinking of polymer, chemical composition of scaffold, pore size, porosity, and pore architecture, stiffness, toughness, ductility, viscoelasticity, and or composition of bioactive substances such as growth factors, homing/migration factors, differentiation factors. Each niche has a specific effect on a cell population, e.g., promoting or inhibiting a specific cellular function, proliferation, differentiation, elaboration of secreted factors or enzymes, or migration. Cells incubated in the scaffold composition are educated and induced to migrate out of the scaffold to directly affect a target tissue, e.g., and injured tissue site. For example, stromal vascular cells and smooth muscle cells are useful in sheetlike structures are used for repair of vessel-like structures such as blood vessels or layers of the body cavity. For example, such structures are used to repair abdominal wall injuries or defects such as gastroschisis. Similarly, sheetlike scaffold compostions seeded with dermal stem cells and/or keratinocytes are used in bandages or wound dressings for regeneration of dermal tissue. The device is placed or transplanted on or next to a target tissue, in a protected location in the body, next to blood vessels, or outside the body as in the case of an external wound dressing. Devices are introduced into or onto a bodily tissue using a variety of known methods and tools, e.g., spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches. Devices can also be assembled in place, for example by senquentially injecting or inserting matrix materials. Scaffold devices are optionally recharged with cells or with bioactive compounds, e.g., by sequential injection or spraying of substances such as growth factors or differentiation factors.

A scaffold or scaffold device is the physical structure upon which or into which cells associate or attach, and a scaffold composition is the material from which the structure is made. For example, scaffold compositions include biodegradable or permanent materials such as those listed below. The mechanical characteristics of the scaffold composition vary according to the application or tissue type for which regeneration is sought. It is biodegradable (e.g., collagen, alginates, polysaccharides, polyethylene glycol (PEG), poly (glycolide) (PGA), poly(L-lactide) (PLA), or poly(lactide-co-glycolide) (PLGA) or permanent (e.g., silk). In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel)

to glassy, rubbery, brittle, tough, elastic, stiff. The structures contain pores, which are nanoporous, microporous, or macroporous, and the pattern of the pores is optionally homogeneous, heterogenous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold composition. "GGGGRGDSP" is disclosed as SEQ ID NO: 1.

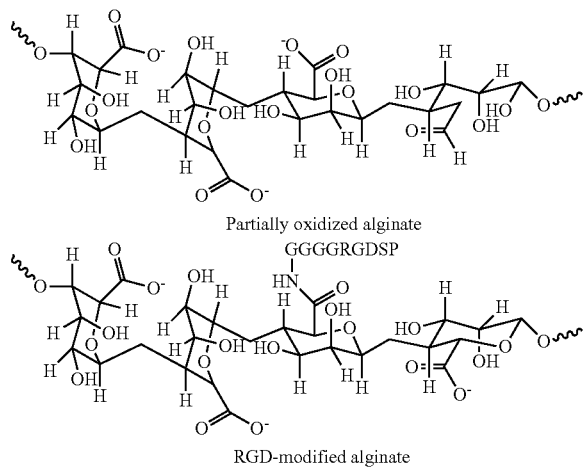

Partially oxidized alginate

RGD-modified alginate

The scaffold composition comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly (lysine), polyesters such as polyhydroxybutyrate and poly-epsilon.-caprolactone, polyanhydrides; polyphosphazines, poly(vinyl alcohols), poly(alkylene oxides) particularly poly (ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

One preferred scaffold composition includes an RGD-modified alginate. Another preferred scaffold composition a macroporous poly-lactide-co-glycolide (PLG).

In other embodiments, scaffold compositions comprise a non-biodegradable material. Exemplary non-biodegradable materials include, but are not limited to, metal, plastic polymer, or silk polymer. Moreover, scaffold compositions are composed of a biocompatible material. This biocompatible material is non-toxic or non-immunogenic.

The scaffold compositions are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for dental applications, wound dressings chondrocyte transplantation and as a matrix for other cell types.

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Prefereably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer. U.S. Pat. No. 6,642,363, incorporated herein by reference discloses methods for making and using polymers containing polysachharides such as alginates or modified alginates that are particularly useful for cell transplantation and tissue engineering applications.

Useful polysaccharides other than alginates include agarose and microbial polysaccharides such as those listed in the table below.

Polysaccharide Scaffold Compositions

| Polymers[a] | Structure |
|---|---|
| Fungal | |
| Pullulan (N) | 1,4-; 1,6-α-D-Glucan |
| Scleroglucan (N) | 1,3; 1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-; 1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2; 1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N—neutral, A = anionic and C = cationic.

The scaffold compositions of the invention are porous or non-porous. For example, the scaffold compositions are nanoporous having a diameter of less than about 10 nm; microporous wherein the diameter of the pores are preferably in the range of about 100 nm-20 μm; or macroporous wherein the diameter of the pores are greater than about 20

μm, more preferably greater than about 100 μm and even more preferably greater than about 400 μm. In one example, the scaffold composition is macroporous with aligned pores of about 400-500 μm in diameter. The preparation of polymer matrices having the desired pore sizes and pore alignments are described in the Examples. Other methods of preparing porous hydrogel products are known in the art. (U.S. Pat. No. 6,511,650 incorporated herein by reference).

Scaffold compositions of the present invention contain an external surface. Scaffold compositions of the present invention alternatively, or in addition, contain an internal surface. External or internal surfaces of the scaffold compositions are solid or porous. Pore size is less than about 10 nm, in the range of about 100 nm-20 μm in diameter, or greater than about 20 μm.

Scaffold compositions of the present invention comprise one or more compartments.

The scaffold composition regulates migration of fibroblasts through the physical or chemical characteristics of the scaffold itself. For example, the scaffold composition is differentially permeable, allowing cell migration only in certain physical areas of the scaffold. The permeability of the scaffold composition is regulated, for example, by selecting or engineering a material for greater or smaller pore size, density, polymer cross-linking, stiffness, toughness, ductility, or viscoelascticity. The scaffold composition contains physical channels or paths through which cells can move more easily towards a targeted area of egress of the device or of a compartment within the device. The scaffold composition is optionally organized into compartments or layers, each with a different permeability, so that the time required for a cell to move through the device is precisely and predictably controlled. Migration is also regulated by the degradation, de- or re-hydration, oxygenation, chemical or pH alteration, or ongoing self-assembly of the scaffold composition.

Bioactive Compositions

The device includes one or more bioactive compositions. Bioactive compositions are purified naturally-occurring, synthetically produced, or recombinant compounds, e.g., polypeptides, nucleic acids, small molecules, or other agents. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

Optionally, bioactive compositions are covalently or non-covalently linked to the scaffold composition. Bioactive compositions comprise an element, either covalently or non-covalently bonded to the surface of the scaffold composition, that aids in the wound healing mediated by the fibroblasts. For example, the bioactive composition promote the survival and/or proliferation of fibroblasts. In other cases, the bioactive composition reduces inflammation, e.g., at the site of the wound. In some cases, the second bioactive composition is covalently linked to the scaffold composition, keeping the composition relatively immobilized in or on the scaffold composition. In other cases, the second bioactive composition is noncovalently associated with the scaffold. Noncovalent bonds are generally one to three orders of magnitude weaker than covalent bonds permitting diffusion of the factor out of the scaffold and into surrounding tissues. Noncovalent bonds include electrostatic, hydrogen, van der Waals, π aromatic, and hydrophobic.

The bioactive composition alters a cell function or behavior, e.g., level of differentiation, state of activation, motility, or gene expression, of a cell. For example, at least one cell adhesion molecule is incorporated into or onto the polymer matrix. Such molecules are incorporated into the polymer matrix prior to polymerization of the matrix or after polymerization of the matrix. Examples of cell adhesion molecules include but are not limited to peptides, proteins and polysaccharides. More specifically, cell adhesion molecules include fibronectin, laminin, collagen, thrombospondin 1, vitronectin, elastin, tenascin, aggrecan, agrin, bone sialoprotein, cartilage matrix protein, fibronogen, fibrin, fibulin, mucins, entactin, osteopontin, plasminogen, restrictin, serglycin, SPARC/osteonectin, versican, von Willebrand Factor, polysaccharide heparin sulfate, connexins, collagen, RGD (Arg-Gly-Asp) and YIGSR (Tyr-Ile-Gly-Ser-Arg) (SEQ ID NO: 12) peptides and cyclic peptides, glycosaminoglycans (GAGs), hyaluronic acid (HA), condroitin-6-sulfate, integrin ligands, selectins, cadherins and members of the immunoglobulin superfamily. Other examples include neural cell adhesion molecules (NCAMs), intercellular adhesion molecules (ICAMs), vascular cell adhesion molecule (VCAM-1), platelet-endothelial cell adhesion molecule (PECAM-1), L1, and CHL1.

Examples of some of these molecules and their function are shown in the following table.

ECM Proteins and Peptides and Role in Cell Function

| Protein | Sequence | Seq. ID No: | Role |
|---|---|---|---|
| Fibronectin | RGDS | 7 | Adhesion |
|  | LDV |  | Adhesion |
|  | REDV | 8 | Adhesion |
| Vitronectin | RGDV | 9 | Adhesion |
| Laminin A | LRGDN | 10 | Adhesion |
|  | IKVAV | 11 | Neurite extension |
| Laminin B1 | YIGSR | 12 | Adhesion of many cells, via 67 kD laminin receptor |
|  | PDSGR | 13 | Adhesion |
| Laminin B2 | RNIAEIIKDA | 14 | Neurite extension |
| Collagen 1 | RGDT | 15 | Adhesion of most cells |
|  | DGEA | 16 | Adhesion of platelets, other cells |
| Thrombospondin | RGD |  | Adhesion of most cells |
|  | VTXG | 17 | Adhesion of platelets Hubbell, J A |

(1995): Biomaterials in tissue engineering. Bio/Technology 13:565-576. One-letter abbreviations of amino acids are used, X stands for any amino acid. Additional examples of suitable cell adhesion molecules are shown below.

Amino Acid Sequences Specific for Proteoglycan Binding from Extracellular Matrix Proteins

| SEQUENCE | SEQ. ID. NO. | PROTEIN |
|---|---|---|
| XBBXBX* | 2 | Consensus sequence |
| PRRARV | 3 | Fibronectin |
| YEKPGSPPREVVPRPRPGV | 4 | Fibronectin |
| RPSLAKKQRFRHRNRKGYRSQRGHSRGR | 5 | Vitronectin |
| RIQNLLKITNLRIKFVK | 6 | Laminin |

Particularly preferred cell adhesion molecules are peptides or cyclic peptides containing the amino acid sequence arginine-glycine-aspartic acid (RGD) which is known as a cell attachment ligand and found in various natural extracellular matrix molecules. A polymer matrix with such a modification provides cell adhesion properties to the scaffold composition, and sustains long-term survival of mammalian cell systems, as well as supporting cell growth and differentiation.

Coupling of the cell adhesion molecules to the polymer matrix is accomplished using synthetic methods which are in general known to one of ordinary skill in the art and are described in the examples. Approaches to coupling of peptides to polymers are discussed in Hirano and Mooney, *Advanced Materials, p.* 17-25 (2004). Other useful bonding chemistries include those discussed in Hermanson, *Bioconjugate Techniques, p.* 152-185 (1996), particularly by use of carbodiimide couplers, DCC and DIC (Woodward's Reagent K). Since many of the cell adhesion molecules are peptides, they contain a terminal amine group for such bonding. The amide bond formation is preferably catalyzed by 1-ethyl-3-(3-dimethylaminopropyl)carbodiimide (EDC), which is a water soluble enzyme commonly used in peptide synthesis. The density of cell adhesion ligands, a critical regulator of cellular phenotype following adhesion to a biomaterial. (Massia and Hubbell, *J. Cell Biol.* 114:1089-1100, 1991; Mooney et al., J. Cell Phys. 151:497-505, 1992; and Hansen et al., *Mol. Biol. Cell* 5:967-975, 1994) can be readily varied over a 5-order of magnitude density range.

Device Construction

The scaffold structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into cell scaffold structures using methods known in the art, e.g., injection molding, lyophillization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The device is assembled in vivo in several ways. The scaffold composition is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In one example, the ungelled or unformed scaffold material is mixed with bioactive substances and cells prior to introduction into the body or while it is introduced. The resultant in vivo/in situ assembled scaffold contains a mixture of these substances and cells.

In situ assembly of the scaffold composition occurs as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the scaffold material by a radiation beam or through a heat or light conductor, such as a wire or fiber optic cable or an ultrasonic transducer. Alternatively, a shear-thinning material, such as an ampliphile, is used which re-cross links after the shear force exerted upon it, for example by its passage through a needle, has been relieved.

Suitable hydrogels for both in vivo and ex vivo assembly of scaffold devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A. 99:5133-5138. A method for reversible gellation following shear thinning is exemplied in Lee et al., 2003, Adv. Mat. 15:1828-1832

A multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. Non-concentric compartments are formed by injecting material into different locations in a previously injected layer. A multi-headed injection device extrudes compartments in parallel and simultaneously. The layers are made of similar or different scaffolding compositions differentially doped with bioactive substances and different cell types. Alternatively, compartments self-organize based on their hydrophilic/phobic characteristics or on secondary interactions within each compartment.

Growth Factors and Incorporation of Compositions into/ onto a Scaffold Device

Bioactive substances that influence growth, development, movement, and other cellular functions are introduced into or onto the scaffold structures. Such substances include BMP, bone morphogenetic protein; ECM, extracellular matrix proteins or fragments thereof; EGF, epidermal growth factor; FGF-2, fibroblast growth factor 2; NGF, nerve growth factor; PDGF, platelet-derived growth factor; PlGF, placental growth factor; TGF, transforming growth factor, and VEGF, vascular endothelial growth factor, phosphatase inhibitors. Cell-cell adhesion molecules (cadherins, integrins, ALCAM, NCAM, proteases) are optionally added to the scaffold composition. Exemplary growth factors and ligands are provided in the tables below. Preferably, the growth factor/ligand comprises VEGF, PDGF, HGF, and/or RGD.

Growth Factors Used for Angiogenesis

| Growth factor | Abbreviation | Relevant activities |
|---|---|---|
| Vascular endothelial growth factor | VEGF | Migration, proliferation and survival of ECs |
| Basic fibroblast growth factor | bFGF-2 | Migration, proliferation and survival of ECs and many other cell types |
| Platelet-derived growth factor | PDGF | Promotes the maturation of blood vessels by the recruitment of smooth muscle cells |
| Angiopoietin-1 | Ang-1 | Strengthens EC-smooth muscle cell interaction |
| Angiopoietin-2 | Ang-2 | Weakens EC-smooth muscle cell interaction |
| Placental growth factor | PlGF | Stimulates angiogenesis |
| Transforming growth factor | TGF | Stabilizes new blood vessels by promoting matrix deposition |

Growth Factors Used for Bone Regeneration

| Growth factor | Abbreviation | Relevant activities |
|---|---|---|
| Transforming growth factor-β | TGF-β | Proliferation and differentiation of bone-forming cells |
| Bone morphogenetic protein | BMP | Differentiation of bone-forming cells |
| Insulin-like growth factor | IGF-1 | Stimulates proliferation of osteoblasts and the synthesis of bone matrix |
| Fibroblast growth factor-2 | FGF-2 | Proliferation of osteoblasts |
| Platelet-derived growth factor | PDGF | Proliferation of osteoblasts |

Growth Factors Used for Wound Healing

| Growth Factor | Abbreviation | Relevant activities |
|---|---|---|
| Platelet-derived growth factor | PDGF | Active in all stages of healing process |
| Epidermal growth factor | EGF | Mitogenic for keratinocytes |
| Transforming growth factor-β | TGF-β | Promotes keratinocyte migration, ECM synthesis and remodeling, and differentiation of epithelial cells |
| Fibroblast growth factor | FGF | General stimulant for wound healing |

Growth Factors Used for Tissue-Engineering

| Growth factor | Abbreviation | Molecular weight (kDa) | Relevant activities | Representative supplier of rH growth factor |
|---|---|---|---|---|
| Epidermal growth factor | EGF | 6.2 | Proliferation of epithelial, mesenchymal, and fibroblast cells | PeproTech Inc. (Rocky Hill, NJ, USA) |
| Platelet-derived growth factor | PDGF-AA PDGF-AB PDGF-BB | 28.5 25.5 24.3 | Proliferation and chemoattractant agent for smooth muscle cells; extracellular matrix synthesis and deposition | PeproTech Inc. |
| Transforming growth factor-α | TFG-α | 5.5 | Migration and proliferation of keratinocytes; extracellular matrix synthesis and deposition | PeproTech Inc. |
| Transforming growth factor-β | TGF-β | 25.0 | Proliferation and differentiation of bone forming cells; chemoattractant for fibroblasts | PeproTech Inc. |
| Bone morphogenetic protein | BMP-2 BMP-7 | 26.0 31.5 | Differentiation and migration of bone forming cells | Cell Sciences Inc. (Norwood, MA, USA) |
| Basic fibroblast growth factor | bFGF/FGF-2 | 17.2 | Proliferation of fibroblasts and initiation of angiogenesis | PeproTech Inc. |
| Vascular endothelial growth factor | VEGF$_{165}$ | 38.2 | Migration, proliferation, and survival of endothelial cells | PeproTech Inc. | rH, recombinant human

Immobilized Ligands Used in Tissue Engineering

| Immobilized ligand* | ECM molecule source | Application |
|---|---|---|
| RGD | Multiple ECM molecules, including fibronectin, vitronectin, laminin, collagen and thrombospondin | Enhance bone and cartilage tissue formation in vitro and in vivo Regulate neurite outgrowth in vitro and in vivo Promote myoblast adhesion, proliferation and differentiation Enhance endothelial cell adhesion and proliferation |
| IKVAV (SEQ ID NO: 11) YIGSR (SEQ ID NO: 12) RNIAEIIKDI (SEQ ID NO: 30) | Laminin | Regulate neurite outgrowth in vitro and in vivo |
| Recombinant fibronectin fragment (FNIII$_{7-10}$) | Fibronectin | Promote formulation of focal contacts in pre-osteoblasts |
| Ac-GCRDGPQ-GIWGQDRCG (SEQ ID NO: 31) | Common MMP substrates, (e.g. collagen, fibronectin, laminin) | Encourage cell-mediated proteolytic degradation, remodeling and bone regeneration (with RGD and BMP-2 presentation) in vivo |

*Sequences are given in single-letter amino acid code.
MMP, matrix metalloproteinase.

The release profiles of bioactive substances from scaffold devices is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors). In both cases, the time frame of release determines the time over which effective cell delivery by the device is desired.

Carrier systems for tissue regeneration are described in the table below.

Polymeric Carriers Used to Deliver Various Growth Factors and the Type of Tissues Regenerated

| Growth factor | Carrier | Tissue regenerated |
|---|---|---|
| EGF | Gelatin | Dermis |
|  | PET suture | Tendon |
|  | PVA sponge | Dermis |
| PDGF | Chitosan-PLLA scaffold | Craniofacial bone |
|  | CMC gel | Dermis |
|  | Fibrin | Ligament |
|  | Porous HA | Long Bone |
| TGF-β | Alginate | Cartilage |
|  | PLA | Long Bone |
|  | CaP-titanium mesh | Craniofacial bone |
|  | Polyoxamer; PEO gel | Dermis |
| rhBMP-2 | Collagen sponge | Long bone Craniofacial bone |

-continued

| Growth factor | Carrier | Tissue regenerated |
|---|---|---|
|  | HA-TCP granules | Spinal bone |
|  | HA-collagen | Long bone |
|  | PLA-DX-PEG | Ectopic and hip bone |
| rHBMP-7 | HA | Spinal bone |
|  | Collagen-CMC | Spinal bone |
|  | Porous HA | Craniofacial bone |
| bFGF | Chitosan | Dermis |
|  | Heparin-alginate | Blood vessels |
|  | EVAc microspheres | Blood vessels |
|  | Fibrin matrices | Blood vessels |
| VEGF | PLG scaffold | Blood vessels |
|  | PLG scaffold | Blood vessels |
|  | PLG microspheres | Blood vessels |
|  | Fibrin mesh | Blood vessels |

Abbreviations: PET, poly (ethylene terepthalate); PVA, polyvinyl alcohol; PLLA, poly (L-lactic acid); CMC, carboxymethylcellulose; HA, hydroxyapatite; PLA, poly(D,L-lactic acid); CaP, calcium phosphate; PEO, poly (ethylene oxide); TCP, tricalcium phosphate; PEG, poly(ethylene glycol); -DX-, -p-dioxanone-; EVAc, ethylene vinyl acetate; PLG, poly(lactide-co-glycolide).

The bioactive substances are added to the scaffold compositions using known methods including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, longterm presentation of a bioactive substance on the scaffold in a defined conformation. Exemplary reagents for covalent coupling of such substances are provided in the table below.

Methods to Covalently Couple Peptides/Proteins to Polymers

| Functional Group of Polymer | Coupling reagents and cross-linker | Reacting groups on proteins/peptides |
|---|---|---|
| —OH | Cyanogen bromide (CNBr) | —NH$_2$ |
|  | Cyanuric chloride |  |
|  | 4-(4,6-Dimethoxy-1,3,5-triazin-2-yl)-4-methyl-morpholinium chloride (DMT-MM) |  |
| —NH$_2$ | Diisocyanate compounds | —NH$_2$ |
|  | Diisothoncyanate compounds | —OH |
|  | Glutaraldehyde |  |
|  | Succinic anhydride |  |
| —NH$_2$ | Nitrous Acid | —NH$_2$ |
|  | Hydrazine + nitrous acid | —SH |
|  |  | —Ph—OH |
| —NH$_2$ | Carbodiimide compounds (e.g., EDC, DCC)[a] | —COOH |
|  | DMT-MM |  |
| —COOH | Thionyl chloride | —NH$_2$ |
|  | N-hydroxysuccinimide |  |
|  | N-hydroxysulfosuccinimide + EDC |  |
| —SH | Disulfide compound | —SH |

[a]EDC: 1-ethyl-3-(3-dimethylaminopropyl) carbodiimide hydrochloride; DCC: dicyclohexylcarbodiimide Bioactive substances are capable of inducing migration of the transplanted cells and their progeny out of the polymer matrix. Other preferred bioactive substances are capable of maintaining cell viability, promoting cell proliferation or preventing premature terminal differentiation of the transplanted cells. Such bioactive substances are used alone or in combination to achieve the desired result.

Bioactive substances suitable for use in the present invention include, but are not limited to: growth factors, hormones, neurotransmitters, neurotransmitter or growth factor receptors, interferons, interleukins, chemokines, cytokines, colony stimulating factors, chemotactic factors, MMP-sensitive substrate, extracellular matrix components; such as growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). Splice variants of any of the above mentioned proteins, and small molecule agonists or antagonists thereof that may be used advantageously to alter the local balance of pro and anti-migration and differentiation signals are also contemplated herein.

Examples of cytokines as mentioned above include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

Suitable bioactive substances useful in accordance with the invention also include but are not limited to DNA molecules, RNA molecules, antisense nucleic acids, ribozymes, plasmids, expression vectors, marker proteins, transcription or elongation factors, cell cycle control proteins, kinases, phosphatases, DNA repair proteins, oncogenes, tumor suppressors, angiogenic proteins, anti-angiogenic proteins, cell surface receptors, accessory signaling molecules, transport proteins, enzymes, anti-bacterial agents, anti-viral agents, antigens, immunogens, apoptosis-inducing agents, anti-apoptosis agents, and cytotoxins.

For some applications, the scaffold compositions of the invention include at least one cell growth factor that prevents premature terminal differentiation of the transplanted cells in the polymer matrix and induces migration of the transplanted cells and their progeny out of the polymer matrix. Cell growth factors are incorporated into the polymer matrix prior to polymerization of fabrication or may be coupled to the polymer matrix after polymerization. The choice of growth factor will depend upon the type of cells and the influence of a particular growth factor on those cells such that the cells are directed to bypass their normal tendency to differentiate, and remain in a proliferative phase until a sufficient number of cells is attained to regenerate the targeted tissue and for the cells to have also migrated from the scaffold.

Scaffold compositions of the invention optionally comprise at least one non-viral gene therapy vector such that either the transplanted cells or host cells in the vicinity of the implant would take up and express gene that lead to local availability of the desired factor for a desirable time frame. Such non-viral vectors include, but are not limited to, cationic lipids, polymers, targeting proteins, and calcium phosphate.

For regeneration of muscular tissue, the cells seeded in the scaffold composition are myoblasts and the preferred combination of growth factors is HGF and FGF2. FGF2 is particularly useful in preventing the premature differentiation of the transplanted cells, while HGF induces migration of the cells from the scaffold composition. The incorporation of the two growth factors significantly increased the viability and migration of the seeded myoblasts as discussed below.

The biocompatible scaffold compositions of the invention are useful in a broad range of in vivo and in vitro regenerative medicine and tissue engineering. Devices are designed and manufactured for a wide variety of injuries, diseases, conditions and cell therapies, and delivered to the treatment location using surgical, endoscopic, endovascular, and other techniques. The devices degrade and resorb after the treatment is successfully completed or remain in place permanently or semi-permanently. Cells are seeded ex vivo into the scaffold composition with autologous or allogeneic cells. The devices are particularly useful in regenerating heart tissue (ischemia lesions and scarring), dermal tissue (scarring, ulcers, burns), CNS tissue (spinal cord injury, MS, ALS, dopamine shortage), and for skeletal-muscle system repairs (tendons, ligaments, discs, post-surgical, hernias)

The invention also provides a method for treating a patient in need of wound healing and/or tissue regeneration, replacement or repair (e.g., at or around the site of a wound, such as a diabetic wound) comprises the step implanting a scaffold composition in or near the tissue in need of regeneration, repair or replacement. This method for treating a patient in need of wound healing involves implanting in the patient a biocompatible scaffold containing a macroporous, polymer matrix having at least a population of fibroblasts capable of mediating wound healing transplanted within the polymer matrix; and optionally at least one cell growth inductive factor that prevents terminal differentiation of the transplanted cells in the polymer matrix and induces migration of the transplanted cells and their progeny out of the polymer matrix. For example, the cell growth inductive factor(s) is a combination of HGF and FGF2.

The devices are useful to treat acute and chronic tissue disease or defects (e.g., non-healing or slow-healing wounds) in humans as well as animals such as dogs, cats, horses, and other domesticated and wild animals.

The devices increase the efficacy of stem and transgenic cell therapies, and the devices are tailored to suit each clinical problem with the appropriate choice of scaffold composition, pore size, bioactive substance(s) and cell types. The device solves the major problem of efficiently integrating therapeutic cells into target tissue. Physicians place the device near the site requiring therapy or regeneration, where it delivers a flow of cells (e.g., fibroblasts) to the target site. Unlike traditional scaffold compositions, the scaffold in the device exports cells such as fibroblasts after they have incubated, replicated and matured inside the device. The device has shown 20×+ improvements in viable cell delivery and tissue re-growth for damaged skeletal muscle. By matching its design to the specific cell type biochemistry, the device causes an extended stream of matured cells to migrate into the target tissue (e.g., the site of or area around a wound).

The devices offer several advantages over other scaffold systems. Maximum therapeutic efficacy is achieved, because cells are delivered in prime condition at the right time in the right quantities directly to the locus of a wound. Sustained delivery facilitates accretive integration of therapeutic cells into tissue at a desired location. The devices has been shown to be more efficient in viable cell delivery (110% for this device vs. 5% for the best alternative techniques). Thus, fewer cells are needed per treatment allowing successful therapies which might have failed at lower cell delivery rates. Lower cell numbers also permit autologous grafts, because fewer cells need to be harvested from the patient to be treated and less time is required between harvest and graft to proliferate cells in vitro. Since fewer cells are required, relative rare cells can be used. The devices also permit less expensive allogeneic grafts. Other advantages include rapid determination of the therapeutic benefit of any treatment and faster tissue growth and enhanced healing.

The invention provides a composition comprising a hydrogel and a population of fibroblasts. The hydrogel comprises pores, and the population of fibroblasts is bound to the hydrogel. For example, the population of fibroblasts is seeded into or onto the hydrogel.

In some cases, the population of fibroblasts comprises a fibroblast that is derived from a subject suffering from diabetes or a subject having a wound. For example, the wound is located in an extremity (e.g., an arm, hand, leg, or foot). In some cases, the wound is a diabetic wound. For example, the wound is an ulcer (e.g., an arm, hand, leg, or foot ulcer). Inflammation of tissues in and/or around a wound commonly occurs.

Diabetes is a chronic disease in which the body fails to properly regulate glucose metabolism. Types of diabetes include Type 1, Type 2, and gestational diabetes. Type 1 diabetes can develop at any age, but it commonly appears in children and adolescents. Type 1 diabetes is caused by a lack of sufficient insulin production to regulate glucose metabolism. Insulin is normally secreted by the beta cells of the pancreas to lower the amount of glucose in the blood. The lack of insulin production is caused by defective/damaged beta cells in the pancreas (which are cells that produce insulin). For example, damaged beta cells in Type 1 diabetics are destroyed by immune cells.

The onset of Type 2 diabetes can occur at any age. In Type 2 diabetes, the body is insulin resistant and the pancreas is unable to make enough insulin to overcome the resistance. In normal subjects, insulin leads to an uptake of glucose from the blood into cells. For example, cell types such as fat and muscle cells respond to insulin by absorbing glucose. Also, liver cells normally respond to insulin by reducing their secretion of glucose into the blood. However, when cells fail to insulin (as in Type 2 diabetes), blood glucose levels rise. Type 2 diabetes commonly occurs in overweight or obese subjects.

Symptoms and associated disorders of Type 1 and Type 2 diabetes due to the elevated blood sugar include increased thirst, frequent urination, extreme hunger, unexplained weight loss, slow-healing sores/wounds, presence of ketones in the urine, fatigue, blurred vision, blindness, high blood pressure, frequent infections, loss of kidney function, nerve damage, heart and blood vessel disease, gangrene, and ulcers (e.g., in an extremity).

Slow-healing or non-healing wounds commonly occur in diabetics. A wound includes an open wound or a closed wound. For example, an open wound occurs due to an injury to the skin, where the skin is cut, punctured, or torn. Open wounds include incisions, lacerations, abrasions, avulsions, puncture wounds, and penetration wounds. In closed wounds, the skin is not cut, punctured, or torn, but tissue under the skin is injured, e.g., from blunt force trauma. Close wounds include contusions (e.g., bruises), hematomas (e.g., caused by damage to a blood vessel that causes blood to pool under the skin), and crush injuries (e.g., caused by a large amount of force applied to a site of the body over an extended period of time).

One of the most significant complications of diabetes is chronic, non-healing wounds of an extremity, such as a foot. Due to nerve damage in the feet and legs of diabetics, small wounds/irritations often develop into chronic, non-healing wounds without the patient's awareness. Also, because of the damaged microvasculature of diabetics, such wounds take a long time to heal, if at all. A significant percentage of diabetic patients eventually develop foot ulcers, which lead to amputations if not aggressively treated. The present invention provides a method to treat diabetic wounds and/or ulcers, e.g., in an extremity, by using fibroblasts.

A fibroblast is a type of cell of connective tissue that produces collagen and the extracellular matrix (e.g., extracellular matrix proteins such as collagen, glycosaminoglycan, reticular and elastic fiber, and other glycoproteins), which serve a structural role for animal tissues. Fibroblasts are important in the process of wound healing, and tissue damage stimulates the proliferation of fibroblasts.

The process of wound healing comprises several phases: hemostasis, inflammation, proliferation, and remodeling. Upon injury (e.g., to the skin), platelets aggregate at the site of injury to from a clot in order to reduce bleeding. This process is called hemostasis. In the inflammation phase, white blood cells remove bacteria and cell debris from the wound. In the proliferation phase, angiogenesis (formation of new blood vessels by vascular endothelial cells) occurs, as does collagen deposition, tissue formation, epithelialization, and wound contraction at the site of the wound. To form tissue at the site of the wound, fibroblasts grow to form a new extracellular matrix by secreting proteins such as fibronectin and collagen. Re-epithelialization also occurs in which epithelial cells proliferate and cover the site of the wound in order to cover the newly formed tissue. In order to cause wound contraction, myofibroblasts decrease the size of the wound by contracting and bringing in the edges of the wound. In the remodeling phase, apoptosis occurs to remove unnecessary cells at the site of the wound. One or more of these phases in the process of wound healing is disrupted or delayed in non-healing/slow-healing wounds, e.g., due to diabetes, old age, or infections.

In some embodiments, the fibroblast is derived from the site of the wound or a site adjacent to the wound. For example, at least 5% (e.g., at least 10%, 15%, 20%, 25%, 30%, 35%, 40%, 45%, 50%, 55%, 60%, 65%, 70%, 75%, 80%, 85%, 90%, 95%, 99%, or more) of the fibroblasts in the population are derived from the site of the wound or a site adjacent to the wound.

In some cases, the population of fibroblasts comprises a fibroblast that is derived from a portion of the skin of the subject. For example, at least 5% (e.g., at least 10%, 15%, 20%, 25%, 30%, 35%, 40%, 45%, 50%, 55%, 60%, 65%, 70%, 75%, 80%, 85%, 90%, 95%, 99%, or more) of the fibroblasts in the population are derived from a portion of the skin of the subject. In some cases, the population of fibroblasts further comprises a fibroblast that is derived from healthy subject, e.g., a subject not suffering from diabetes. For example, the fibroblast is derived from the skin of the healthy subject. In addition or alternatively, the population of fibroblasts comprises a fibroblast that is derived from a subject (e.g., healthy or diseased subject) where the fibroblast is derived from a non-diseased or non-injured site on the body of the subject (e.g., from a site on the skin of the subject, where the site is not adjacent to a wound).

The subject is a mammal, e.g., a human, primate, monkey, cow, horse, pig, dog, cat, mouse, rabbit, or rat. Preferably, the subject is a human.

In some cases, the population of fibroblasts includes fibroblasts that have been cultured in vitro. For example, the population of fibroblasts includes at least 5% (e.g., at least 10%, 15%, 20%, 25%, 30%, 35%, 40%, 45%, 50%, 55%, 60%, 65%, 70%, 75%, 80%, 85%, 90%, 95%, 99%, or more) fibroblasts that have been cultured in vitro.

For example, fibroblasts are isolated from a mammalian tissue, such as skin. Fibroblasts are separated from other cell types using conventional cell fractionation methods commonly known in the art. For example, cells are fractionated using a density gradient separation or using flow cytometry sorting. The isolated cells are at least 70% (e.g., at least 70%, 75%, 80%, 85%, 90%, 95%, or 99%) fibroblasts. The isolated cells are plated in a cell culture dish or flask at a density of from $10^3$ to $10^9$ cells per mL of culture. The cells are then cultured in standard culture media suitable for the culture of fibroblasts, e.g., IMDM, MEM, DMEM, RPMI 1640, Alpha Medium, or McCoy's Medium. The culture media optionally contains a serum component, e.g., horse, human, fetal calf, newborn calf, or calf serum. Cells are cultured for 2, 4, 6, 8, 10, 12, 14, 16, 18, 20, or more days. For example, the cells are cultured for less than 12 days. Standard culture schedules call for medium and serum to be exchanged weekly, either as a single exchange performed weekly or a one-half medium and serum exchange performed twice weekly. Preferably, the nutrient medium of the culture is replaced, preferably perfused, either continuously or periodically, at a rate of about 1 ml per ml of culture per about 24 to about 48 hour period, for cells cultured at a density of from $2\times10^6$ to $1\times10^7$ cells per ml. After culturing, the cells are harvested, for example using an enzyme such as trypsin, and washed to remove the growth medium. The cells are resuspended in a pharmaceutical grade electrolyte solution, for example Isolyte (B. Braun Medical Inc., Bethlehem, Pa.) and optionally supplemented with serum albumin.

In some embodiments, the population of fibroblasts includes a fibroblast with metabolic memory, e.g., associated with an epigenetic alteration, compared to a fibroblast derived from a subject not suffering from diabetes and/or not having a wound.

In some embodiments, a fibroblast is epigenetically altered at one or more target sites (e.g., genes) shown in Table 1 below. For example, the fibroblast (e.g., diabetic foot ulcer (DFU) fibroblast) contains an alteration (e.g., methylation) in one or more of the genes shown in Table 1 below compared to non-diabetic fibroblasts (NFF). In other examples, the fibroblast (e.g., diabetic foot ulcer (DFU) fibroblast) contains an increase or decrease (e.g., by at least 2-fold, 3-fold, 4-fold, 5-fold, 10-fold, or greater) in methylation of one or more of the genes shown in Table 1 below compared to non-diabetic fibroblasts (NFF) and/or in methylation of one or more site within a gene shown in Table 1 compared to non-diabetic fibroblasts. For example, the fibroblast (e.g., diabetic foot ulcer (DFU) fibroblast) contains an increase or decrease by at least 2-fold in methylation of one or more of the genes shown in Table 1 below compared to non-diabetic fibroblasts (NFF) and/or in methylation of one or more site within a gene shown in Table 1 compared to non-diabetic fibroblasts. Differential methylation is determined using methods commonly available in the art, e.g., methylation assays available from Illumina, bisulfite sequencing, and/or pyrosequencing. See, e.g., Weisenberger et al. "Comprehensive DNA Methylation Analysis on the Illumina® Infinium® Assay Platform." Illumina, Inc. Mar. 25, 2008. Web. May 9, 2014. res.illumina.com/documents/products/appnotes/appnote_dna_methylation_analysis_infinium.pdf To generate the information in Table 1, an Illumina-style annotation method was used. Differentially methylated probes were used to identify those sites in a gene/chromosome that contained altered methylation in DFU vs. NFF. The table below lists these differentially methylated sites and provides information regarding the functions of these sites/areas of the chromosome based on previous observations and classifications. These functions are useful for interpreting the role of (e.g., biological pathways affected by or disease states associated with) the differential methylation observed in NFF v. DFU.

The beta.median value was calculated as the median of beta across the 4 biological replicate samples in the NFF and DFU groups, respectively. Beta was calculated as beta=M/(M+U+alpha), where M is the values of the methylated probe and U is the value of the unmethylated probe and alpha is an arbitrary offset of 100. The M and U values were converted from fluorescence readings on the array.

UCSC_CpG_Islands_Name indicates the chromosomal location of a CpG island as defined by the University of California Southern California database (UCSC). If the single nucleotide interrogated by the differentially methylated probe fell within this region of the CpG island, then it was considered to be annotated to this CpG island.

The Phantom column refers to whether the differentially methylated probe fell within a promoter as defined by the FANTOM (Functional Annotation of the Mammalian genome) algorithm. See, e.g., Katayama et al. Brief Bioinform. 5.3(2004):249-258, incorporated herein by reference.

DMR refers to a differentially methylated region. The DMR column indicates whether this site has been identified to be differentially methylated in other experiments as interpreted by a consortium of epigenetics experts assembled by Illumina. This information may be from different cell types and biological contexts. The DMR information could shed light into whether this particular site is prone to methylation differences. RDMR refers to a reprogramming-specific DMR, CDMR refers to a cancer DMR, and DMR refers a differentially methylated region that is not further classified.3

The Enhancer column indicates whether this region is determined to be an enhancer of gene expression as determined by bioinformatic methods according to a consortium of epigenetics experts assembled by Illumina. TRUE means that this region has been identified as an enhancer.

The HMM_Island indicates whether the site containing the differentially methylated probe is identified as a CpG island using the hidden markov model algorithm. See, e.g., Yoon. Curr. Genomics. 10.6(2009):402-415, incorporated herein by reference. This column provides similar information as the UCSC_CpG_Island column and overall offers insight into the genomic context and potential regulatory roles of DNA methylation at this site.

The Regulatory_Feature_Name and Regulatory_Feature_Group columns provide information regarding the gene expression regulatory features of the differentially methylated site as described by the consortium of epigenetics experts assembled by Illumina. This information is useful for interpreting the regulatory roles of the sites that are differentially methylated between DFU v. NFF.

DHS refers to DNase I hypersensitive sites, and TRUE within the DHS column means that the differentially methylated probe fell within an identified DHS site. This information is useful for elucidating the potential regulatory roles of DNA methylation at this site, as methylation within accessible DHS sites may regulate gene expression.

Throughout Table 1, NA means Not Applicable because this specific category is not representative of the context of that specific differentially methylate probe site.

TABLE 1

Differential methylation of genes in DFU versus NFF using an Illumina-style annotation method

| Name | chr | NFF. beta. median | DFU. beta. median | UCSC_ RefGene_ Name | UCSC_ RefGene_ Accession | UCSC_ RefGene_ Group | UCSC_ CpG_ Islands_ Name | Relation_ to_UCSC_ CpG_Island |
|---|---|---|---|---|---|---|---|---|
| cg00156230 | chr7:45073692 | 0.3 | 0.54 | CCM2; CCM2; CCM2; CCM2; CCM2 | NM_031443; NM_001029835; NM_001167935; NM_001167934; NR_030770 | Body; Body; Body; Body; Body | NA | NA |
| cg00264799 | chr12:102848839 | 0.74 | 0.41 | IGF1; IGF1; IGF1; IGF1 | NM_001111285; NM_000618; NM_001111283; NM_001111284 | Body; Body; Body; Body | NA | NA |
| cg00290607 | chr11:67383545 | 0.54 | 0.31 | NA | NA | NA | chr11:67383537-67383809 | Island |
| cg00481216 | chr2:181971175 | 0.44 | 0.66 | NA | NA | NA | NA | NA |
| cg00518941 | chr2:46361964 | 0.53 | 0.74 | PRKCE | NM_005400 | Body | NA | NA |
| cg00575645 | chr5:169548502 | 0.72 | 0.51 | NA | NA | NA | NA | NA |
| cg00806704 | chr13:28539042 | 0.57 | 0.33 | CDX2 | NM_001265 | Body | chr13:28540356-28541279 | N_Shore |
| cg00945409 | chr10:80737665 | 0.81 | 0.45 | LOC283050; LOC283050; LOC283050 | NR_024431; NR_024429; NR_015429 | Body; Body; Body | chr10:80733751-80734013 | S_Shelf |
| cg01230320 | chr2:19549980 | 0.91 | 0.59 | NA | NA | NA | chr2:19551735-19551961 | N_Shore |
| cg01395541 | chr6:34524766 | 0.77 | 0.57 | SPDEF | NM_012391 | TSS1500 | NA | NA |
| cg01468567 | chr19:49843922 | 0.48 | 0.7 | TEAD2 | NM_003598 | 3'UTR | chr19:49842018-49842323 | S_Shore |
| cg01470456 | chr8:85787158 | 0.86 | 0.63 | RALYL; RALYL; RALYL; RALYL | NM_001100393; NM_001100392; NM_001100391; NM_173848 | Body; Body; Body; Body | NA | NA |
| cg01549977 | chr14:65743867 | 0.73 | 0.47 | NA | NA | NA | chr14:65746329-65746972 | N_Shelf |
| cg01632562 | chr6:45629759 | 0.5 | 0.28 | NA | NA | NA | chr6:45630986-45631814 | N_Shore |
| cg01694488 | chr4:1580172 | 0.14 | 0.39 | NA | NA | NA | chr4:1580050-1580455 | Island |

TABLE 1-continued

Differential methylation of genes in DFU versus NFF using an Illumina-style annotation method

| | | | | | | | | |
|---|---|---|---|---|---|---|---|---|
| cg01790920 | chr5:3594679 | 0.49 | 0.25 | IRX1 | NM_024337 | TSS1500 | chr5:3594467-3603054 | Island |
| cg02100397 | chr19:646890 | 0.88 | 0.53 | NA | NA | NA | chr19:645890-648623 | Island |
| cg02138953 | chr10:75666279 | 0.64 | 0.35 | NA | NA | NA | NA | NA |
| cg02159489 | chr17:79459563 | 0.09 | 0.5 | NA | NA | NA | chr17:79454734-79455823 | S_Shelf |
| cg02197634 | chr6:33048875 | 0.19 | 0.47 | HLA-DPB1 | NM_002121 | Body | chr6:33048416-33048814 | S_Shore |
| cg02368820 | chr1:3052501 | 0.27 | 0.66 | PRDM16; PRDM16 | NM_022114; NM_199454 | Body; Body | NA | NA |
| cg02395396 | chr1:52435307 | 0.57 | 0.34 | RAB3B | NM_002867 | Body | NA | NA |
| cg02527375 | chr3:41724686 | 0.66 | 0.39 | ULK4 | NM_017886 | Body | NA | NA |
| cg02532518 | chr16:3210066 | 0.56 | 0.34 | NA | NA | NA | chr16:3207597-3209413 | S_Shore |
| cg02799905 | chr2:206342226 | 0.68 | 0.45 | PARD3B; PARD3B; PARD3B | NM_152526; NM_057177; NM_205863 | Body; Body; Body | NA | NA |
| cg02890259 | chr1:16345207 | 0.09 | 0.46 | HSPB7; HSPB7 | NM_014424; NM_014424 | 1stExon; 5'UTR | NA | NA |
| cg03079497 | chr17:1390554 | 0.14 | 0.35 | MYO1C; MYO1C | NM_03375; NM_001080779 | 5'UTR; Body | chr17:1390456-1390786 | Island |
| cg03088219 | chr4:176711190 | 0.57 | 0.32 | GPM6A; GPM6A; GPM6A | NM_201591; NM_005277; NM_201592 | Body; Body; Body | NA | NA |
| cg03119829 | chr1:64170964 | 0.42 | 0.69 | NA | NA | NA | NA | NA |
| cg03217995 | chr7:27203430 | 0.36 | 0.58 | HOXA9 | NM_152739 | Body | chr7:27203915-27206462 | N_Shore |
| cg03301058 | chr6:90007856 | 0.6 | 0.34 | GABRR2 | NM_002043 | Body | NA | NA |
| cg03487027 | chr10:77159055 | 0.3 | 0.72 | ZNF503 | NM_032772 | Body | chr10:77155128-77169600 | Island |
| cg03653601 | chr16:16156039 | 0.36 | 0.65 | ABCC1; ABCC1; ABCC1; ABCC1; ABCC1 | NM_019862; NM_019898; NM_019899; NM_004996; NM_019900 | Body; Body; Body; Body; Body | NA | NA |
| cg03814093 | chr4:154410006 | 0.45 | 0.65 | KIAA0922; KIAA0922 | NM_015196; NM_001131007 | Body; Body | NA | NA |
| cg03859028 | chr15:99949289 | 0.17 | 0.4 | NA | NA | NA | NA | NA |
| cg04478875 | chr5:142023774 | 0.67 | 0.4 | FGF1; FGF1; FGF1; FGF1; FGF1; FGF1 | NM_000800; NM_033136; NM_001144935; NM_001144934; NR_026696; NR_026695 | 5'UTR; 5'UTR; 5'UTR; 5'UTR; Body; Body | NA | NA |
| cg04500819 | chr1:170376975 | 0.81 | 0.5 | NA | NA | NA | NA | NA |
| cg04506342 | chr2:160463692 | 0.42 | 0.85 | BAZ2B | NM_013450 | 5'UTR | NA | NA |
| cg04887066 | chr12:32185731 | 0.57 | 0.31 | NA | NA | NA | NA | NA |
| cg04888234 | chr1:161675579 | 0.85 | 0.48 | FCRLA | NM_032738 | TSS1500 | NA | NA |
| cg04894537 | chr11:2763171 | 0.41 | 0.2 | KCNQ1; KCNQ1 | NM_000218; NM_181798 | Body; Body | NA | NA |
| cg04998634 | chr19:1857004 | 0.13 | 0.39 | KLF16 | NM_031918 | Body | chr19:1856725-1857443 | Island |
| cg05210689 | chr14:100233454 | 0.55 | 0.26 | NA | NA | NA | NA | NA |
| cg05227215 | chr5:139057496 | 0.24 | 0.47 | CXXC5 | NM_016463 | 5'UTR | chr5:139056577-139056856 | S_Shore |
| cg05276972 | chr11:130482015 | 0.82 | 0.43 | NA | NA | NA | NA | NA |
| cg05279330 | chr13:26776254 | 0.9 | 0.65 | NA | NA | NA | NA | NA |
| cg05422883 | chr2:43072932 | 0.42 | 0.65 | NA | NA | NA | NA | NA |
| cg05424060 | chr7:79768675 | 0.4 | 0.63 | GNAI1 | NM_002069 | Body | chr7:79763793-79764889 | S_Shelf |
| cg05494467 | chr5:140892308 | 0.12 | 0.33 | PCDHGB5; PCDHGC3; PCDHGA6; PCDHGB4; PCDHGA8; PCDHGA12; PCDHGB3; PCDHGA5; PCDHGA1; PCDHGA11; PCDHGA3; PCDHGA2; PCDHGB6; PCDHGA11; PCDHGC5; PCDHGA4; PCDHGB2; | NM_018925; NM_002588; NM_018919; NM_003736; NM_032088; NM_003735; NM_018924; NM_018918; NM_018912; NM_032092; NM_018916; NM_018915; NM_018926; NM_018914; NM_018929; NM_018917; NM_018923; | 3'UTR; 3'UTR; 3'UTR; 3'UTR; 3'UTR; 3'UTR; 3'UTR; 3'UTR; 3'UTR; 3'UTR; 3'UTR; 3'UTR; 3'UTR; 3'UTR; 3'UTR; 3'UTR; 3'UTR; | chr5:140892913-140893189 | N_Shore |

TABLE 1-continued

Differential methylation of genes in DFU versus NFF using an Illumina-style annotation method

| | | | | | | | | |
|---|---|---|---|---|---|---|---|---|
| | | | | | PCDHGA10; | NM_018913; | 3'UTR; | |
| | | | | | PCDHGC4; | NM_018928; | 3'UTR; | |
| | | | | | PCDHGB7; | NM_018927; | 3'UTR; | |
| | | | | | PCDHGA9; | NM_018921; | 3'UTR; | |
| | | | | | PCDHGC3; | NM_032403; | 3'UTR; | |
| | | | | | PCDHGB1; | NM_018922; | 3'UTR; | |
| | | | | | PCDHGA7 | NM_018920 | 3'UTR | |
| cg05508296 | chr5:1016460 | 0.24 | 0.55 | NKD2 | NM_033120 | Body | NA | NA |
| cg05633070 | chr17:933118 | 0.52 | 0.78 | ABR; | NM_021962; | Body; | chr17:933026- | Island |
| | | | | ABR; | NM_001092; | Body; | 933236 | |
| | | | | ABR | NM_001159746 | Body | | |
| cg05810177 | chr7:134050402 | 0.49 | 0.2 | NA | NA | NA | NA | NA |
| cg05824218 | chr17:38499096 | 0.49 | 0.7 | RARA; | NM_001024809; | 1stExon; | chr17:38497527- | S_Shore |
| | | | | RARA; | NM_001145301; | Body; | 38498963 | |
| | | | | RARA; | NM_000964; | Body; | | |
| | | | | RARA | NM_001145302 | Body | | |
| cg05938207 | chr6:32489750 | 0.51 | 0.29 | HLA-DRB5 | NM_002125 | Body | chr6:32489742-32490128 | Island |
| cg05949913 | chr6:132557557 | 0.65 | 0.42 | NA | NA | NA | NA | NA |
| cg06486129 | chr21:45573410 | 0.14 | 0.36 | NA | NA | NA | chr21:45575451-45575833 | N_Shelf |
| cg06493806 | chr18:77278806 | 0.89 | 0.57 | NFATC1; | NM_006162; | Body; | chr18:77280144-77280414 | N_Shore |
| | | | | NFATC1; | NM_172388; | Body; | | |
| | | | | NFATC1; | NM_172389; | Body; | | |
| | | | | NFATC1 | NM_172387 | Body | | |
| cg06620723 | chr1:12404945 | 0.41 | 0.68 | VPS13D; | NM_015378; | Body; | NA | NA |
| | | | | VPS13D | NM_018156 | Body | | |
| cg06766860 | chr12:132863983 | 0.44 | 0.66 | GALNT9 | NM_001122636 | Body | chr12:132865236-132865506 | N_Shore |
| cg06844165 | chr17:3768599 | 0.84 | 0.57 | CAMKK1; | NM_172206; | Body; | chr17:3769663-3769874 | N_Shore |
| | | | | CAMKK1; | NM_032294; | Body; | | |
| | | | | CAMKK1 | NM_172207 | 3'UTR | | |
| cg06871529 | chr13:32700732 | 0.8 | 0.6 | FRY | NM_023037 | Body | NA | NA |
| cg07030794 | chr17:72589110 | 0.78 | 0.57 | CD300LD; | NM_001115152; | TSS1500; | NA | NA |
| | | | | C17orf77 | NM_152460 | 3'UTR | | |
| cg07525313 | chr6:116262856 | 0.57 | 0.78 | FRK | NM_002031 | 3'UTR | NA | NA |
| cg07857040 | chr16:1582219 | 0.33 | 0.54 | IFT140 | NM_014714 | Body | chr16:1583809-1584641 | N_Shore |
| cg07891658 | chr16:87996731 | 0.27 | 0.55 | BANP; | NM_017869; | 5'UTR; | NA | NA |
| | | | | BANP | NM_079837 | 5'UTR | | |
| cg07943832 | chr6:155568918 | 0.74 | 0.44 | TIAM2; | NM_012454; | Body; | NA | NA |
| | | | | TIAM2 | NM_001010927 | Body | | |
| cg08161142 | chr13:24273617 | 0.39 | 0.65 | NA | NA | NA | chr13:24269499-24270116 | S_Shelf |
| cg08233148 | chr17:81047721 | 0.81 | 0.53 | METRNL | NM_001004431 | Body | chr17:81047515-81047965 | Island |
| cg08365687 | chr3:52569147 | 0.33 | 0.53 | NT5DC2; | NM_022908; | TSS200; | chr3:52570475-52570842 | N_Shore |
| | | | | NT5DC2; | NM_001134231; | TSS1500; | | |
| | | | | LOC440957 | NM_001124767 | TSS1500 | | |
| cg08797704 | chr16:65692605 | 0.45 | 0.16 | NA | NA | NA | NA | NA |
| cg09259081 | chr16:84538889 | 0.32 | 0.55 | KIAA1609 | NM_020947 | TSS1500 | chr16:84538884-84539115 | Island |
| cg09592546 | chr17:78652902 | 0.58 | 0.88 | RPTOR; | NM_001163034; | Body; | NA | NA |
| | | | | RPTOR | NM_020761 | Body | | |
| cg09663736 | chr11:131554122 | 0.75 | 0.36 | NTM | NM_001048209 | Body | NA | NA |
| cg09949775 | chr19:18902107 | 0.1 | 0.33 | COMP; | NM_000095; | 1stExon; | chr19:18899037-18902284 | Island |
| | | | | COMP | NM_000095 | 5'UTR | | |
| cg10167378 | chr1:228756711 | 0.85 | 0.59 | NA | NA | NA | chr1:228744110-228784168 | Island |
| cg10270430 | chr6:34024362 | 0.19 | 0.4 | GRM4 | NM_000841 | Body | chr6:34024201-34024457 | Island |
| cg10332003 | chr4:185070366 | 0.66 | 0.44 | ENPP6 | NM_153343 | Body | NA | NA |
| cg10590622 | chr4:96760945 | 0.61 | 0.14 | PDHA2 | NM_005390 | TSS1500 | NA | NA |
| cg10776061 | chr19:12768390 | 0.54 | 0.29 | MAN2B1 | NM_000528 | Body | chr19:12767749-12767980 | S_Shore |
| cg11035303 | chr3:43465503 | 0.32 | 0.06 | ANO10 | NM_018075 | Body | NA | NA |
| cg11317459 | chr13:21872234 | 0.08 | 0.34 | NA | NA | NA | chr13:21872179-21872665 | Island |
| cg11639130 | chr12:131303478 | 0.5 | 0.72 | STX2; | NM_001980; | Body; | chr12:131303093-131303836 | Island |
| | | | | STX2 | NM_194356 | Body | | |
| cg11728145 | chr2:1658190 | 0.72 | 0.43 | PXDN | NM_012293 | Body | NA | NA |
| cg11728747 | chr7:29037910 | 0.29 | 0.5 | CPVL; | NM_031311; | Body; | NA | NA |
| | | | | CPVL | NM_019029 | Body | | |
| cg11791078 | chr5:36273196 | 0.89 | 0.43 | RANBP3L; | NM_145000; | Body; | NA | NA |
| | | | | RANBP3L | NM_001161429 | Body | | |
| cg11986643 | chr6:32634316 | 0.51 | 0.29 | HLA-DQB1 | NM_002123 | 1stExon | chr6:32632158-32633027 | S_Shore |
| cg12214399 | chr4:53210660 | 0.14 | 0.55 | NA | NA | NA | NA | NA |

TABLE 1-continued

Differential methylation of genes in DFU versus NFF using an Illumina-style annotation method

| Probe | Location | | | Gene | Accession | Region | CpG coords | Relation |
|---|---|---|---|---|---|---|---|---|
| cg12293347 | chr8:1117672 | 0.74 | 0.48 | NA | NA | NA | chr8:1113058-1114073 | S_Shelf |
| cg12360123 | chr10:79984532 | 0.56 | 0.35 | NA | NA | NA | NA | NA |
| cg12734688 | chr1:48308390 | 0.53 | 0.32 | NA | NA | NA | NA | NA |
| cg12743416 | chr7:138229989 | 0.28 | 0.64 | TRIM24; TRIM24 | NM_003852; NM_015905 | Body; Body | NA | NA |
| cg12823953 | chr3:137893743 | 0.12 | 0.34 | DBR1; DBR1 | NM_016216; NM_016216 | 1stExon; 5'UTR | chr3:137893410-137893808 | Island |
| cg13038618 | chr14:77467391 | 0.37 | 0.6 | NA | NA | NA | NA | NA |
| cg13205848 | chr12:5675505 | 0.74 | 0.52 | ANO2 | NM_020373 | Body | NA | NA |
| cg13422830 | chr1:19985666 | 0.32 | 0.67 | NA | NA | NA | NA | NA |
| cg13506281 | chr13:29914200 | 0.55 | 0.83 | MTUS2 | NM_001033602 | Body | chr13:29913886-29914301 | Island |
| cg13617837 | chr6:3724690 | 0.34 | 0.54 | C6orf145 | NM_183373 | Body | NA | NA |
| cg13730219 | chr13:21896301 | 0.54 | 0.12 | NA | NA | NA | chr13:21894085-21894606 | S_Shore |
| cg13749548 | chr14:75722495 | 0.66 | 0.23 | NA | NA | NA | chr14:75725748-75726029 | N_Shelf |
| cg13943068 | chr4:1580193 | 0.11 | 0.49 | NA | NA | NA | chr4:1580050-1580455 | Island |
| cg14173968 | chr6:39740405 | 0.58 | 0.78 | NA | NA | NA | NA | NA |
| cg14223671 | chr16:857981 | 0.08 | 0.29 | PRR25 | NM_001013638 | Body | chr16:857341-858025 | Island |
| cg14447606 | chr2:72370328 | 0.11 | 0.44 | CYP26B1 | NM_019885 | Body | chr2:72370296-72370682 | Island |
| cg14456004 | chr13:21872349 | 0.14 | 0.45 | NA | NA | NA | chr13:21872179-21872665 | Island |
| cg14463164 | chr9:109715708 | 0.85 | 0.54 | ZNF462; MIR548Q | NM_021224; NR_031752 | Body; Body | NA | NA |
| cg14646613 | chr9:110412708 | 0.78 | 0.39 | NA | NA | NA | NA | NA |
| cg14651435 | chr7:157209551 | 0.96 | 0.68 | DNAJB6 | NM_058246 | 3'UTR | chr7:157208794-157209008 | S_Shore |
| cg14852082 | chr4:1580132 | 0.25 | 0.49 | NA | NA | NA | chr4:1580050-1580455 | Island |
| cg14895374 | chr8:28930481 | 0.71 | 0.42 | KIF13B | NM_015254 | Body | chr8:28928996-28929718 | S_Shore |
| cg15260248 | chr3:189829092 | 0.64 | 0.85 | LEPREL1; LEPREL1 | NM_001134418; NM_018192 | 5'UTR; Body | NA | NA |
| cg15497834 | chr20:48998834 | 0.37 | 0.61 | NA | NA | NA | NA | NA |
| cg15690379 | chr3:52683739 | 0.57 | 0.36 | PBRM1; PBRM1; PBRM1 | NM_181042; NM_018313; NM_018165 | Body; Body; Body | NA | NA |
| cg15752756 | chr6:32634481 | 0.45 | 0.17 | HLA-DQB1 | NM_002123 | TSS200 | chr6:32632158-32633027 | S_Shore |
| cg15878909 | chr12:8380286 | 0.58 | 0.32 | FAM90A1 | NM_018088 | TSS200 | NA | NA |
| cg16081854 | chr5:308268 | 0.8 | 0.07 | AHRR; PDCD6 | NM_020731; NM_013232 | Body; Body | chr5:309705-310136 | N_Shore |
| cg16112880 | chr1:201123745 | 0.14 | 0.67 | TMEM9 | NM_016456 | TSS200 | chr1:201123245-201123746 | Island |
| cg16463697 | chr2:223886480 | 0.33 | 0.73 | NA | NA | NA | NA | NA |
| cg16508714 | chr10:98425110 | 0.68 | 0.46 | PIK3AP1 | NM_152309 | Body | NA | NA |
| cg16540391 | chr6:151042035 | 0.48 | 0.28 | PLEKHG1 | NM_001029884 | 5'UTR | NA | NA |
| cg16664523 | chr5:67586170 | 0.33 | 0.53 | PIK3R1; PIK3R1; PIK3R1 | NM_181523; NM_181504; NM_181524 | Body; TSS1500; Body | chr5:67584213-67584451 | S_Shore |
| cg17013691 | chr5:14380323 | 0.83 | 0.62 | TRIO | NM_007118 | Body | NA | NA |
| cg17171539 | chr1:59398690 | 0.7 | 0.49 | NA | NA | NA | NA | NA |
| cg17449954 | chr1:40105667 | 0.15 | 0.4 | HEYL | NM_014571 | TSS1500 | chr1:40105010-40105707 | Island |
| cg17602481 | chr13:114890515 | 0.89 | 0.59 | RASA3 | NM_007368 | Body | NA | NA |
| cg17662493 | chr22:45806309 | 0.65 | 0.88 | SMC1B | NM_148674 | Body | chr22:45809191-45809953 | N_Shelf |
| cg17811452 | chr20:44007674 | 0.71 | 0.45 | TP53TG5; SYS1-DBNDD2 | NM_014477; NR_003189 | TSS1500; Body | NA | NA |
| cg18004235 | chr2:19808330 | 0.73 | 0.49 | NA | NA | NA | NA | NA |
| cg18009021 | chr4:95376488 | 0.75 | 0.44 | PDLIM5; PDLIM5; PDLIM5; PDLIM5 | NR_024179; NM_001011515; NM_006457; NM_001011516; NM_001011513 | Body; Body; Body; Body; Body | chr4:95372801-95373535 | S_Shelf |
| cg18149745 | chr3:197094595 | 0.77 | 0.49 | NA | NA | NA | NA | NA |
| cg18235100 | chr4:81124600 | 0.43 | 0.65 | PRDM8; PRDM8 | NM_001099403; NM_020226 | Body; Body | chr4:81124468-81124845 | Island |
| cg18302225 | chr5:55776401 | 0.23 | 0.55 | NA | NA | NA | chr5:55776604-55777233 | N_Shore |
| cg18332838 | chr8:126698738 | 0.47 | 0.27 | NA | NA | NA | NA | NA |
| cg18379295 | chr14:52326155 | 0.29 | 0.6 | GNG2 | NM_053064 | TSS1500 | NA | NA |

TABLE 1-continued

Differential methylation of genes in DFU versus NFF using an Illumina-style annotation method

| | | | | | | | | |
|---|---|---|---|---|---|---|---|---|
| cg18438894 | chr1:184377525 | 0.61 | 0.4 | C1orf21 | NM_030806 | 5'UTR | NA | NA |
| cg18642369 | chr13:99651231 | 0.37 | 0.64 | DOCK9; DOCK9 | NM_015296; NM_001130049 | Body; Body | NA | NA |
| cg19141316 | chr11:19750209 | 0.83 | 0.59 | NAV2; NAV2; NAV2 | NM_182964; NM_001111018; NM_145117 | Body; Body; Body | NA | NA |
| cg19243721 | chr6:166851830 | 0.37 | 0.83 | RPS6KA2; RPS6KA2 | NM_021135; NM_001006932 | Body; Body | NA | NA |
| cg19264571 | chr18:10454085 | 0.26 | 0.47 | APCDD1 | NM_153000 | TSS1500 | chr18:10454082-10454296 | Island |
| cg19300401 | chr6:16962712 | 0.39 | 0.81 | NA | NA | NA | NA | NA |
| cg19539986 | chr14:35032169 | 0.9 | 0.65 | SNX6; SNX6 | NM_021249; NM_152233 | 3'UTR; 3'UTR | NA | NA |
| cg19577074 | chr4:152405174 | 0.32 | 0.53 | FAM160A1 | NM_001109977 | 5'UTR | NA | NA |
| cg19697575 | chr2:172374119 | 0.57 | 0.87 | NA | NA | NA | chr2:172373817-172374199 | Island |
| cg19717773 | chr7:2847554 | 0.26 | 0.5 | GNA12 | NM_007353 | Body | NA | NA |
| cg19799454 | chr7:64328759 | 0.82 | 0.57 | NA | NA | NA | NA | NA |
| cg19907305 | chr19:18902117 | 0.12 | 0.34 | COMP | NM_000095 | TSS200 | chr19:18899037-18902284 | Island |
| cg20274462 | chr8:95980625 | 0.71 | 0.5 | NA | NA | NA | NA | NA |
| cg20321086 | chr8:62052207 | 0.47 | 0.25 | NA | NA | NA | chr8:62051646-62052431 | Island |
| cg20346503 | chr2:128994402 | 0.46 | 0.24 | NA | NA | NA | chr2:128990509-128991325 | S_Shelf |
| cg20539283 | chr2:162932048 | 0.78 | 0.47 | DPP4 | NM_001935 | TSS1500 | chr2:162930233-162930879 | S_Shore |
| cg20895691 | chr2:23641550 | 0.54 | 0.26 | KLHL29 | NM_052920 | 5'UTR | NA | NA |
| cg20976286 | chr15:28054345 | 0.59 | 0.11 | OCA2 | NM_000275 | Body | chr15:28050250-28050789 | S_Shelf |
| cg21211688 | chr9:136403935 | 0.81 | 0.34 | ADAMTSL2; ADAMTSL2 | NM_014694; NM_001145320 | Body; Body | chr9:136399367-136400274 | S_Shelf |
| cg21332500 | chr7:27233480 | 0.16 | 0.37 | NA | NA | NA | chr7:27231805-27233097 | S_Shore |
| cg21446981 | chr7:37534909 | 0.49 | 0.23 | NA | NA | NA | NA | NA |
| cg21498547 | chr8:1651128 | 0.1 | 0.62 | DLGAP2 | NM_004745 | 3'UTR | chr8:1649439-1649759 | S_Shore |
| cg21565914 | chr2:162931175 | 0.72 | 0.47 | DPP4 | NM_001935 | TSS200 | chr2:162930233-162930879 | S_Shore |
| cg21681643 | chr2:114039512 | 0.9 | 0.66 | LOC440839 | NR_029399 | Body | chr2:114034594-114036041 | S_Shelf |
| cg21860675 | chr3:71586357 | 0.6 | 0.25 | FOXP1; FOXP1 | NM_032682; NM_001012505 | 5'UTR; 5'UTR | NA | NA |
| cg21945639 | chr1:200271342 | 0.39 | 0.14 | NA | NA | NA | chr1:200271276-200271538 | Island |
| cg21964662 | chr13:79234715 | 0.46 | 0.69 | RNF219 | NM_024546 | TSS1500 | chr13:79232822-79233417 | S_Shore |
| cg22031873 | chr4:143765657 | 0.86 | 0.61 | INPP4B; INPP4B | NM_001101669; NM_003866 | 5'UTR; 5'UTR | chr4:143766940-143768413 | N_Shore |
| cg22749855 | chr17:76353952 | 0.5 | 0.29 | SOCS3 | NM_003955 | 3'UTR | chr17:76354818-76357038 | N_Shore |
| cg23052585 | chr10:50328538 | 0.58 | 0.82 | NA | NA | NA | NA | NA |
| cg23159970 | chr12:2690385 | 0.9 | 0.16 | CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C; CACNA1C | NM_001129844; NM_001129827; NM_001129839; NM_001129834; NM_001129841; NM_000719; NM_001129830; NM_001167625; NM_001129843; NM_001167624; NM_001129835; NM_001129837; NM_001167623; NM_001129840; NM_199460; NM_001129833; NM_001129832; NM_001129829; NM_001129846; NM_001129836; NM_001129838; NM_001129831; NM_001129842 | Body; Body; Body; Body; Body; Body; Body; Body; Body; Body; Body; Body; Body; Body; Body; Body; Body; Body; Body; Body; Body; Body; Body | NA | NA |
| cg23192683 | chr3:194208907 | 0.67 | 0.45 | NA | NA | NA | chr3:194207385-194208785 | S_Shore |
| cg23677311 | chr8:25061108 | 0.75 | 0.51 | DOCK5 | NM_024940 | Body | NA | NA |

TABLE 1-continued

Differential methylation of genes in DFU versus NFF using an Illumina-style annotation method

| | | | | | | | | |
|---|---|---|---|---|---|---|---|---|
| cg23698271 | chr10:121346762 | 0.63 | 0.89 | TIAL1; TIAL1 | NM_001033925; NM_003252 | Body; Body | NA | NA |
| cg23763647 | chr10:4868690 | 0.29 | 0.05 | AKR1E2 | NM_001040177 | Body | chr10:4868125-4868949 | Island |
| cg24199384 | chr13:24365000 | 0.57 | 0.34 | MIPEP | NM_005932 | Body | NA | NA |
| cg24284539 | chr10:12999599 | 0.75 | 0.47 | CCDC3 | NM_031455 | Body | NA | NA |
| cg24451872 | chr1:32177995 | 0.4 | 0.16 | NA | NA | NA | chr1:32180131-32180487 | N_Shelf |
| cg24623760 | chr12:123610989 | 0.57 | 0.27 | NA | NA | NA | NA | NA |
| cg25191304 | chr1:42097792 | 0.74 | 0.49 | HIVEP3; HIVEP3 | NM_024503; NM_001127714 | 5'UTR; 5'UTR | NA | NA |
| cg25491704 | chr6:33048879 | 0.32 | 0.64 | HLA-DPB1 | NM_002121 | Body | chr6:33048416-33048814 | S_Shore |
| cg25541928 | chr15:51973199 | 0.71 | 0.48 | SCG3; SCG3 | NM_013243; NM_001165257 | TSS1500; TSS1500 | chr15:51973533-51973838 | N_Shore |
| cg25570222 | chr2:45804631 | 0.66 | 0.91 | SRBD1 | NM_018079 | Body | NA | NA |
| cg25614253 | chr8:143561205 | 0.33 | 0.12 | BAI1 | NM_001702 | Body | chr8:143558487-143558824 | S_Shelf |
| cg25638870 | chr11:89224717 | 0.18 | 0.42 | NOX4; NOX4; NOX4; NOX4 | NM_001143837; NR_026571; NM_016931; NM_001143836 | 5'UTR; TSS200; TSS200; TSS200 | chr11:89224416-89224718 | Island |
| cg25909532 | chr7:158821175 | 0.57 | 0.33 | VIPR2 | NM_003382 | 3'UTR | chr7:158823178-158824316 | N_Shelf |
| cg25929399 | chr17:39597601 | 0.39 | 0.16 | KRT38 | NM_006771 | TSS200 | NA | NA |
| cg26365090 | chr20:42574362 | 0.87 | 0.47 | TOX2; TOX2; TOX2; TOX2 | NM_001098796; NM_001098797; NM_001098798; NM_032883 | 5'UTR; Body; TSS200; 5'UTR | NA | NA |
| cg26646659 | chr5:55776364 | 0.31 | 0.52 | NA | NA | NA | chr5:55776604-55777233 | N_Shore |
| cg26690407 | chr5:5887642 | 0.44 | 0.17 | NA | NA | NA | chr5:5887062-5887528 | S_Shore |
| cg26853458 | chr17:9805074 | 0.24 | 0.49 | RCVRN | NM_002903 | Body | chr17:9808067-9808339 | N_Shelf |
| cg26932889 | chr1:54135470 | 0.28 | 0.49 | GLIS1 | NM_147193 | 5'UTR | NA | NA |
| cg27010076 | chr5:112586110 | 0.72 | 0.38 | MCC; MCC | NM_002387; NM_001085377 | Body; Body | NA | NA |
| cg27031754 | chr5:54185940 | 0.47 | 0.26 | NA | NA | NA | NA | NA |
| cg27065717 | chr16:85608934 | 0.46 | 0.67 | NA | NA | NA | NA | NA |
| cg27286614 | chr7:2050401 | 0.46 | 0.84 | MAD1L1; MAD1L1; MAD1L1 | NM_003550; NM_001013837; NM_001013836 | Body; Body; Body | chr7:2054060-2054386 | N_Shelf |
| cg27333018 | chr19:2897514 | 0.69 | 0.47 | NA | NA | NA | chr19:2900329-2901203 | N_Shelf |

| Name | Phantom | DMR (differentially methylated region) | Enhancer | Hidden Markov Model (HMM)_Island | Regulatory_Feature_Name | Regulatory_Feature_Group | DHS (DNAse I hypersensitive site) |
|---|---|---|---|---|---|---|---|
| cg00156230 | NA | NA | TRUE | NA | NA | NA | NA |
| cg00264799 | NA | NA | TRUE | NA | NA | NA | NA |
| cg00290607 | NA | NA | TRUE | 11: 67140114-67140331 | 11: 67382913-67383979 | Promoter_Associated | NA |
| cg00481216 | NA | NA | TRUE | NA | NA | NA | NA |
| cg00518941 | NA | NA | TRUE | NA | NA | NA | NA |
| cg00575645 | NA | NA | TRUE | NA | NA | NA | NA |
| cg00806704 | NA | NA | NA | NA | NA | NA | NA |
| cg00945409 | low-CpG: 80407669-80407738 | NA | TRUE | NA | NA | NA | TRUE |
| cg01230320 | NA | NA | NA | 2: 19413297-19414688 | 2: 19549091-19550340 | Promoter_Associated | TRUE |
| cg01395541 | NA | NA | NA | NA | NA | NA | NA |
| cg01468567 | NA | NA | TRUE | NA | 19: 49843436-49843948 | Unclassified | NA |
| cg01470456 | NA | NA | TRUE | NA | NA | NA | NA |
| cg01549977 | NA | NA | TRUE | NA | NA | NA | TRUE |
| cg01632562 | NA | NA | NA | NA | NA | NA | NA |
| cg01694488 | NA | NA | NA | 4: 1550144-1550508 | NA | NA | NA |
| cg01790920 | NA | NA | NA | 5: 3647396-3649997 | NA | NA | NA |
| cg02100397 | NA | NA | NA | 19: 596804-598501 | NA | NA | NA |

TABLE 1-continued

Differential methylation of genes in DFU versus NFF using an Illumina-style annotation method

| | | | | | | | |
|---|---|---|---|---|---|---|---|
| cg02138953 | NA | NA | TRUE | NA | NA | NA | NA |
| cg02159489 | NA | NA | NA | 17: 77074036-77074159 | NA | NA | NA |
| cg02197634 | NA | NA | TRUE | NA | NA | NA | NA |
| cg02368820 | NA | NA | NA | 1: 3041863-3042751 | NA | NA | NA |
| cg02395396 | NA | NA | TRUE | NA | NA | NA | TRUE |
| cg02527375 | NA | NA | TRUE | NA | NA | NA | NA |
| cg02532518 | NA | NA | NA | 16: 3149986-3150476 | 16: 3209865-3210112 | Unclassified_Cell_type_specific | NA |
| cg02799905 | NA | NA | TRUE | NA | NA | NA | NA |
| cg02890259 | NA | NA | TRUE | NA | NA | NA | TRUE |
| cg03079497 | NA | NA | NA | 17: 1336914-1337650 | 17: 1390020-1390909 | Unclassified | TRUE |
| cg03088219 | NA | NA | NA | NA | NA | NA | NA |
| cg03119829 | NA | DMR | NA | NA | 1: 64170893-64170969 | Unclassified_Cell_type_specific | NA |
| cg03217995 | NA | DMR | NA | 7: 27169827-27171776 | NA | NA | NA |
| cg03301058 | NA | DMR | TRUE | NA | 6: 90007623-90008148 | Unclassified | TRUE |
| cg03487027 | NA | NA | NA | 10: 76828340-76830392 | 10: 77158878-77159061 | Unclassified_Cell_type_specific | NA |
| cg03653601 | NA | NA | TRUE | NA | 16: 16155825-16156219 | Unclassified_Cell_type_specific | NA |
| cg03814093 | NA | NA | NA | 4: 154629395-154629457 | 4: 154409197-154410467 | Promoter_Associated | NA |
| cg03859028 | NA | NA | TRUE | NA | 15: 99948962-99949571 | Unclassified | TRUE |
| cg04478875 | NA | NA | TRUE | NA | NA | NA | NA |
| cg04500819 | NA | NA | TRUE | NA | NA | NA | NA |
| cg04506342 | NA | NA | TRUE | NA | NA | NA | NA |
| cg04887066 | NA | NA | TRUE | NA | NA | NA | NA |
| cg04888234 | NA | NA | NA | NA | NA | NA | NA |
| cg04894537 | NA | NA | TRUE | NA | NA | NA | TRUE |
| cg04998634 | NA | NA | NA | 19: 1807744-1808443 | 19: 1856867-1857574 | Promoter_Associated | NA |
| cg05210689 | NA | NA | TRUE | NA | NA | NA | TRUE |
| cg05227215 | NA | NA | TRUE | NA | NA | NA | NA |
| cg05276972 | NA | NA | TRUE | NA | NA | NA | TRUE |
| cg05279330 | NA | NA | TRUE | NA | NA | NA | NA |
| cg05422883 | NA | NA | TRUE | NA | NA | NA | NA |
| cg05424060 | NA | NA | NA | NA | NA | NA | NA |
| cg05494467 | NA | CDMR | NA | 5: 140872467-140872619 | 5: 140891341-140892957 | Promoter_Associated | TRUE |
| cg05508296 | NA | NA | NA | 5: 1069176-1069496 | NA | NA | TRUE |
| cg05633070 | NA | NA | TRUE | 17: 879777-879966 | NA | NA | NA |
| cg05810177 | NA | NA | TRUE | NA | NA | NA | NA |
| cg05824218 | NA | NA | NA | 17: 35751130-35752623 | NA | NA | NA |
| cg05938207 | NA | NA | NA | 6: 32597721-32598106 | NA | NA | NA |
| cg05949913 | NA | NA | TRUE | NA | NA | NA | NA |
| cg06486129 | NA | NA | NA | NA | 21: 45573348-45574201 | Unclassified | TRUE |
| cg06493806 | NA | NA | NA | 18: 75379223-75379816 | NA | NA | NA |
| cg06620723 | low-CpG: 12327488-12327568 | NA | NA | NA | 1: 12404910-12405164 | Unclassified_Cell_type_specific | NA |
| cg06766860 | NA | NA | NA | 12: 131374053-131374345 | NA | NA | NA |
| cg06844165 | NA | NA | NA | NA | NA | NA | TRUE |
| cg06871529 | NA | NA | TRUE | NA | NA | NA | NA |
| cg07030794 | NA | NA | NA | NA | NA | NA | NA |
| cg07525313 | NA | NA | NA | NA | NA | NA | NA |
| cg07857040 | NA | NA | NA | 16: 1522055-1522410 | 16: 1582161-1582500 | Unclassified | NA |

TABLE 1-continued

Differential methylation of genes in DFU versus NFF using an Illumina-style annotation method

| | | | | | | | |
|---|---|---|---|---|---|---|---|
| cg07891658 | NA | NA | NA | 16: 86554232-86554374 | 16: 87996629-87997495 | Promoter_Associated_Cell_type_specific | NA |
| cg07943832 | NA | NA | TRUE | NA | 6: 155568903-155570209 | Unclassified | TRUE |
| cg08161142 | NA | NA | NA | NA | NA | NA | NA |
| cg08233148 | NA | NA | NA | 17: 78640438-78641204 | NA | NA | NA |
| cg08365687 | NA | NA | NA | NA | 3: 52569028-52569356 | Unclassified_Cell_type_specific | NA |
| cg08797704 | NA | NA | TRUE | NA | NA | NA | TRUE |
| cg09259081 | NA | NA | NA | 16: 83096386-83096616 | 16: 84537881-84539086 | Promoter_Associated | NA |
| cg09592546 | NA | NA | TRUE | NA | 17: 78652494-78653143 | Unclassified_Cell_type_specific | NA |
| cg09663736 | NA | NA | TRUE | NA | NA | NA | NA |
| cg09949775 | NA | NA | NA | 19: 18760038-18763274 | NA | NA | NA |
| cg10167378 | NA | NA | NA | 1: 226821657-226823404 | NA | NA | NA |
| cg10270430 | NA | NA | TRUE | 6: 34132180-34132458 | NA | NA | TRUE |
| cg10332003 | NA | NA | TRUE | NA | 4: 185070345-185070459 | Unclassified_Cell_type_specific | NA |
| cg10590622 | NA | NA | NA | NA | NA | NA | NA |
| cg10776061 | NA | NA | TRUE | 19: 12628423-12629391 | NA | NA | TRUE |
| cg11035303 | NA | NA | TRUE | NA | NA | NA | NA |
| cg11317459 | NA | NA | NA | 13: 20770180-20770868 | 13: 21870878-21873080 | Promoter_Associated | NA |
| cg11639130 | NA | NA | TRUE | 12: 129869077-129869434 | 12: 131302803-131304615 | Promoter_Associated | TRUE |
| cg11728145 | NA | NA | NA | 2: 1637173-1637241 | NA | NA | TRUE |
| cg11728747 | NA | NA | TRUE | NA | NA | NA | NA |
| cg11791078 | NA | NA | NA | NA | NA | NA | NA |
| cg11986643 | NA | NA | NA | NA | 6: 32634123-32634701 | Unclassified | TRUE |
| cg12214399 | NA | NA | TRUE | NA | NA | NA | NA |
| cg12293347 | NA | RDMR | NA | NA | NA | NA | NA |
| cg12360123 | NA | NA | TRUE | NA | NA | NA | NA |
| cg12734688 | NA | NA | TRUE | NA | NA | NA | NA |
| cg12743416 | NA | NA | NA | NA | NA | NA | NA |
| cg12823953 | low-CpG: 139376377-139376484 | NA | NA | 3: 139376110-139376498 | 3: 137892888-137894011 | Promoter_Associated | NA |
| cg13038618 | NA | NA | NA | 14: 76536767-76537145 | NA | NA | NA |
| cg13205848 | NA | NA | TRUE | NA | 12: 5674812-5675561 | Unclassified_Cell_type_specific | NA |
| cg13422830 | NA | NA | TRUE | NA | NA | NA | NA |
| cg13506281 | NA | NA | NA | 13: 28811887-28812268 | NA | NA | NA |
| cg13617837 | NA | NA | TRUE | 6: 3669402-3669690 | NA | NA | TRUE |
| cg13730219 | NA | NA | NA | NA | NA | NA | NA |
| cg13749548 | NA | NA | NA | NA | NA | NA | NA |
| cg13943068 | NA | NA | NA | 4: 1550144-1550508 | NA | NA | NA |
| cg14173968 | NA | NA | TRUE | NA | NA | NA | NA |
| cg14223671 | NA | NA | NA | 16: 797343-798706 | 16: 857066-858592 | Promoter_Associated | NA |
| cg14447606 | NA | NA | TRUE | 2: 72223562-72226253 | NA | NA | NA |
| cg14456004 | NA | NA | NA | 13: 20770180-20770868 | 13: 21870878-21873080 | Promoter_Associated | NA |
| cg14463164 | NA | NA | TRUE | NA | NA | NA | NA |
| cg14646613 | NA | NA | TRUE | NA | NA | NA | NA |
| cg14651435 | NA | NA | NA | 7: 156902292-156902330 | NA | NA | NA |
| cg14852082 | NA | NA | NA | 4: 1550144-1550508 | NA | NA | NA |

TABLE 1-continued

Differential methylation of genes in DFU versus NFF using an Illumina-style annotation method

| Probe | Col2 | Col3 | Col4 | Col5 | Col6 | Col7 | Col8 |
|---|---|---|---|---|---|---|---|
| cg14895374 | NA | NA | NA | NA | NA | NA | TRUE |
| cg15260248 | NA | NA | TRUE | NA | NA | NA | NA |
| cg15497834 | NA | DMR | NA | NA | 20: 48998337-48999129 | Unclassified_Cell_type_specific | NA |
| cg15690379 | NA | NA | TRUE | NA | NA | NA | NA |
| cg15752756 | low-CpG: 32742410-32742475 | NA | NA | NA | 6: 32634123-32634701 | Unclassified | TRUE |
| cg15878909 | NA | NA | NA | NA | NA | NA | NA |
| cg16081854 | NA | NA | NA | 5: 361235-361628 | NA | NA | NA |
| cg16112880 | NA | NA | NA | 1: 199389889-199390390 | 1: 201122822-201124261 | Promoter_Associated | NA |
| cg16463697 | NA | NA | TRUE | NA | NA | NA | NA |
| cg16508714 | NA | NA | TRUE | NA | NA | NA | NA |
| cg16540391 | NA | NA | TRUE | NA | 6: 151041999-151042157 | Unclassified_Cell_type_specific | NA |
| cg16664523 | NA | NA | TRUE | NA | NA | NA | NA |
| cg17013691 | NA | NA | TRUE | 5: 14433305-14433455 | NA | NA | NA |
| cg17171539 | NA | NA | TRUE | NA | NA | NA | TRUE |
| cg17449954 | high-CpG: 39877885-39878287 | NA | NA | 1: 39877598-39878275 | 1: 40104740-40105984 | Unclassified_Cell_type_specific | TRUE |
| cg17602481 | NA | NA | NA | 13: 113908518-113908715 | 13: 114890255-114890920 | Unclassified_Cell_type_specific | TRUE |
| cg17662493 | NA | NA | NA | NA | NA | NA | NA |
| cg17811452 | NA | NA | NA | NA | NA | NA | NA |
| cg18004235 | NA | NA | TRUE | NA | NA | NA | NA |
| cg18009021 | low-CpG: 95595502-95595528 | NA | NA | NA | NA | NA | NA |
| cg18149745 | NA | NA | TRUE | NA | NA | NA | TRUE |
| cg18235100 | NA | NA | NA | 4: 81342012-81343857 | 4: 81124393-81124763 | Promoter_Associated | TRUE |
| cg18302225 | NA | CDMR | TRUE | 5: 55812102-55812159 | NA | NA | TRUE |
| cg18332838 | NA | NA | TRUE | NA | NA | NA | NA |
| cg18379295 | NA | NA | NA | NA | NA | NA | NA |
| cg18438894 | NA | NA | TRUE | NA | NA | NA | NA |
| cg18642369 | NA | NA | TRUE | NA | 13: 99651046-99651440 | Unclassified_Cell_type_specific | NA |
| cg19141316 | NA | NA | TRUE | NA | NA | NA | NA |
| cg19243721 | NA | NA | NA | 6: 166771808-166771895 | NA | NA | NA |
| cg19264571 | NA | RDMR | NA | 18: 10443763-10445606 | NA | NA | TRUE |
| cg19300401 | NA | NA | TRUE | NA | NA | NA | NA |
| cg19539986 | NA | NA | NA | NA | NA | NA | NA |
| cg19577074 | NA | NA | TRUE | NA | NA | NA | NA |
| cg19697575 | NA | NA | NA | 2: 172082064-172082421 | NA | NA | NA |
| cg19717773 | NA | NA | NA | 7: 2814039-2814102 | NA | NA | NA |
| cg19799454 | NA | NA | NA | 7: 63966088-63966326 | NA | NA | NA |
| cg19907305 | high-CpG: 18763111-18763118 | NA | NA | 19: 18760038-18763274 | NA | NA | NA |
| cg20274462 | NA | NA | TRUE | NA | NA | NA | NA |
| cg20321086 | NA | DMR | TRUE | 8: 62214562-62215149 | 8: 62051046-62052442 | Unclassified | TRUE |
| cg20346503 | NA | NA | TRUE | NA | NA | NA | TRUE |
| cg20539283 | NA | NA | NA | NA | NA | NA | NA |
| cg20895691 | NA | NA | TRUE | NA | NA | NA | TRUE |
| cg20976286 | NA | CDMR | NA | NA | NA | NA | NA |
| cg21211688 | NA | NA | NA | NA | NA | NA | NA |
| cg21332500 | NA | RDMR | NA | 7: 27199936-27200029 | NA | NA | NA |

TABLE 1-continued

Differential methylation of genes in DFU versus NFF using an Illumina-style annotation method

| | | | | | | | |
|---|---|---|---|---|---|---|---|
| cg21446981 | NA | NA | TRUE | NA | NA | NA | NA |
| cg21498547 | NA | NA | NA | 8: 1638463-1638636 | NA | NA | NA |
| cg21565914 | NA | NA | TRUE | NA | 2: 162929683-162931506 | Promoter_Associated | TRUE |
| cg21681643 | NA | NA | NA | NA | NA | NA | NA |
| cg21860675 | NA | NA | TRUE | NA | NA | NA | TRUE |
| cg21945639 | NA | NA | TRUE | 1: 198537912-198538577 | 1: 200270611-200272226 | Promoter_Associated_Cell_type_specific | NA |
| cg21964662 | NA | NA | NA | NA | NA | NA | NA |
| cg22031873 | NA | NA | NA | NA | NA | NA | NA |
| cg22749855 | NA | NA | NA | NA | 17: 76353631-76354680 | Promoter_Associated | NA |
| cg23052585 | NA | NA | NA | NA | NA | NA | NA |
| cg23159970 | NA | NA | TRUE | NA | NA | NA | NA |
| cg23192683 | NA | NA | TRUE | NA | NA | NA | NA |
| cg23677311 | NA | NA | TRUE | NA | NA | NA | NA |
| cg23698271 | NA | NA | TRUE | NA | NA | NA | NA |
| cg23763647 | NA | DMR | NA | 10: 4858068-4858934 | 10: 4867931-4869103 | Unclassified_Cell_type_specific | TRUE |
| cg24199384 | NA | NA | TRUE | NA | NA | NA | NA |
| cg24284539 | NA | NA | NA | 10: 13039521-13039676 | NA | NA | NA |
| cg24451872 | NA | NA | NA | NA | NA | NA | NA |
| cg24623760 | NA | NA | TRUE | NA | 12: 123609968-123611863 | Unclassified_Cell_type_specific | TRUE |
| cg25191304 | NA | NA | TRUE | NA | NA | NA | NA |
| cg25491704 | NA | NA | TRUE | NA | NA | NA | NA |
| cg25541928 | NA | NA | NA | NA | NA | NA | NA |
| cg25570222 | NA | NA | TRUE | NA | NA | NA | NA |
| cg25614253 | NA | NA | NA | 8: 143557823-143558304 | 8: 143561069-143561351 | Unclassified_Cell_type_specific | NA |
| cg25638870 | NA | NA | NA | 11: 88864029-88864366 | NA | NA | NA |
| cg25909532 | NA | NA | NA | NA | NA | NA | TRUE |
| cg25929399 | NA | NA | NA | NA | NA | NA | NA |
| cg26365090 | NA | NA | NA | NA | NA | NA | NA |
| cg26646659 | NA | CDMR | TRUE | 5: 55812102-55812159 | NA | NA | TRUE |
| cg26690407 | NA | NA | NA | NA | NA | NA | NA |
| cg26853458 | NA | NA | NA | NA | NA | NA | NA |
| cg26932889 | NA | NA | TRUE | NA | NA | NA | NA |
| cg27010076 | NA | NA | TRUE | NA | NA | NA | NA |
| cg27031754 | NA | NA | TRUE | NA | NA | NA | TRUE |
| cg27065717 | NA | NA | NA | 16: 84166244-84166479 | NA | NA | NA |
| cg27286614 | NA | NA | NA | 7: 2016696-2017035 | NA | NA | NA |
| cg27333018 | NA | NA | NA | NA | NA | NA | NA |

In some embodiments, the fibroblast, e.g., derived from a wound, such as a diabetic ulcer (e.g., diabetic foot ulcer), comprises an elevated level of a protein marker, e.g., fibronectin. For example, the level of the protein marker, e.g., fibronectin, is increased by at least 2-fold (e.g., at least 2-fold, 3-fold, 4-fold, 5-fold, 10-fold, or more). In other example, the fibroblast, e.g., derived from a wound, such as a diabetic ulcer (e.g., diabetic foot ulcer), comprises decreased level of a protein marker, e.g., smooth muscle actin or plasminogen activator inhibitor-1 (PAI-1, also called Serpin E1). For example, the level of the protein marker, e.g., smooth muscle actin or PAI-1, is decreased by at least 2-fold (e.g., at least 2-fold, 3-fold, 4-fold, 5-fold, 10-fold, or more).

For example, the amino acid sequence of human fibronectin is provided by GenBank Accession No. P02751.4 and is shown below:

```
                                                        (SEQ ID NO: 32)
  1   mlrgpgpgll llavqclgta vpstgasksk rqaqqmvqpq spvaysqskp gcydngkhyq 61   inqqwertyl gnalvctcyg gsrgfncesk peaeetcfdk ytgntyrvgd tyerpkdsmi 121   wdctcigagr grisctianr cheggqsyki gdtwrrphet ggymlecvol gngkgewtck 181   piaekcfdha agtsyvvget wekpyqgwmm vdctclgegs gritctsrnr cndqdtrtsy
```

```
 241  rigdtwskkd nrgnllqcic tgngrgewkc erhtsvqtts sgsgpftdvr aavyqpqphp
 301  qpppyghcvt dsgvvysvgm qwlktqgnkq mlctclgngv scqetavtqt yggnsngepc
 361  vlpftyngrt fyscttegrq dghlwcstts nyeqdqkysf ctdhtvlvqt rggnsngalc
 421  hfpflynnhn ytdctsegrr dnmkwcgttq nydadqkfgf cpmaaheeic ttnegvmyri
 481  gdqwdkqhdm ghmmrctcvg ngrgewtcia ysqlrdqciv dditynvndt fhkrheeghm
 541  lnctcfgqgr grwkcdpvdq cqdsetgtfy qigdswekyv hgvryqcycy grgigewhcq
 601  plqtypsssg pvevfitetp sqpnshpiqw napqpshisk yilrwrpkns vgrwkeatip
 661  ghlnsytikg lkpgvvyegq lisiqqyghq evtrfdfttt ststpvtsnt vtgettpfsp
 721  lvatsesvte itassfvvsw vsasdtvsgf rveyelseeg depqyldlps tatsvnipdl
 781  lpgrkyivnv yqisedgeqs lilstsqtta pdappdttvd qvddtsivvr wsrpqapitg
 841  yrivyspsve gsstelnlpe tansvtlsdl qpgvqyniti yaveenqest pvviqqettg
 901  tprsdtvpsp rdlqfvevtd vkvtimwtpp esavtgyrvd vipvnlpgeh gqrlpisrnt
 961  faevtglspg vtyyfkvfav shgreskplt aqqttkldap tnlqfvnetd stvlvrwtpp
1021  raqitgyrlt vgltrrgqpr qynvgpsysk yplrnlqpas eytvslvaik gnqespkatg
1081  vfttlqpgss ippyntevte ttivitwtpa prigfklgvr psqggeapre vtsdsgsivv
1141  sgltpgveyv ytiqvlrdgq erdapivnkv vtplspptnl hleanpdtgv ltvswerstt
1201  pditgyritt tptngqqgns leevvhadqs sctfdnlspg leynvsvytv kddkesvpis
1261  dtiipavppp tdlrftnigp dtmrvtwapp psidltnflv ryspvkneed vaelsispsd
1321  navvltnllp gteyvvsyss vyeqhestpl rgrqktglds ptgidfsdit ansftvhwia
1381  pratitgyri rhhpehfsgr predrvphsr nsitltnitp gteyvvsiva lngreesplll
1441  igqqstvsdv prdlevvaat ptsllisdwa pavtvryyri tygetggnsp vqeftvpgsk
1501  statisglkp gvdytitvya vtgrgdspas skpisinyrt eidkpsqmqv tdvqdnsisv
1561  kwlpsssvt gyrvtttpkn gpgptktkta gpdqtemtie glqptveyvv svyaqnpsge
1621  sqplvqtavt nidrpkglaf tdvdvdsiki awespqgqvs ryrvtyssspe dgihelfpap
1681  dgeedtaelq glrpgseytv svvalhddme sqpligtqst aipaptdlkf tqvtptslsa
1741  qwtppnvqlt gyrvrvtpke ktgpmkeinl apdsssvvvs glmvatkyev svyalkdtlt
1801  srpaqgvvtt lenvspprra rvtdatetti tiswrtktet itgfqvdavp angqtpiqrt
1861  ikpdvrsyti tglqpgtdyk iylytlndna rsspvvidas taidapsnlr flattpnsll
1921  vswqpprari tgyiikyekp gsspprevvpr prpgvteati tglepgteyt iyvialknnq
1981  ksepligrkk tdelpqlvtl phpnlhgpei ldvpstvqkt pfvthpgydt gngiqlpgts
2041  gqqpsvgqqm ifeehgfrrt tppttatpir hrprpyppnv geeiqighip redvdyhlyp
2101  hgpglnpnas tgqealsqtt iswapfqdts eyiischpvg tdeeplqfry pgtststlt
2161  gltrgatynv ivealkdqqr hkvreevvtv gnsvneglnq ptddscfdpy tvshyavgde
2221  wermsesgfk llcgclgfgs ghfrcdssrw chdngvnyki gekwdrggen gqmmsctclg
2281  ngkgefkcdp heatcyddgk tyhvgeqwqk eylgaicsct cfggqrgwrc dncrrpggep
2341  spegttgqsy nqysgryhqr tntnvncpie cfmpldvqad redsre
```

The mRNA sequence encoding human Fibronectin is provided by GenBank Accession No._212482.1, and the sequence is shown below. Start and stop codons are in bold and underlined.

(SEQ ID NO: 18)

```
   1  gcccgcgccg gctgtgctgc acaggggag gagagggaac cccaggcgcg agcgggaaga
  61  ggggacctgc agccacaact tctctggtcc tctgcatccc ttctgtccct ccacccgtcc
 121  ccttccccac cctctggccc ccaccttctt ggaggcgaca accccggga ggcattagaa
 181  gggatttttc ccgcaggttg cgaagggaag caaacttggt ggcaacttgc ctcccggtgc
 241  gggcgtctct cccccaccgt ctcaacatgc ttaggggtcc ggggcccggg ctgctgctgc
 301  tggccgtcca gtgcctgggg acagcggtgc cctccacggg agcctcgaag agcaagaggc
 361  aggctcagca aatggttcag ccccagtccc cggtggctgt cagtcaaagc aagcccggtt
 421  gttatgacaa tggaaaacac tatcagataa atcaacagtg ggagcggacc tacctaggca
 481  atgcgttggt ttgtacttgt tatggaggaa gccgaggttt taactgcgag agtaaacctg
 541  aagctgaaga gacttgcttt gacaagtaca ctgggaacac ttaccgagtg ggtgacactt
 601  atgagcgtcc taaagactcc atgatctggg actgtacctg catcggggct gggcgaggga
 661  gaataagctg taccatcgca aaccgctgcc atgaaggggg tcagtcctac aagattggtg
 721  acacctggag gagaccacat gagactggtg gttacatgtt agagtgtgtg tgtcttggta
 781  atggaaaagg agaatggacc tgcaagccca tagctgagaa gtgttttgat catgctgctg
 841  ggacttccta tgtggtcgga gaaacgtggg agaagcccta ccaaggctgg atgatggtag
 901  attgtacttg cctgggagaa ggcagcggac gcatcacttg cacttctaga aatagatgca
 961  acgatcagga cacaaggaca tcctatagaa ttggagacac ctggagcaag aaggataatc
1021  gaggaaacct gctccagtgc atctgcacag gcaacggccg aggagagtgg aagtgtgaga
1081  ggcacacctc tgtgcagacc acatcgagcg gatctggccc cttcaccgat gttcgtgcag
1141  ctgtttacca accgcagcct caccccagc ctcctcccta tggccactgt gtcacagaca
1201  gtggtgtggt ctactctgtg gggatgcagt ggctgaagac acaaggaaat aagcaaatgc
1261  tttgcacgtg cctgggcaac ggagtcagct gccaagagac agctgtaacc cagacttacg
1321  gtggcaactc aaatggagag ccatgtgtct taccattcac ctacaatggc aggacgttct
1381  actcctgcac cacagaaggg cgacaggacg gacatctttg gtgcagcaca acttcgaatt
1441  atgagcagga ccagaaatac tctttctgca gagaccacac tgtttggtt cagactcgag
1501  gaggaaattc caatggtgcc ttgtgccact tcccttcct atacaacaac cacaattaca
1561  ctgattgcac ttctgagggc agaagagaca acatgaagtg gtgtgggacc acacagaact
1621  atgatgccga ccagaagttt gggttctgcc ccatggctgc ccacgaggaa atctgcacaa
1681  ccaatgaagg ggtcatgtac cgcattggag atcagtggga taagcagcat gacatgggtc
1741  acatgatgag gtgcacgtgt gttgggaatg tcgtgggga atggacatgc attgcctact
1801  cgcagcttcg agatcagtgc attgttgatg acatcactta caatgtgaac gacacattcc
1861  acaagcgtca tgaagagggg cacatgctga actgtacatg cttcggtcag gtcgggca
1921  ggtggaagtg tgatcccgtc gaccaatgcc aggattcaga gactgggacg ttttatcaaa
1981  ttggagattc atgggagaag tatgtgcatg gtgtcagata ccagtgctac tgctatggcc
2041  gtggcattgg ggagtggcat tgccaaccct tacagaccta tccaagctca gtggtcctg
2101  tcgaagtatt tatcactgag actccgagtc agcccaactc ccacccatc cagtggaatg
2161  caccacagcc atctcacatt tccaagtaca ttctcaggtg agacctaaa aattctgtag
```

```
2221  gccgttggaa ggaagctacc ataccaggcc acttaaactc ctacaccatc aaaggcctga
2281  agcctggtgt ggtatacgag ggccagctca tcagcatcca gcagtacggc caccaagaag
2341  tgactcgctt tgacttcacc accaccagca ccagcacacc tgtgaccagc aacaccgtga
2401  caggagagac gactcccttt tctcctcttg tggccacttc tgaatctgtg accgaaatca
2461  cagccagtag ctttgtggtc tcctgggtct cagcttccga caccgtgtcg ggattccggg
2521  tggaatatga gctgagtgag gagggagatg agccacagta cctggatctt ccaagcacag
2581  ccacttctgt gaacatccct gacctgcttc ctggccgaaa atacattgta aatgtctatc
2641  agatatctga ggatggggag cagagtttga tcctgtctac ttcacaaaca acagcgcctg
2701  atgcccctcc tgacccgact gtggaccaag ttgatgacac ctcaattgtt gttcgctgga
2761  gcagacccca ggctcccatc acagggtaca gaatagtcta ttcgccatca gtagaaggta
2821  gcagcacaga actcaacctt cctgaaactg caaactccgt caccctcagt gacttgcaac
2881  ctggtgttca gtataacatc actatctatg ctgtggaaga aaatcaagaa agtacacctg
2941  ttgtcattca acaagaaacc actggcaccc cacgctcaga tacagtgccc tctcccaggg
3001  acctgcagtt tgtggaagtg acagacgtga aggtcaccat catgtggaca ccgcctgaga
3061  gtgcagtgac cggctaccgt gtggatgtga tccccgtcaa cctgcctggc gagcacgggc
3121  agaggctgcc catcagcagg aacacctttg cagaagtcac cgggctgtcc cctggggtca
3181  cctattactt caaagtcttt gcagtgagcc atgggaggga gagcaagcct ctgactgctc
3241  aacagacaac caaactggat gctcccacta acctccagtt tgtcaatgaa actgattcta
3301  ctgtcctggt gagatggact ccacctcggg cccagataac aggataccga ctgaccgtgg
3361  gccttacccg aagaggacag cccaggcagt acaatgtggg tccctctgtc tccaagtacc
3421  cactgaggaa tctgcagcct gcatctgagt acaccgtatc cctcgtggcc ataaagggca
3481  accaagagag ccccaaagcc actggagtct ttaccacact gcagcctggg agctctattc
3541  caccttacaa caccgaggtg actgagacca ccattgtgat cacatggacg cctgctccaa
3601  gaattggttt taagctgggt gtacgaccaa gccagggagg agaggcacca cgagaagtga
3661  cttcagactc aggaagcatc gttgtgtccg gcttgactcc aggagtagaa tacgtctaca
3721  ccatccaagt cctgagagat ggacaggaaa gagatgcgcc aattgtaaac aaagtggtga
3781  caccattgtc tccaccaaca aacttgcatc tggaggcaaa ccctgacact ggagtgctca
3841  cagtctcctg ggagaggagc accaccccag acattactgg ttatagaatt accacaaccc
3901  ctacaaacgg ccagcaggga aattctttgg aagaagtggt ccatgctgat cagagctcct
3961  gcactttga taacctgagt cccggcctgg agtacaatgt cagtgtttac actgtcaagg
4021  atgacaagga aagtgtccct atctctgata ccatcatccc agaggtgccc caactcactg
4081  acctaagctt tgttgatata accgattcaa gcatcggcct gaggtggacc ccgctaaact
4141  cttccaccat tattgggtac cgcatcacag tagttgcggc aggagaaggt atccctattt
4201  ttgaagattt tgtggactcc tcagtaggat actacacagt cacagggctg gagccgggca
4261  ttgactatga tatcagcgtt atcactctca ttaatggcgg cgagagtgcc cctactacac
4321  tgacacaaca aacggctgtt cctcctccca ctgacctgcg attcaccaac attggtccag
4381  acaccatgcg tgtcacctgg gctccacccc catccattga tttaaccaac ttcctggtgc
4441  gttactcacc tgtgaaaaat gaggaagatg ttgcagagtt gtcaatttct ccttcagaca
4501  atgcagtggt cttaacaaat ctcctgcctg gtacagaata tgtagtgagt gtctccagtg
4561  tctacgaaca acatgagagc acacctctta gaggaagaca gaaaacaggg cttgattccc
4621  caactggcat tgacttttct gatattactg ccaactcttt tactgtgcac tggattgctc
```

-continued

```
4681  ctcgagccac catcactggc tacaggatcc gccatcatcc cgagcacttc agtgggagac
4741  ctcgagaaga tcgggtgccc cactctcgga attccatcac cctcaccaac ctcactccag
4801  gcacagagta tgtggtcagc atcgttgctc ttaatggcag agaggaaagt cccttattga
4861  ttggccaaca atcaacagtt tctgatgttc cgagggacct ggaagttgtt gctgcgaccc
4921  ccaccagcct actgatcagc tgggatgctc ctgctgtcac agtgagatat tacaggatca
4981  cttacggaga gacaggagga aatagccctg tccaggagtt cactgtgcct gggagcaagt
5041  ctacagctac catcagcggc cttaaacctg gagttgatta taccatcact gtgtatgctg
5101  tcactggccg tggagacagc cccgcaagca gcaagccaat ttccattaat taccgaacag
5161  aaattgacaa accatcccag atgcaagtga ccgatgttca ggacaacagc attagtgtca
5221  agtggctgcc ttcaagttcc cctgttactg gttacagagt aaccaccact cccaaaaatg
5281  gaccaggacc aacaaaaact aaaactgcag gtccagatca aacagaaatg actattgaag
5341  gcttgcagcc cacagtggag tatgtggtta gtgtctatgc tcagaatcca gcggagaga
5401  gtcagcctct ggttcagact gcagtaacca acattgatcg ccctaaagga ctggcattca
5461  ctgatgtgga tgtcgattcc atcaaaattg cttgggaaag cccacagggg caagtttcca
5521  ggtacagggt gacctactcg agccctgagg atggaatcca tgagctattc cctgcacctg
5581  atggtgaaga agacactgca gagctgcaag gcctcagacc gggttctgag tacacagtca
5641  gtgtggttgc cttgcacgat gatatggaga gccagcccct gattggaacc cagtccacag
5701  ctattcctgc accaactgac ctgaagttca ctcaggtcac acccacaagc ctgagcgccc
5761  agtggacacc acccaatgtt cagctcactg gatatcgagt gcgggtgacc cccaaggaga
5821  agaccggacc aatgaaagaa atcaaccttg ctcctgacag ctcatccgtg gttgtatcag
5881  gacttatggt ggccaccaaa tatgaagtga gtgtctatgc tcttaaggac actttgacaa
5941  gcagaccagc tcagggagtt gtcaccactc tggagaatgt cagcccacca agaagggctc
6001  gtgtgacaga tgctactgag accaccatca ccattagctg agaaaccaag actgagacga
6061  tcactggctt ccaagttgat gccgttccag ccaatggcca gactccaatc cagagaacca
6121  tcaagccaga tgtcagaagc tacaccatca caggtttaca accaggcact gactacaaga
6181  tctacctgta caccttgaat gacaatgctc ggagctcccc tgtggtcatc gacgcctcca
6241  ctgccattga tgcaccatcc aacctgcgtt tcctggccac cacacccaat tccttgctgg
6301  tatcatggca gccgccacgt gccaggatta ccggctacat catcaagtat gagaagcctg
6361  ggtctcctcc cagagaagtg gtccctcggc ccgccctgg tgtcacagag ctactatta
6421  ctggcctgga accgggaacc gaatatacaa tttatgtcat tgccctgaag aataatcaga
6481  agagcgagcc cctgattgga aggaaaaaga cagacgagct tccccaactg gtaacccttc
6541  cacaccccaa tcttcatgga ccagagatct tggatgttcc ttccacagtt caaagaccc
6601  ctttcgtcac ccaccctggg tatgacactg aaatggtat tcagcttcct ggcacttctg
6661  gtcagcaacc cagtgttggg caacaaatga tctttgagga acatggtttt aggcggacca
6721  caccgcccac aacggccacc cccataaggc ataggccaag accataccg ccgaatgtag
6781  gtgaggaaat ccaaattggt cacatcccca gggaagatgt agactatcac ctgtacccac
6841  acggtccggg actcaatcca aatgcctcta caggacaaga agctctctct cagacaacca
6901  tctcatgggc cccattccag gacacttctg agtacatcat ttcatgtcat cctgttggca
6961  ctgatgaaga acccttacag ttcagggttc ctggaacttc taccagtgcc actctgacag
7021  gcctcaccag aggtgccacc tacaacatca tagtggaggc actgaaagac cagcagaggc
```

```
7081  ataaggttcg ggaagaggtt gttaccgtgg gcaactctgt caacgaaggc ttgaaccaac 7141  ctacggatga ctcgtgcttt gaccoctaca cagtttccca ttatgccgtt ggagatgagt 7201  gggaacgaat gtctgaatca ggctttaaac tgttgtgcca gtgcttaggc tttggaagtg 7261  gtcatttcag atgtgattca tctagatggt gccatgacaa tggtgtgaac tacaagattg 7321  gagagaagtg ggaccgtcag ggagaaaatg gccagatgat gagctgcaca tgtcttggga 7381  acggaaaagg agaattcaag tgtgaccctc atgaggcaac gtgttatgat gatgggaaga 7441  cataccacgt aggagaacag tggcagaagg aatatctcgg tgccatttgc tcctgcacat 7501  gctttggagg ccagcggggc tggcgctgtg caactgccg cagacctggg ggtgaaccca 7561  gtcccgaagg cactactggc cagtcctaca accagtattc tcagagatac catcagagaa 7621  caaacactaa tgttaattgc ccaattgagt gcttcatgcc tttagatgta caggctgaca 7681  gagaagattc ccgagagtaa atcatctttc caatccagag gaacaagcat gtctctctgc 7741  caagatccat ctaaactgga gtgatgttag cagacccagc ttagagttct tctttctttc 7801  ttaagccctt tgctctggag gaagttctcc agcttcagct caactcacag cttctccaag 7861  catcaccctg ggagtttcct gagggttttc tcataaatga gggctgcaca ttgcctgttc 7921  tgcttcgaag tattcaatac cgctcagtat tttaaatgaa gtgattctaa gatttggttt 7981  gggatcaata ggaaagcata tgcagccaac caagatgcaa atgttttgaa atgatatgac 8041  caaaatttta agtaggaaag tcacccaaac acttctgctt tcacttaagt gtctggcccg 8101  caatactgta ggaacaagca tgatcttgtt actgtgatat tttaaatatc cacagtactc 8161  acttttttcca aatgatccta gtaattgcct agaaatatct ttctcttacc tgttatttat 8221  caattttttcc cagtatttt atacggaaaa aattgtattg aaaacactta gtatgcagtt 8281  gataagagga atttggtata attatggtgg gtgattattt tttatactgt atgtgccaaa 8341  gctttactac tgtggaaaga caactgtttt aataaaagat ttacattcca caacttgaag 8401  ttcatctatt tgatataaga caccttcggg ggaaataatt cctgtgaata ttcttttttca 8461  attcagcaaa catttgaaaa tctatgatgt gcaagtctaa ttgttgattt cagtacaaga 8521  ttttctaaat cagttgctac aaaaactgat tggtttttgt cacttcatct cttcactaat 8581  ggagatagct ttacactttc tgctttaata gatttaagtg gaccccaata tttattaaaa 8641  ttgctagttt accgttcaga agtataatag aaataatctt tagttgctct tttctaacca 8701  ttgtaattct tccctttcttc cctccacctt tccttcattg aataaacctc tgttcaaaga 8761  gattgcctgc aagggaaata aaaatgacta agatattaaa aaaaaaaaa aaaaa
```

The amino acid sequence of human smooth muscle actin is provided by GenBank Accession No. AAH94877.1 and is shown below.

```
                                                            (SEQ ID NO: 19)
  1   mceeettalv cdngsglcka gfagddapra vfpsivgrpr hqgvmvgmgq kdsyvgdeaq 61   skrgiltlky piehgiitnw ddmekiwhhs fynelrvape ehptllteap lnpkanrekm 121   tqimfetfnv pamyvaiqav lslyasgrtt givldsgdgv thnvpiyegy alphaimrld 181   lagrdltdyl mkiltergys fvttaereiv rdikeklcyv aldfenemat aasssleks 241   yelpdgqvit ignerfrcpe tlfqpsfigm esagihetty nsimkcdidi rkdlyannvl 301   sggttmypgi adrmqkeita lapstmkiki iapperkysv wiggsilasl stfqqmwisk 361   peydeagpsi vhrkcf
```

The mRNA sequence encoding human smooth muscle actin is provided by GenBank Accession No. BC094877.1 and is shown below. The start and stop codons are in bold and underlined.

```
                                                                  (SEQ ID NO: 20)
   1    aggtttctta aaaaaaacac acagagaaat attgtgctcc agccccagc tcattccacc 61    gctcccacca tgtgtgaaga agagaccacc gcccttgtgt gtgacaatgg ctctggcctg 121    tgcaaggcag gctttgcagg agatgatgcc cccagggctg tcttcccctc cattgtgggc 181    cgccctagac atcagggtgt gatggtggga atgggccaga aagacagcta tgtggggac 241    gaggctcaga gcaagcgtgg gatcctaact ctcaagtacc ctattgaaca tggcatcatc 301    accaactggg atgacatgga aagatctgg caccactcct tctacaatga gcttcgagta 361    gcaccagaag agcacccac cctgctcaca gaggccccc taaaccccaa agcaaacaga 421    gagaagatga cccagatcat gttcgaaacc ttcaatgtcc ctgccatgta tgttgctatt 481    caggctgtgc tctcactcta tgcatccggc cgtaccacag gcatcgttct ggattcgggg 541    gatggcgtca cccacaatgt ccccatctat gagggctatg cactgcccca tgccatcatg 601    cgtcttgacc tggctggacg ggatctcaca gactacctca tgaagattct cacagaaaga 661    ggctattcct ttgtgaccac agctgagaga gaaattgtac gagacatcaa ggagaagctg 721    tgctatgtag ccctggattt cgagaatgag atggccacag cagcttcatc ttcttccctg 781    gagaaaagct acgagttgcc tgatgggcag gtcatcacta ttggcaacga gcgcttccgc 841    tgcccggaga ccctcttcca gccttccttc attggcatgg agtcagctgg aattcatgaa 901    acaacataca attccatcat gaagtgtgac attgacatcc gcaaagattt gtatgctaac 961    aatgtcctct ctggggcac taccatgtac cctggcattg ctgacaggat gcagaaggaa 1021    atcacagcct ggctcccag caccatgaag atcaagatta tcgctcctcc tgagcggaag 1081    tactcagtct ggattggcgg ctccatcctg gcctctctct ccaccttcca gcaaatgtgg 1141    atcagcaagc agagtatga tgaggcaggg ccctccattg tccacaggaa atgcttctaa 1201    agtcagaggg ccttctctgg ggatccccac aagactgctg tcaccagcca cagatcatta 1261    aaaccttcaa gccgaaaaaa aaaaaaaaaa aaaaaaaaaa aaaa
```

The amino acid sequence of PAI-1 is provided by GenBank Accession No. P05121.1 and is provided below.

```
                                                                  (SEQ ID NO: 21)
   1    mqmspaltcl vlglalvfge gsavhhppsy vahlasdfgv rvfqqvaqas kdrnvvfspy 61    gvasvlamlq lttggetqqq iqaamgfkid dkgmapalrh lykelmgpwn kdeisttdai 121    fvqrdlklvg gfmphffrlf rstvkqvdfs everarfiin dwvkthtkgm isnllgkgav 181    dqltrlvlvn alyfngqwkt pfpdssthrr lfhksdgstv svpmmaqtnk fnyteftttpd 241    ghyydilelp yhgdtlsmfi aapyekevpl saltnilsaq lishwkgnmt rlprllvlpk 301    fsletevdlr kplenlgmtd mfrqfqadft slsdgeplhv aqalqkvkie vnesgtvass 361    stavivsarm apeeiimdrp flfvvrhnpt gtvlfmgqvm ep
```

The mRNA sequence of PAI-1 is provided by GenBank Accession No. M16006.1 and is provided below. The start and stop codons are in bold and underlined.

```
                                                                  (SEQ ID NO: 22)
   1    gaattcctgc agctcagcag ccgccgccag agcaggacga accgccaatc gcaaggcacc
```

-continued

```
  61   tctgagaact tcaggatgca gatgtctcca gccctcacct gcctagtcct gggcctggcc
 121   cttgtctttg gtgaagggtc tgctgtgcac catcccccat cctacgtggc ccacctggcc
 181   tcagacttcg gggtgagggt gtttcagcag gtggcgcagg cctccaagga ccgcaacgtg
 241   gttttctcac cctatggggt ggcctcggtg ttggccatgc tccagctgac aacaggagga
 301   gaaacccagc agcagattca agcagctatg ggattcaaga ttgatgacaa gggcatggcc
 361   cccgccctcc ggcatctgta caaggagctc atggggccat ggaacaagga tgagatcagc
 421   accacagacg cgatcttcgt ccagcgggat ctgaagctgg tccagggctt catgccccac
 481   ttcttcaggc tgttccggag cacggtcaag caagtggact tttcagaggt ggagagagcc
 541   agattcatca tcaatgactg ggtgaagaca cacacaaaag gtatgatcag caacttgctt
 601   gggaaaggag ccgtggacca gctgacacgg ctggtgctgg tgaatgccct ctacttcaac
 661   ggccagtgga agactcccct tccccgactcc agcacccacc gccgcctctt ccacaaatca
 721   gacggcagca ctgtctctgt gcccatgatg gctcagacca acaagttcaa ctatactgag
 781   ttcaccacgc ccgatggcca ttactacgac atcctggaac tgccctacca cggggacacc
 841   ctcagcatgt tcattgctgc cccttatgaa aagaggtgc ctctctctgc cctcaccaac
 901   attctgagtg cccagctcat cagccactgg aaaggcaaca tgaccaggct gccccgcctc
 961   ctggttctgc ccaagttctc cctggagact gaagtcgacc tcaggaagcc cctagagaac
1021   ctgggaatga ccgacatgtt cagacagtttt caggctgact tcacgagtct ttcagaccaa
1081   gagcctctcc acgtcgcgca ggcgctgcag aaagtgaaga tcgaggtgaa cgagagtggc
1141   acggtggcct cctcatccac agctgtcata gtctcagccc gcatggcccc cgaggagatc
1201   atcatggaca gaccccttcct ctttgtggtc cggcacaacc ccacaggaac agtccttttc
1261   atgggccaag tgatggaacc ctgacccctgg ggaaagacgc cttcatctgg acaaaactg
1321   gagatgcatc gggaagaag aaactccgaa gaaaagaatt ttagtgttaa tgactctttc
1381   tgaaggaaga aagacattt gccttttgtt aaagatggt aaaccagatc tgtctccaag
1441   accttggcct ctccttggag gacctttagg tcaaactccc tagtctccac ctgagaccct
1501   gggagagaag tttgaagcac aactccctta aggtctccaa accagacggt gacgcctgcg
1561   ggaccatctg ggcacctgc ttccacccgt ctctctgccc actcgggtct gcagacctgg
1621   ttcccactga ggcccttttgc aggatggaac tacgggctt acaggagctt ttgtgtgcct
1681   ggtagaaact atttctgttc cagtcacatt gccatcactc ttgtactgcc tgccaccgcg
1741   gaggaggctg gtgacaggcc aaaggccagt ggaagaaaca ccctttcatc tcagagtcca
1801   ctgtggcact ggccaccct ccccagtaca ggggtgctgc aggtggcaga gtgaatgtcc
1861   cccatcatgt ggcccaactc tcctggcctg ccatctccc tccccagaaa cagtgtgcat
1921   gggttatttt ggagtgtagg tgacttgtttt actcattgaa gcagatttct gcttccttttt
1981   atttttatag gaatagagga agaaatgtca gatgcgtgcc cagctcttca cccccaatc
2041   tcttggtggg gaggggtgta cctaaatatt tatcatatcc ttgcccttga gtgcttgtta
2101   gagagaaaga gaactactaa ggaaaataat attatttaaa ctcgctccta gtgtttcttt
2161   gtggtctgtg tcaccgtatc tcaggaagtc cagccacttg actggcacac acccctccgg
2221   acatccagcg tgacggagcc cacactgcca ccttgtggcc gctgagacc ctcgcgcccc
2281   ccgcgccccc cgcgcccctc ttttcccct tgatggaaat tgaccataca atttcatcct
2341   ccttcagggg atcaaaagga cggagtgggg ggacagagac tcagatgagg acagagtggt
2401   ttccaatgtg ttcaatagat ttaggagcag aaatgcaagg ggctgcatga cctaccagga
2461   cagaactttc cccaattaca gggtgactca cagccgcatt ggtgactcac ttcaatgtgt
```

-continued

```
2521   catttccggc tgctgtgtgt gagcagtgga cacgtgaggg gggggtgggt gagagagaca 2581   ggcagctcgg attcaactac cttagataat atttctgaaa acctaccagc cagagggtag 2641   ggcacaaaga tggatgtaat gcactttggg aggccaaggc gggaggattg cttgagccca 2701   ggagttcaag accagcctgg gcaacatacc aagaccccg tctctttaaa aatatatata 2761   ttttaaatat acttaaatat atatttctaa tatctttaaa tatatatata tattttaaag 2821   accaatttat gggagaattg cacacagatg tgaaatgaat gtaatctaat agaagc
```

The protein sequence encoding human TGFβ1 is provided by GenBank Accession No: P01137.2 (incorporated herein by reference), and the sequence is shown below.

(SEQ ID NO: 23)
```
  1   mppsglrlll lllpllwllv ltpgrpaagl stcktidmel vkrkrieair gqilsklrla 61   sppsqgevpp gplpeavlal ynstrdrvag esaepepepe adyyakevtr vlmvethnei 121   ydkfkqsths iymffntsel reavpepvll sraelrllrl klkveqhvel yqkysnnswr 181   ylsnrllaps dspewlsfdv tgvvrqwlsr ggeiegfrls ahcscdsrdn tlqvdingft 241   tgrrgdlati hgmnrpfll1 matpleraqh lqssrhrral dtnycfsste kncovrqlyi 301   dfrkdlgwkw ihepkgyhan fclgpcpyiw sldtgyskvl alynqhnpga saapccvpqa 361   leplpivyyv grkpkveqls nmivrsckcs
```

The mRNA sequence encoding human TGFβ1 is provided by GenBank Accession No: NM_000660.5 (incorporated herein by reference), and the sequence is shown below.

(SEQ ID NO: 24)
```
   1   agccggtccc cgccgccgcc gcccttcgcg ccctgggcca tctccctccc acctccctcc 61   gcggagcagc cagacagcga gggccccggc cggggcagg ggggacgccc cgtccggggc 121   accccccgg ctctgagccg cccgcggggc cggcctcggc ccggagcgga ggaaggagtc 181   gccgaggagc agcctgaggc cccagagtct gagacgagcc gccgccgccc ccgccactgc 241   ggggaggagg gggaggagga gcgggaggag ggacgagctg gtcgggagaa gaggaaaaaa 301   acttttgaga cttttccgtt gccgctggga gccggaggcg cggggacctc ttggcgcgac 361   gctgccccgc gaggaggcag gacttgggga ccccagaccg cctccctttg ccgccgggga 421   cgcttgctcc ctccctgccc cctacacggc gtccctcagg cgcccccatt ccggaccagc 481   cctcgggagt cgccgacccg gcctcccgca aagactttc cccagacctc gggcgcaccc 541   cctgcacgcc gccttcatcc ccggcctgtc tcctgagccc ccgcgcatcc tagacccttt 601   ctcctccagg agacggatct ctctccgacc tgccacagat cccctattca agaccaccca 661   ccttctggta ccagatcgcg cccatctagg ttatttccgt gggatactga gacacccccg 721   gtccaagcct cccctccacc actgcgccct tctccctgag gacctcagct ttccctcgag 781   gccctcctac cttttgccgg gagaccccca gccctgcag ggcggggcc tcccaccac 841   accagccctg ttcgcgctct cggcagtgcc ggggggcgcc gcctccccca tgccgccctc 901   cgggctgcgg ctgctgccgc tgctgctacc gctgctgtgg ctactggtgc tgacgcctgg 961   ccggccgcc gcgggactat ccacctgcaa gactatcgac atggagctgg tgaagcggaa 1021   gcgcatcgag gccatccgcg gccagatcct gtccaagctg cggctcgcca gcccccgag 1081   ccaggggag gtgccgcccg gccgctgcc gaggccgtg ctcgccctgt acaacagcac 1141   ccgcgaccgg gtggccgggg agagtgcaga accggagccc gagcctgagg ccgactacta
```

-continued

```
1201  cgccaaggag gtcacccgcg tgctaatggg ggaaacccac aacgaaatct atgacaagtt 1261  caagcagagt acacacagca tatatatgtt cttcaacaca tcagagctcc gagaagcggt 1321  acctgaaccc gtgttgctct cccgggcaga gctgcgtctg ctgaggctca agttaaaagt 1381  ggagcagcac gtggagctgt accagaaata cagcaacaat tcctggcgat acctcagcaa 1441  ccggctgctg gcacccagcg actcgccaga gtggttatct tttgatgtca ccggagttgt 1501  gcggcagtgg ttgagccgtg gaggggaaat tgagggcttt cgccttagcg cccactgctc 1561  ctgtgacagc agggataaca cactgcaagt ggacatcaac gggttcacta ccggccgccg 1621  aggtgacctg gccaccattc atggcatgaa ccggccttc ctgcttctca tggccacccc 1681  gctggagagg gcccagcatc tgcaaagctc ccggcaccgc cgagccctgg acaccaacta 1741  ttgcttcagc tccacggaga agaactgctg cgtgcggcag ctgtacattg acttccgcaa 1801  ggacctcggc tggaagtgga tccacgagcc caagggctac catgccaact tctgcctcgg 1861  gccctgcccc tacatttgga gcctggacac gcagtacagc aaggtcctgg ccctgtacaa 1921  ccagcataac ccgggcgcct cggcggcgcc gtgctgcgtg ccgcaggcgc tggagccgct 1981  gcccatcgtg tactacgtgg gccgcaagcc caaggtggag cagctgtcca acatgatcgt 2041  gcgctcctgc aagtgcagct gaggtcccgc cccgccccgc ccgccccgg caggcccggc 2101  cccacccgc cccgccccg ctgccttgcc catggggggct gtatttaagg acacccgtgc 2161  cccaagccca cctggggccc cattaaagat ggagagagga ctgcggatct ctgtgtcatt 2221  gggcgcctgc ctggggtctc catccctgac gttcccccac tcccactccc tctctctccc 2281  tctctgcctc ctcctgcctg tctgcactat tcctttgccc ggcatcaagg cacaggggac 2341  cagtggggaa cactactgta gttagatcta tttattgagc accttgggca ctgttgaagt 2401  gccttacatt aatgaactca ttcagtcacc atagcaacac tctgagatgc agggactctg 2461  ataacacccca ttttaaaggt gaggaaacaa gcccagagag gttaagggag gagttcctgc 2521  ccaccaggaa cctgctttag tggggggatag tgaagaagac aataaaagat agtagttcag 2581  gcc
```

In other embodiments, the population of fibroblasts comprises a genetically modified fibroblast.

As described above, the composition optionally comprises a bioactive composition. The bioactive composition decreases inflammation, increases vascular regeneration, increases muscular regeneration, and/or promote skin regeneration. Exemplary bioactive compositions are described above.

The number of cells in a composition and the mode of administration may vary depending on the site and condition being treated (e.g., location of a wound or size of a wound). As non-limiting examples, in accordance with the present invention, a device seeded with about 10-500×10$^6$ fibroblasts is administered to a subject (e.g., diabetic subject) to effect wound healing. A skilled practitioner can modulate the amounts and methods of fibroblast-based treatments according to requirements, limitations, and/or optimizations determined for each case.

In some embodiments, the scaffold composition comprises between about 10×10$^6$ and 600×10$^6$ viable cells (e.g., fibroblasts). In some cases, the cells (e.g., fibroblasts) are seeded at a concentration of about 1×10$^3$ to 1×10$^8$ cells/ml (e.g., about 5×10$^3$ to 5×10$^7$ cells/ml, or about 1×10$^4$ to 1×10$^7$ cells/ml) into the device. For example, the cells are seeded in a device having a volume of 1-500 uL (e.g., 10-250 uL, 20-100 uL, or 40-60 uL, or about 50 uL). The dose of the device to be delivered to the subject depends on the magnitude of the injury or diseased area, e.g., one milliliter of gel for a relatively small wound and up to 50 mls of gel for a large wound. In some examples, the device has a volume of 1-500 uL (e.g., 10-250 uL, 20-100 uL, or 40-60 uL, or about 50 uL).

The composition preferably has less than 0.5 EU/ml of endotoxin and no bacterial or fungal growth.

The present invention also features a method of treating a wound in a patient in need thereof comprising administering a composition described herein. In some cases, the patient suffers from diabetes and/or a wound (e.g., located in an extremity of the patient). Exemplary extremities include arms, legs, feet, hands, fingers, and toes. For example, the patient suffers from an ulcer, e.g., a foot ulcer. Exemplary ulcers are at least about 25 mm, 50 mm, 1 cm, 2 cm, 3 cm, 4 cm, 5 cm, 6 cm, 7 cm, 8 cm, 9 cm, 10 cm, or greater in diameter.

The method provides compositions in which the population of fibroblasts includes an autologous, allogeneic, or xenogeneic fibroblast. For example, the population of fibroblasts comprises at least 10% autologous fibroblasts (e.g., at least 10%, 15%, 20%, 25%, 30%, 35%, 40%, 45%, 50%, 55%, 60%, 65%, 70%, 75%, 80%, 85%, 90%, 95%, 99%, or more); at least 10% allogeneic fibroblasts (e.g., at least 10%, 15%, 20%, 25%, 30%, 35%, 40%, 45%, 50%, 55%, 60%, 65%, 70%, 75%, 80%, 85%, 90%, 95%, 99%, or more); or at least 10% xenogeneic fibroblasts (e.g., at least 10%, 15%, 20%, 25%, 30%, 35%, 40%, 45%, 50%, 55%, 60%, 65%, 70%, 75%, 80%, 85%, 90%, 95%, 99%, or more).

The described the devices are administered to the tissues of the recipient organism of interest, including humans and non-human animals.

Devices of the present invention are administered or implanted orally, systemically, sub- or trans-cutaneously, as an arterial stent, surgically, or via injection. In some examples, the devices described herein are administered by routes such as injection (e.g., subcutaneous, intravenous, intracutaneous, percutaneous, or intramuscular) or implantation.

In one embodiment, administration of the device is mediated by injection or implantation into a wound or a site adjacent to the wound. For example, the wound is external or internal.

The invention will be further illustrated in the following non-limiting examples.

EXAMPLES

Example 1: Effect of Fibroblasts Derived from a Site Adjacent to a Diabetic Foot Ulcer on Wound Healing A mouse cutaneous wound-healing model was used to characterize the in vivo wound-healing potential of isolated fibroblasts. Specifically, mouse models were used to determine the effect of various populations of fibroblasts on wound healing in non-diabetic and diabetic mice.

Alginate hydrogels were used as exemplary material systems and delivery devices, as the physical, chemical, and biological properties of alginate gels can be readily manipulated to develop gels with a range of properties. For example, the gel, e.g., injectable gel, can be introduced directly into the tissue at or surrounding the wound, via needle or syringe, where the transplanted cells aid in upregulating a host healing response.

High G-block-containing alginate, MVG (M:G=40:60; MW~250 kDa; ProNova Biomedical, Oslo, Norway) was used to also obtain low-molecular alginate (MW~50 kDa) by gamma irradiation (3 MRad) (EH&S Lab at MIT, Cambridge, Mass.). To facilitate degradation and cell release, 1% of the sugar residues in the alginate chains were oxidized using sodium periodate (Sigma-Aldrich) and the alginate was dialyzed and lyophilized. Alginate chains were further modified to contain RGD-binding domains (GGGGRGDSH (SEQ ID NO: 29), Peptides 2.0, Virginia; two RGD per HMW chain or per five LMW chain) using carbodiimide chemistry, dialyzed, and lyophilized. The final concentration of alginate gels was 2% w/v (HMW:LMW=25:75) in serum-free DMEM. Gels contained $1e^6$ cells per 60 mL and were ionically cross-linked with 4% v/v 1.22M calcium sulfate solution. See, Kong et al., 2004 Biomacromolecules 5, 1720, incorporated herein by reference.

Sixteen-week-old C57BL6 male mice (Jackson Laboratories, Bar Harbor, Me.) were anesthetized, and two 6-mm full-thickness skin punch biopsies were obtained from the shaved dorsum of the animals. Fibroblasts were combined with an alginate-based hydrogel formulation described above. A total of 60 mL of blank hydrogel or cell-loaded hydrogel ($1 \times 10^6$ cells/wound) was injected intradermally into three sites along the wound margins immediately after wound creation (day 0).

The study groups were as follows. Both groups of mice (i.e., diabetic and non-diabetic) were treated with the following four treatments: a) alginate hydrogel-containing device alone (Hydrogel); b) alginate hydrogel-containing device that contains fibroblasts originating from the skin area adjacent to an existing chronic diabetic foot ulcer (F-DFU); c) alginate hydrogel-containing device that contains fibroblasts originating from the skin of the dorsum of the foot of a diabetic foot ulcer (F-non-DFU); d) alginate hydrogel-containing device that contains fibroblasts originating from the skin of the dorsum of the foot of a non-diabetic subject with no serious health issues (F-control). Healing was monitored over 10 days by daily wound tracing and is expressed as mean percentage of original wound size (day 0). Mice were euthanized at 10 days postwounding in order to collect wound tissue for histological analysis.

Figure 2:
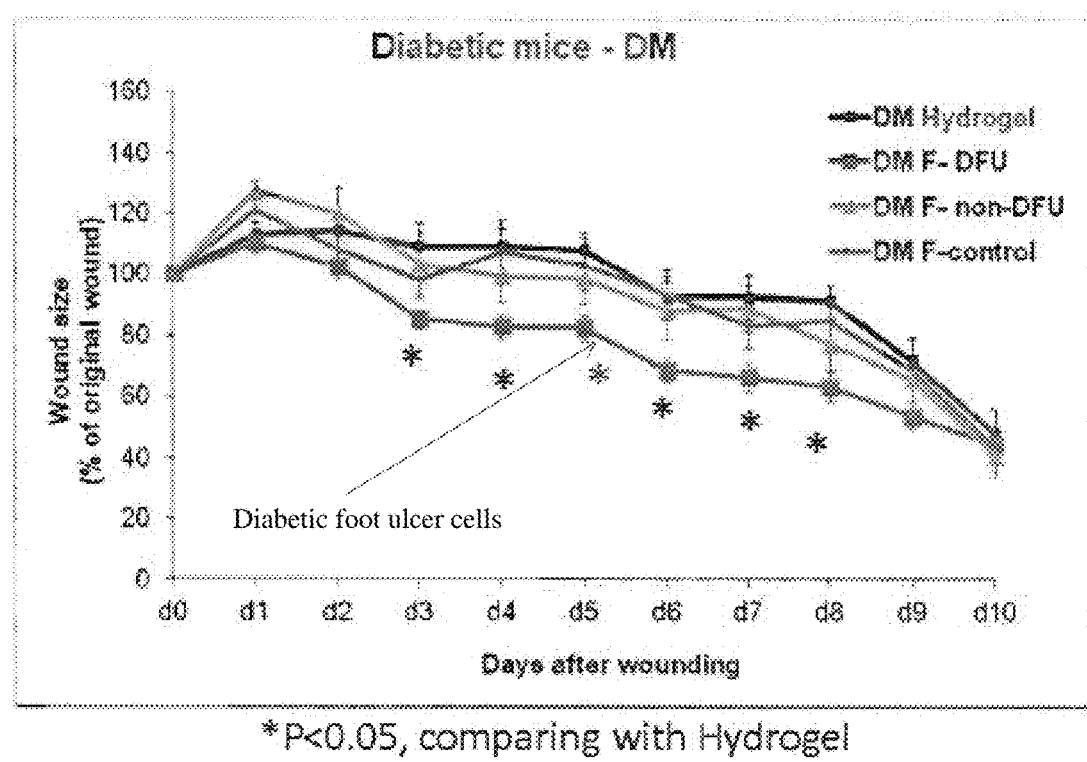
FIG. 2 is a line graph depicting the effect of hydrogels containing fibroblasts (originating from the skin area adjacent to an existing diabetic foot ulcer, originating from the skin of a foot of a diabetic subject without a foot ulcer, or originating from the skin of the foot of a non-diabetic subject) on wound size and time for wound closure in diabetic mice.

In non-diabetic mice, the best wound healing (i.e., the fastest reduction in wound size) was achieved by the alginate hydrogel that contained fibroblasts from the non-diabetic subject (FIG. 1). See, Maione et al., 2015 Tissue Engineering, 21(5): 499-508, incorporated herein by reference. In contrast, in diabetic mice, the best wound healing (i.e., the fastest reduction in wound size) was achieved by the hydrogel that contained fibroblasts taken from the skin area in or adjacent to a diabetic foot ulcer (FIG. 2). Thus, these results demonstrate that hydrogels comprising fibroblasts derived from diabetic foot ulcers lead to significantly improved diabetic wound, i.e., foot ulcer, healing compared to nondiabetic, nonulcerated foot-derived fibroblasts. As such, these results demonstrate that these diabetic foot ulcer derived fibroblasts that were previously incapable of healing the diabetic ulcer were "reprogrammed" in the presence of the hydrogel delivery vehicle to effectively heal the diabetic ulcer.

Example 2: Microarray Analysis: Diabetic Foot Ulcer-Derived Fibroblasts (DFUF) and Diabetic Non-Ulcerated Foot-Derived Fibroblasts (DFF) Exhibited Differential Gene Expression Profiles Compared to Non-Ulcerated Foot-Derived Fibroblasts (NFF)

An in vivo-like experimental model that more closely mimics the diabetic microenvironment was developed to understand how altered extracellular matrix (ECM) contributes to impaired diabetic foot ulcer (DFU). Specifically, three-dimensional (3D), skin-like tissues were developed to study the production and assembly of ECM by fibroblasts isolated from DFU (DFUFs), site-matched, non-ulcerated, diabetic skin (DFFs) and site-matched, non-ulcerated, non-diabetic skin (NFFs). This self-assembled ECM mimics the composition of early granulation tissue and is useful in studying fibroblast function during normal and abnormal healing (Maione et al., 2015 Tissue Engineering, 21(5): 499-508, incorporated herein by reference).

As described herein, this model was used to identify that phenotypic differences in ECM organization in DFU vs. DFF and DFU vs. NFF controls were related to variable responses to TGFB and in the production of fibronectin. As described below, fibronectin is an important marker expressed by DFU-derived fibroblasts and is linked to the altered wound healing manifested by these cells in vivo. These responses are also linked to the metabolic memory that cells exposed to a hyperglycemic environment manifest through changes in their ECM production and response to growth factors. The following markers are of relevance to the DFU phenotype in 2D culture and in 3D self-assembled tissues.

Fibronectin is elevated in some tissues and organs in diabetes (e.g., kidney), but prior to the invention described herein, an elevation of fibronectin has not been identified in DFU. Additionally, prior to the invention described herein, fibronectin was not associated as a marker of metabolic memory of a diabetic wound physiological microenvironment. The results described herein show that elevated fibronectin is a marker indicating that DFU-derived fibroblasts have an altered ECM phenotype which affects their ability to support proper wound healing. While there was little or no difference in fibronectin expression in a 2D system, DFUFs produced and assembled ECM in 3D tissues and were significantly enriched in fibronectin as compared to NFFs as seen by Western blot. The 3D model described herein is a complex tissue system that provides more physiologically relevant information by mimicking the in vivo environment as compared to a 2D system. These results demonstrate that the elevated production of fibronectin in DFU-derived fibroblasts (DFUF) has important functional consequences in alterations seen in chronic wound repair. These results also demonstrate that fibronectin is an important marker of DFU and is relevant to metabolic memory.

For example, the population of fibroblasts derived from diabetic foot ulcers expresses fibronectin at a level at least 1.1 fold more than nondiabetic, nonulcerated foot-derived fibroblasts, e.g., at least 1.2 fold more, at least 1.3 fold more, at least 1.4 fold more, at least 1.5 fold more, at least 1.6 fold more, at least 1.7 fold more, at least 1.8 fold more, at least 1.9 fold more, at least 2 fold more, at least 3 fold more, at least 4 fold more, at least 5 fold more, at least 6 fold more, at least 7 fold more, at least 8 fold more, at least 9 fold more, at least 10 fold more, at least 11 fold more, at least 12 fold more, at least 13 fold more, at least 14 fold more, or at least 15 fold more.

Fibronectin needs to be cleared/decreased before normal repair can proceed. The sustained expression and deposition of fibronectin prevents the progression of normal wound healing, but prior to the invention described herein, this was not studied specifically in DFU.

Smooth muscle actin is elevated in DFUFs treated with transforming growth factor beta (TGF-β). As described herein, DFUFs responded to TGF-β stimulation in 3D self-assembled tissues to activate myofibroblast phenotype through increased production of smooth muscle actin (SMA).

While DFFs and NFFs increased their fibronectin and ED-A fibronectin production in response to TGF-β, DFUFs down regulated the production of these ECM proteins. This decrease in fibronectin is a positive step towards wound healing as it needs to be cleared/decreased before normal repair can proceed. This suggests that TGF-β signaling in the DFU environment may be abnormal and may not suppress fibronectin, which could be a function of metabolic memory that is maintaining fibronectin in an elevated state.

As described herein, the results identified a trend of induction of miR-21-5p and miR-143-3p in DFUFs as compared to NFFs, whereas a trend of suppression of miR-29c-3p and miR-155-5p were shown in both DFUFs, and DFFs when compared to NFFs. This suggests these miRs are markers by which ECM and TGFβ signaling can be differentially regulated between DFUFs, DFFs and NFFs.

The mRNA sequence encoding miR-21-5p is provided by GenBank Accession No: MIMAT0000076 (incorporated herein by reference; UAGCUUAUCAGACUGAUGUUGA (SEQ ID NO: 25)). The mRNA sequence encoding miR-143-3p is provided by GenBank Accession No: MIMAT0000435 (incorporated herein by reference; UGAGAUGAAGCACUGUAGCUC (SEQ ID NO: 26)). The mRNA sequence encoding miR-29c-3p is provided by GenBank Accession No: MIMAT0000681 (incorporated herein by reference; UAGCACCAUUUGAAAUCGGUUA (SEQ ID NO: 27)). The mRNA sequence encoding miR-155-5p is provided by GenBank Accession No: MIMAT0000646 (incorporated herein by reference; UUAAUGCUAAUCGUGAUAGGGGU (SEQ ID NO: 28)).

To examine gene expression differences between diabetic foot ulcer-derived fibroblasts (DFUF), diabetic non-ulcerated foot-derived fibroblasts (DFF), and nonulcerated foot-derived fibroblasts (NFF), microarray analysis was conducted on twelve cell lines using Illumina's human BeadChip® array profiling over 47,000 transcripts (HumanHT-12 v4 Expression BeadChip Kit; Illumina, Inc; San Diego, Calif.). Unsupervised hierarchal clustering using Euclidian distance and Ward linkage was conducted to determine global differences in mRNA expression. This analysis identified 170 differentially expressed genes between DFFs and NFFs, 115 differentially expressed genes between DFUF and NFF and 58 differentially expressed genes between DFUF and DFF. Examination of differentially expressed genes revealed enrichment, i.e., increased expression, in ECM-related gene terms using gene set enrichment analysis. Specifically, Gene Ontology enRIchment anaLysis and visuaLizAtion tool (GORILLA) was used for the analysis of gene set enrichment (cbl-gorilla.cs.technion.ac.il/), while "Microarray R Us" and "R" was used to analyze the microarray data (norris.usc.libguides.com/MicroarrayRUS).

For example, the genes in the table below or the miRs described above are enriched (i.e., upregulated) in fibroblasts derived from diabetic foot ulcers at a level at least 1.1 fold more than nondiabetic, nonulcerated foot-derived fibroblasts, e.g., at least 1.2 fold more, at least 1.3 fold more, at least 1.4 fold more, at least 1.5 fold more, at least 1.6 fold more, at least 1.7 fold more, at least 1.8 fold more, at least 1.9 fold more, at least 2 fold more, at least 3 fold more, at least 4 fold more, at least 5 fold more, at least 6 fold more, at least 7 fold more, at least 8 fold more, at least 9 fold more, at least 10 fold more, at least 11 fold more, at least 12 fold more, at least 13 fold more, at least 14 fold more, at least 15 fold more, at least 20 fold more, at least 30 fold more, at least 40 fold more, at least 50 fold more, at least 60 fold more, at least 70 fold more, at least 80 fold more, at least 90 fold more, or at least 100 fold more. Alternatively, the genes in the table below or the miRs described above are downregulated in fibroblasts derived from diabetic foot ulcers at a level at least 1.1 fold less than nondiabetic, nonulcerated foot-derived fibroblasts, e.g., at least 1.2 fold less, at least 1.3 fold less, at least 1.4 fold less, at least 1.5 fold less, at least 1.6 fold less, at least 1.7 fold less, at least 1.8 fold less, at least 1.9 fold less, at least 2 fold less, at least 3 fold less, at least 4 fold less, at least 5 fold less, at least 6 fold less, at least 7 fold less, at least 8 fold less, at least 9 fold less, at least 10 fold less, at least 11 fold less, at least 12 fold less, at least 13 fold less, at least 14 fold less, at least 15 fold less, at least 20 fold less, at least 30 fold less, at least 40 fold less, at least 50 fold less, at least 60 fold less, at least 70 fold less, at least 80 fold less, at least 90 fold less, or at least 100 fold less.

This includes enrichment in gene ontology terms related to glucose metabolism supporting differences between the fibroblast groups based on diabetes status. Additionally, other processes related to wound healing, such as leukocyte chemotaxis, cell migration, cytokine production and angiogenesis, were also enriched. Several gene terms pertaining to ECM production and organization were significantly enriched in each of the three categories; biological processes, molecular functions and cellular components. The results are shown in the tables below.

| | | | Bio Process | | |
|---|---|---|---|---|---|
| GO Term | Description | P-value | FDR q-value | Enrichment | Genes |
| GO:0019682 | glyceraldehyde-3-phosphate metabolic process | 3.70E−04 | 3.23E−02 | 59.62 | [TPI1 - triosephosphate isomerase 1, TKT - transketolase] |
| GO:2000353 | positive regulation of endothelial cell apoptotic process | 2.13E−04 | 2.30E−02 | 24.39 | [AKR1C3 - aldo-keto reductase family 1, member c3, RGCC - regulator of cell cycle, COL18A1 - collagen, type xviii, alpha 1] |
| GO:0002686 | negative regulation of leukocyte migration | 5.15E−05 | 9.66E−03 | 18.83 | [GREM1 - gremlin 1, dan family bmp antagonist, APOD - apolipoprotein d, HMOX1 - heme oxygenase (decycling) 1, CCL2 - chemokine (c-c motif) ligand 2] |
| GO:0048247 | lymphocyte chemotaxis | 6.92E−04 | 4.99E−02 | 16.77 | [CXCL16 - chemokine (c-x-c motif) ligand 16, GAS6 - growth arrest-specific 6, CCL2 - chemokine (c-c motif) ligand 2] |
| GO:2000404 | regulation of T cell migration | 1.14E−04 | 1.61E−02 | 15.55 | [APOD - apolipoprotein d, TNFRSF14 - tumor necrosis factor receptor superfamily, member 14, PYCARD - pyd and card domain containing, RIPK3 - receptor-interacting serine-threonine kinase 3] |
| GO:0006096 | glycolytic process | 4.50E−07 | 4.41E−04 | 14.56 | [PFKFB4 - 6-phosphofructo-2-kinase/fructose-2,6-biphosphatase 4, PGK1 - phosphoglycerate kinase 1, TPI1 - triosephosphate isomerase 1, PFKP - phosphofructokinase, platelet, PGM1 - phosphoglucomutase 1, PGAM1 - phosphoglycerate mutase 1 (brain), ENO2 - enolase 2 (gamma, neuronal)] |
| GO:2000401 | regulation of lymphocyte migration | 2.62E−05 | 5.85E−03 | 13.97 | [APOD - apolipoprotein d, TNFRSF14 - tumor necrosis factor receptor superfamily, member 14, CCL2 - chemokine (c-c motif) ligand 2, PYCARD - pyd and card domain containing, RIPK3 - receptor-interacting serine-threonine kinase 3] |
| GO:1901655 | cellular response to ketone | 2.89E−04 | 2.84E−02 | 12.34 | [TNFSF4 - tumor necrosis factor (ligand) superfamily, member 4, GAS6 - growth arrest-specific 6, ASS1 - argininosuccinate synthase 1, AQP1 - aquaporin 1 (colton blood group)] |
| GO:0050710 | negative regulation of cytokine secretion | 3.31E−04 | 3.08E−02 | 11.92 | [RGCC - regulator of cell cycle, TNFSF4 - tumor necrosis factor (ligand) superfamily, member 4, GAS6 - growth arrest-specific 6, SRGN - serglycin] |
| GO:2000351 | regulation of endothelial cell apoptotic process | 3.77E−04 | 3.24E−02 | 11.54 | [RGCC - regulator of cell cycle, AKR1C3 - aldo-keto reductase family 1, member c3, COL18A1 - collagen, type xviii, alpha 1, GAS6 - growth arrest-specific 6] |
| GO:0030199 | collagen fibril organization | 7.95E−05 | 1.30E−02 | 11.18 | [GREM1 - gremlin 1, dan family bmp antagonist, FOXC1 - forkhead box c1, SFRP2 - secreted frizzled-related protein 2, LUM - lumican, COL11A1 - collagen, type xi, alpha 1] |
| GO:0006081 | cellular aldehyde metabolic process | 1.41E−04 | 1.80E−02 | 9.94 | [AKR1C3 - aldo-keto reductase family 1, member c3, ALDH3A1 - aldehyde dehydrogenase 3 family, member a1, ALDH3A2 - aldehyde dehydrogenase 3 family, member a2, TPI1 - triosephosphate isomerase 1, TKT - transketolase] |
| GO:0006094 | gluconeogenesis | 1.41E−04 | 1.82E−02 | 9.94 | [PGK - phosphoglycerate kinase 1, TPI1 - triosephosphate isomerase 1, PGM1 - phosphoglucomutase 1, PGAM1 - phosphoglycerate mutase 1 (brain), ENO2 - enolase 2 (gamma, neuronal)] |
| GO:0071347 | cellular response to interleukin-1 | 1.41E−04 | 1.84E−02 | 9.94 | [PTGIS - prostaglandin i2 (prostacyclin) synthase, IL1R1 - interleukin 1 receptor, type i, CCL2 - chemokine (c-c motif) ligand 2, KLF2 - kruppel-like factor 2 (lung), PYCARD - pyd and card domain containing] |

Bio Process

| GO Term | Description | P-value | FDR q-value | Enrichment | Genes |
|---|---|---|---|---|---|
| GO:0006090 | pyruvate metabolic process | 1.30E−05 | 3.68E−03 | 8.94 | [PFKFB4 - 6-phosphofructo-2-kinase/fructose-2,6-biphosphatase 4, PGK1 - phosphoglycerate kinase 1, TPI1 - triosephosphate isomerase 1, PFKP - phosphofructokinase, platelet, PGM1 - phosphoglucomutase 1, PGAM1 - phosphoglycerate mutase 1 (brain), ENO2 - enolase 2 (gamma, neuronal)] |
| GO:0030574 | collagen catabolic process | 1.88E−05 | 4.69E−03 | 8.46 | [CTSK - cathepsin k, COL8A2 - collagen, type viii, alpha 2, COL23A1 - collagen, type xxiii, alpha 1, COL4A1 - collagen, type iv, alpha 1, COL18A1 - collagen, type xviii, alpha 1, COL11A1 - collagen, type xi, alpha 1, COL15A1 - collagen, type xv, alpha 1] |
| GO:0032963 | collagen metabolic process | 3.98E−05 | 7.92E−03 | 7.54 | [CTSK - cathepsin k, COL23A1 - collagen, type xxiii, alpha 1, COL8A2 - collagen, type viii, alpha 2, COL4A1 - collagen, type iv, alpha 1, COL18A1 - collagen, type xviii, alpha 1, COL11A1 - collagen, type xi, alpha 1, COL15A1 - collagen, type xv, alpha 1] |
| GO:0002685 | regulation of leukocyte migration | 3.17E−06 | 1.39E−03 | 7.52 | [GREM1 - gremlin 1, dan family bmp antagonist, THBS4 - thrombospondin 4, APOD - apolipoprotein d, TNFRSF14 - tumor necrosis factor receptor superfamily, member 14, HMOX1 - heme oxygenase (decycling) 1, GAS6 - growth arrest-specific 6, CCL2 - chemokine (c-c motif) ligand 2, PYCARD - pyd and card domain containing, RIPK3 - receptor-interacting serine-threonine kinase 3] |
| GO:1901654 | response to ketone | 2.03E−05 | 4.98E−03 | 6.95 | [TNFSF4 - tumor necrosis factor (ligand) superfamily, member 4, DUSP1 - dual specificity phosphatase 1, SLIT3 - slit homolog 3 (drosophila), GAS6 - growth arrest-specific 6, CA9 - carbonic anhydrase ix, ASS1 - argininosuccinate synthase 1, CCL2 - chemokine (c-c motif) ligand 2, AQP1 - aquaporin 1 (colton blood group)] |
| GO:0032675 | regulation of interleukin-6 production | 2.74E−04 | 2.77E−02 | 6.71 | [TNFSF4 - tumor necrosis factor (ligand) superfamily, member 4, ADORA2B - adenosine a2b receptor, GAS6 - growth arrest-specific 6, KLF2 - kruppel-like factor 2 (lung), PYCARD - pyd and card domain containing, CARD9 - caspase recruitment domain family, member 9] |
| GO:0071456 | cellular response to hypoxia | 1.08E−04 | 1.58E−02 | 6.45 | [CITED2 - cbp/p300-interacting transactivator, with glu/asp-rich carboxy-terminal domain, 2, RGCC - regulator of cell cycle, BNIP3 - bcl2/adenovirus e1b 19 kda interacting protein 3, PTGIS - prostaglandin i2 (prostacyclin) synthase, HMOX1 - heme oxygenase (decycling) 1, CA9 - carbonic anhydrase ix, AQP1 - aquaporin 1 (colton blood group)] |
| GO:0036294 | cellular response to decreased oxygen levels | 1.23E−04 | 1.68E−02 | 6.32 | [CITED2 - cbp/p300-interacting transactivator, with glu/asp-rich carboxy-terminal domain, 2, RGCC - regulator of cell cycle, BNIP3 - bcl2/adenovirus e1b 19 kda interacting protein 3, PTGIS - prostaglandin i2 (prostacyclin) synthase, HMOX1 - heme oxygenase (decycling) 1, CA9 - carbonic anhydrase ix, AQP1 - aquaporin 1 (colton blood group)] |
| GO:0016052 | carbohydrate catabolic process | 4.80E−05 | 9.27E−03 | 6.17 | [PFKFB4 - 6-phosphofructo-2-kinase/fructose-2,6-biphosphatase 4, PGK1 - phosphoglycerate kinase 1, TPI1 - triosephosphate isomerase 1, PFKP - phosphofructokinase, platelet, PGM1 - phosphoglucomutase 1, PGAM1 - phosphoglycerate mutase 1 (brain), TKT - transketolase, ENO2 - enolase 2 (gamma, neuronal)] |

Bio Process

| GO Term | Description | P-value | FDR q-value | Enrichment | Genes |
|---|---|---|---|---|---|
| GO:0043627 | response to estrogen | 1.88E−06 | 9.98E−04 | 6.15 | [CITED2 - cbp/p300-interacting transactivator, with glu/asp-rich carboxy-terminal domain, 2, CTGF - connective tissue growth factor, WFDC1 - wap four-disulfide core domain 1, GSTM3 - glutathione s-transferase mu 3 (brain), DUSP1 - dual specificity phosphatase 1, RCAN1 - regulator of calcineurin 1, HMOX1 - heme oxygenase (decycling) 1, SMAD6 - smad family member 6, ASS1 - argininosuccinate synthase 1, AQP1 - aquaporin 1 (colton blood group), TNFRSF11B - tumor necrosis factor receptor superfamily, member 11b] |
| GO:0051224 | negative regulation of protein transport | 5.76E−05 | 1.05E−02 | 6.01 | [RGCC - regulator of cell cycle, TNFSF4 - tumor necrosis factor (ligand) superfamily, member 4, APOD - apolipoprotein d, NFKBIA - nuclear factor of kappa light polypeptide gene enhancer in b-cells inhibitor, alpha, SOX4 - sry (sex determining region y)-box 4, GAS6 - growth arrest-specific 6, SRGN - serglycin, AXIN2 - axin 2] |
| GO:0090090 | negative regulation of canonical Wnt signaling pathway | 5.49E−04 | 4.21E−02 | 5.9 | [PRICKLE1 - prickle homolog 1 (*drosophila*), GREM1 - gremlin 1, dan family bmp antagonist, SFRP2 - secreted frizzled-related protein 2, DKK3 - dickkopf wnt signaling pathway inhibitor 3, CDH2 - cadherin 2, type 1, n-cadherin (neuronal), AXIN2 - axin 2] |
| GO:0071453 | cellular response to oxygen levels | 1.99E−04 | 2.21E−02 | 5.85 | [CITED2 - cbp/p300-interacting transactivator, with glu/asp-rich carboxy-terminal domain, 2, RGCC - regulator of cell cycle, BNIP3 - bcl2/adenovirus e1b 19 kda interacting protein 3, PTGIS - prostaglandin i2 (prostacyclin) synthase, HMOX1 - heme oxygenase (decycling) 1, CA9 - carbonic anhydrase ix, AQP1 - aquaporin 1 (colton blood group)] |
| GO:0032387 | negative regulation of intracellular transport | 6.16E−04 | 4.59E−02 | 5.77 | [APOD - apolipoprotein d, HMOX1 - heme oxygenase (decycling) 1, NFKBIA - nuclear factor of kappa light polypeptide gene enhancer in b-cells inhibitor, alpha, SOX4 - sry (sex determining region y)-box 4, GAS6 - growth arrest-specific 6, AXIN2 - axin2] |
| GO:0030336 | negative regulation of cell migration | 1.37E−05 | 3.70E−03 | 5.56 | [CITED2 - cbp/p300-interacting transactivator, with glu/asp-rich carboxy-terminal domain, 2, RGCC - regulator of cell cycle, GREM1 - gremlin 1, dan family bmp antagonist, SFRP2 - secreted frizzled-related protein 2, APOD - apolipoprotein d, TPM1 - tropomyosin 1 (alpha), HMOX1 - heme oxygenase (decycling) 1, ACVRL1 - activin a receptor type ii-like 1, CCL2 - chemokine (c-c motif) ligand 2, IGFBP3 - insulin-like growth factor binding protein 3] |
| GO:0006006 | glucose metabolic process | 3.93E−05 | 7.95E−03 | 5.51 | [PFKFB4 - 6-phosphofructo-2-kinase/fructose-2,6-biphosphatase 4, PGK1 - phosphoglycerate kinase 1, APOD - apolipoprotein d, TPI1 - triosephosphate isomerase 1, PFKP - phosphofructokinase, platelet, PGM1 - phosphoglucomutase 1, PGAM1 - phosphoglycerate mutase 1 (brain), TKT - transketolase, ENO2 - enolase 2 (gamma, neuronal)] |
| GO:2000146 | negative regulation of cell motility | 1.69E−05 | 4.40E−03 | 5.42 | [CITED2 - cbp/p300-interacting transactivator, with glu/asp-rich carboxy-terminal domain, 2, RGCC - regulator of cell cycle, GREM1 - gremlin 1, dan family bmp antagonist, SFRP2 - secreted frizzled-related protein 2, APOD - apolipoprotein d, TPM1 - tropomyosin 1 (alpha), HMOX1 - heme oxygenase (decycling) 1, |

-continued

| | | Bio Process | | | |
|---|---|---|---|---|---|
| GO Term | Description | P-value | FDR q-value | Enrichment | Genes |
| GO:0022617 | extracellular matrix disassembly | 3.28E−04 | 3.12E−02 | 5.4 | ACVRL1 - activin a receptor type ii-like 1, CCL2 - chemokine (c-c motif) ligand 2, IGFBP3 - insulin-like growth factor binding protein 3] [CTSK - cathepsin k, COL23A1 - collagen, type xxiii, alpha 1, COL8A2 - collagen, type viii, alpha 2, COL4A1 - collagen, type iv, alpha 1, COL18A1 - collagen, type xviii, alpha 1, COL11A1 - collagen, type xi, alpha 1, COL15A1 - collagen, type xv, alpha 1] |
| GO:0051147 | regulation of muscle cell differentiation | 3.28E−04 | 3.09E−02 | 5.4 | [ID3 - inhibitor of dna binding 3, dominant negative helix-loop-helix protein, GREM1 - gremlin 1, dan family bmp antagonist, PRICKLE 1 - prickle homolog 1 (*drosophila*), RCAN1 - regulator of calcineurin 1, CDH2 - cadherin 2, type 1, n-cadherin (neuronal), IGFBP3 - insulin-like growth factor binding protein 3, CYP26B1 - cytochrome p450, family 26, subfamily b, polypeptide 1] |
| GO:0051271 | negative regulation of cellular component movement | 2.19E−05 | 5.27E−03 | 5.26 | [CITED2 - cbp/p300-interacting transactivator, with glu/asp-rich carboxy-terminal domain, 2, RGCC - regulator of cell cycle, GREM1 - gremlin 1, dan family bmp antagonist, SFRP2 - secreted frizzled-related protein 2, APOD - apolipoprotein d, TPM1 - tropomyosin 1 (alpha), HMOX1 - heme oxygenase (decycling) 1, ACVRL1 - activin a receptor type ii-like 1, CCL2 - chemokine (c-c motif) ligand 2, IGFBP3 - insulin-like growth factor binding protein 3] |
| GO:0030198 | extracellular matrix organization | 6.57E−10 | 8.37E−06 | 5.23 | [CTSK - cathepsin k, SFRP2 - secreted frizzled-related protein 2, FOXC1 - forkhead box c1, PLOD2 - procollagen-lysine, 2-oxoglutarate 5-dioxygenase 2, JAM2 - junctional adhesion molecule 2, COL8A2 - collagen, type viii, alpha 2, COL23A1 - collagen, type xxiii, alpha 1, COL18A1 - collagen, type xviii, alpha 1, MFAP4 - microfibrillar-associated protein 4, GREM1 - gremlin 1, dan family bmp antagonist, LUM - lumican, VIT - vitrin, CCDC80 - coiled-coil domain containing 80, ABI3BP - abi family, member 3 (nesh) binding protein, COL4A1 - collagen, type iv, alpha 1, COL11A1 - collagen, type xi, alpha 1, GAS6 - growth arrest-specific 6, FBLN2 - fibulin 2, COL15A1 - collagen, type xv, alpha 1, TNFRSF11B - tumor necrosis factor receptor superfamily, member 11b, FBLN1 - fibulin 1] |
| GO:0043062 | extracellular structure organization | 6.91E−10 | 4.40E−06 | 5.22 | [CTSK - cathepsin k, SFRP2 - secreted frizzled-related protein 2, FOXC1 - forkhead box c1, PLOD2 - procollagen-lysine, 2-oxoglutarate 5-dioxygenase 2, JAM2 - junctional adhesion molecule 2, COL8A2 - collagen, type viii, alpha 2, COL23A1 - collagen, type xxiii, alpha 1, COL18A1 - collagen, type xviii, alpha 1, MFAP4 - microfibrillar-associated protein 4, GREM1 - gremlin 1, dan family bmp antagonist, LUM - lumican, VIT - vitrin, CCDC80 - coiled-coil domain containing 80, ABI3BP - abi family, member 3 (nesh) binding protein, COL4A1 - collagen, type iv, alpha 1, COL11A1 - collagen, type xi, alpha 1, GAS6 - growth arrest-specific 6, FBLN2 - fibulin 2, COL15A1 - collagen, type xv, alpha 1, TNFRSF11B - tumor necrosis factor receptor superfamily, member 11b, FBLN1 - fibulin 1] |

| \multicolumn{6}{c}{Bio Process} |
| GO Term | Description | P-value | FDR q-value | Enrichment | Genes |
|---|---|---|---|---|---|
| GO:0031960 | response to corticosteroid | 1.63E−04 | 1.92E−02 | 5.18 | [CTGF - connective tissue growth factor, AKR1C3 - aldo-keto reductase family 1, member c3, ALDH3A1 - aldehyde dehydrogenase 3 family, member a1, DUSP1 - dual specificity phosphatase 1, SLIT3 - slit homolog 3 (*drosophila*), ASS1 - argininosuccinate synthase 1, CCL2 - chemokine (c-c motif) ligand 2, AQP1 - aquaporin 1 (colton blood group)] |
| GO:0030178 | negative regulation of Wnt signaling pathway | 4.45E−04 | 3.61E−02 | 5.13 | [APCDD1 - adenomatosis polyposis coli down-regulated 1, GREM1 - gremlin 1, dan family bmp antagonist, PRICKLE 1 - prickle homolog 1 (*drosophila*), SFRP2 - secreted frizzled-related protein 2, DKK3 - dickkopf wnt signaling pathway inhibitor 3, CDH2 - cadherin 2, type 1, n-cadherin (neuronal), AXIN2 - axin 2] |
| GO:0000302 | response to reactive oxygen species | 1.80E−04 | 2.03E−02 | 5.11 | [AKR1C3 - aldo-keto reductase family 1, member c3, BNIP3 - bcl2/adenovirus e1b 19 kda interacting protein 3, APOD - apolipoprotein d, TPM1 - tropomyosin 1 (alpha), DUSP1 - dual specificity phosphatase 1, HMOX1 - heme oxygenase (decycling) 1, KLF2 - kruppel-like factor 2 (lung), AQP1 - aquaporin 1 (colton blood group)] |
| GO:0060828 | regulation of canonical Wnt signaling pathway | 2.88E−04 | 2.84E−02 | 4.77 | [GREM1 - gremlin 1, dan family bmp antagonist, PRICKLE 1 - prickle homolog 1 (*drosophila*), SFRP2 - secreted frizzled-related protein 2, DKK3 - dickkopf wnt signaling pathway inhibitor 3, SOX4 - sry (sex determining region y)-box 4, CDH2 - cadherin 2, type 1, n-cadherin (neuronal), WLS - wntless homolog (*drosophila*), AXIN2 - axin2] |
| GO:0001818 | negative regulation of cytokine production | 3.44E−04 | 3.15E−02 | 4.65 | [RGCC - regulator of cell cycle, TNFSF4 - tumor necrosis factor (ligand) superfamily, member 4, APOD - apolipoprotein d, UBE2L6 - ubiquitin-conjugating enzyme e2l 6, HMOX1 - heme oxygenase (decycling) 1, GAS6 - growth arrest-specific 6, KLF2 - kruppel-like factor 2 (lung), PYCARD - pyd and card domain containing] |
| GO:0007584 | response to nutrient | 3.91E−04 | 3.30E−02 | 4.56 | [AKR1C3 - aldo-keto reductase family 1, member c3, ALDH3A1 - aldehyde dehydrogenase 3 family, member a1, SFRP2 - secreted frizzled-related protein 2, HMOX1 - heme oxygenase (decycling) 1, GAS6 - growth arrest-specific 6, ASS1 - argininosuccinate synthase 1, CCL2 - chemokine (c-c motif) ligand 2, TNFRSF11B - tumor necrosis factor receptor superfamily, member 11b] |
| GO:0045765 | regulation of angiogenesis | 1.73E−04 | 1.97E−02 | 4.55 | [RGCC - regulator of cell cycle, THBS4 - thrombospondin 4, SFRP2 - secreted frizzled-related protein 2, PTGIS - prostaglandin i2 (prostacyclin) synthase, HMOX1 - heme oxygenase (decycling) 1, ACVRL1 - activin a receptor type ii-like 1, F3 - coagulation factor iii (thromboplastin, tissue factor), CCL2 - chemokine (c-c motif) ligand 2, AQP1 - aquaporin 1 (colton blood group)] |
| GO:0040013 | negative regulation of locomotion | 7.66E−05 | 1.28E−02 | 4.54 | [CITED2 - cbp/p300-interacting transactivator, with glu/asp-rich carboxy-terminal domain, 2, RGCC - regulator of cell cycle, GREM1 - gremlin 1, dan family bmp antagonist, SFRP2 - secreted frizzled-related protein 2, APOD - apolipoprotein d, TPM1 - tropomyosin 1 (alpha), HMOX1 - heme oxygenase (decycling) 1, ACVRL1 - activin a receptor type ii-like 1, |

-continued

| | | | Bio Process | | |
|---|---|---|---|---|---|
| GO Term | Description | P-value | FDR q-value | Enrichment | Genes |
| GO:0019318 | hexose metabolic process | 2.13E−04 | 2.28E−02 | 4.42 | CCL2 - chemokine (c-c motif) ligand 2, IGFBP3 - insulin-like growth factor binding protein 3] [PFKFB4 - 6-phosphofructo-2-kinase/fructose-2,6-biphosphatase 4, PGK1 - phosphoglycerate kinase 1, APOD - apolipoprotein d, TPI1 - triosephosphate isomerase 1, PFKP - phosphofructokinase, platelet, PGM1 - phosphoglucomutase 1, PGAM1 - phosphoglycerate mutase 1 (brain), TKT - transketolase, ENO2 - enolase 2 (gamma, neuronal)] |
| GO:0043281 | regulation of cysteine-type endopeptidase activity involved in apoptotic process | 2.41E−04 | 2.47E−02 | 4.35 | [CTGF - connective tissue growth factor, SFRP2 - secreted frizzled-related protein 2, TNFAIP8 - tumor necrosis factor, alpha-induced protein 8, GAS6 - growth arrest-specific 6, F3 - coagulation factor iii (thromboplastin, tissue factor), MICAL1 - microtubule associated monooxygenase, calponin and lim domain containing 1, AQP1 - aquaporin 1 (colton blood group), PYCARD - pyd and card domain containing, IFI6 - interferon, alpha-inducible protein 6] |
| GO:0001933 | negative regulation of protein phosphorylation | 2.66E−05 | 5.84E−03 | 4.28 | [ERRFI1 - erbb receptor feedback inhibitor 1, GREM1 - gremlin 1, dan family bmp antagonist, SFRP2 - secreted frizzled-related protein 2, UCHL1 - ubiquitin carboxyl-terminal esterase l1 (ubiquitin thiolesterase), FAM129A - family with sequence similarity 129, member a, RGS4 - regulator of g-protein signaling 4, PPAP2B - phosphatidic acid phosphatase type 2b, DUSP1 - dual specificity phosphatase 1, SMAD6 - smad family member 6, MICAL1 - microtubule associated monooxygenase, calponin and lim domain containing 1, IGFBP3 - insulin-like growth factor binding protein 3, PYCARD - pyd and card domain containing] |
| GO:0030111 | regulation of Wnt signaling pathway | 1.25E−04 | 1.69E−02 | 4.28 | [APCDD1 - adenomatosis polyposis coli down-regulated 1, PRICKLE 1 - prickle homolog 1 (drosophila), GREM1 - gremlin 1, dan family bmp antagonist, SFRP2 - secreted frizzled-related protein 2, DKK3 - dickkopf wnt signaling pathway inhibitor 3, PPAP2B - phosphatidic acid phosphatase type 2b, SOX4 - sry (sex determining region y)-box 4, CDH2 - cadherin 2, type 1, n-cadherin (neuronal), WLS - wntless homolog (drosophila), AXIN2 - axin 2] |
| GO:0048545 | response to steroid hormone | 5.72E−07 | 4.86E−04 | 4.26 | [CITED2 - cbp/p300-interacting transactivator, with glu/asp-rich carboxy-terminal domain, 2, AKR1C3 - aldo-keto reductase family 1, member c3, GSTM3 - glutathione s-transferase mu 3 (brain), RCAN1 - regulator of calcineurin 1, SLIT3 - slit homolog 3 (drosophila), CCL2 - chemokine (c-c motif) ligand 2, ASS1 - argininosuccinate synthase 1, CTGF - connective tissue growth factor, WFDC1 - wap four-disulfide core domain 1, ALDH3A1 - aldehyde dehydrogenase 3 family, member a1, NR2F1 - nuclear receptor subfamily 2, group f, member 1, DUSP1 - dual specificity phosphatase 1, HMOX1 - heme oxygenase (decycling) 1, SMAD6 - smad family member 6, CA9 - carbonic anhydrase ix, AQP1 - aquaporin 1 (colton blood group), TNFRSF11B - tumor necrosis factor receptor superfamily, member 11b] |

-continued

Bio Process

| GO Term | Description | P-value | FDR q-value | Enrichment | Genes |
|---|---|---|---|---|---|
| GO:0001101 | response to acid chemical | 1.28E−05 | 3.69E−03 | 4.26 | [AKR1C3 - aldo-keto reductase family 1, member c3, MAP7 - microtubule-associated protein 7, AKR1C4 - aldo-keto reductase family 1, member c4, COL18A1 - collagen, type xviii, alpha 1, CCL2 - chemokine (c-c motif) ligand 2, ASS1 - argininosuccinate synthase 1, CYP26B1 - cytochrome p450, family 26, subfamily b, polypeptide 1, CTGF - connective tissue growth factor, TNFSF4 - tumor necrosis factor (ligand) superfamily, member 4, COL4A1 - collagen, type iv, alpha 1, CD9 - cd9 molecule, DUSP1 - dual specificity phosphatase 1, AQP1 - aquaporin 1 (colton blood group)] |
| GO:1901342 | regulation of vasculature development | 3.29E−04 | 3.08E−02 | 4.17 | [RGCC - regulator of cell cycle, THBS4 - thrombospondin 4, SFRP2 - secreted frizzled-related protein 2, PTGIS - prostaglandin i2 (prostacyclin) synthase, HMOX1 - heme oxygenase (decycling) 1, ACVRL1 - activin a receptor type ii-like 1, CCL2 - chemokine (c-c motif) ligand 2, F3 - coagulation factor iii (thromboplastin, tissue factor), AQP1 - aquaporin 1 (colton blood group)] |
| GO:0036293 | response to decreased oxygen levels | 9.09E−05 | 1.41E−02 | 4.07 | [CITED2 - cbp/p300-interacting transactivator, with glu/asp-rich carboxy-terminal domain, 2, CTGF - connective tissue growth factor, RGCC - regulator of cell cycle, ALDH3A1 - aldehyde dehydrogenase 3 family, member a1, BNIP3 - bcl2/adenovirus e1b 19 kda interacting protein 3, PLOD2 - procollagen-lysine, 2-oxoglutarate 5-dioxygenase 2, PTGIS - prostaglandin i2 (prostacyclin) synthase, HMOX1 - heme oxygenase (decycling) 1, CA9 - carbonic anhydrase ix, CCL2 - chemokine (c-c motif) ligand 2, AQP1 - aquaporin 1 (colton blood group)] |
| GO:0070482 | response to oxygen levels | 1.49E−04 | 1.85E−02 | 3.84 | [CITED2 - cbp/p300-interacting transactivator, with glu/asp-rich carboxy-terminal domain, 2, CTGF - connective tissue growth factor, RGCC - regulator of cell cycle, ALDH3A1 - aldehyde dehydrogenase 3 family, member a1, BNIP3 - bcl2/adenovirus e1b 19 kda interacting protein 3, PLOD2 - procollagen-lysine, 2-oxoglutarate 5-dioxygenase 2, PTGIS - prostaglandin i2 (prostacyclin) synthase, HMOX1 - heme oxygenase (decycling) 1, CA9 - carbonic anhydrase ix, CCL2 - chemokine (c-c motif) ligand 2, AQP1 - aquaporin 1 (colton blood group)] |
| GO:0001525 | angiogenesis | 3.11E−04 | 3.03E−02 | 3.82 | [CTGF - connective tissue growth factor, HAND2 - heart and neural crest derivatives expressed 2, APOD - apolipoprotein d, COL8A2 - collagen, type viii, alpha 2, COL18A1 - collagen, type xviii, alpha 1, HMOX1 - heme oxygenase (decycling) 1, ACVRL1 - activin a receptor type ii-like 1, ANPEP - alanyl (membrane) aminopeptidase, CCL2 - chemokine (c-c motif) ligand 2, COL15A1 - collagen, type xv, alpha 1] |
| GO:0001666 | response to hypoxia | 3.56E−04 | 3.20E−02 | 3.76 | [CITED2 - cbp/p300-interacting transactivator, with glu/asp-rich carboxy-terminal domain, 2, RGCC - regulator of cell cycle, ALDH3A1 - aldehyde dehydrogenase 3 family, member a1, BNIP3 - bcl2/adenovirus e1b 19 kda interacting protein 3, PLOD2 - procollagen-lysine, 2-oxoglutarate 5-dioxygenase 2, PTGIS - prostaglandin i2 |

-continued

| | Bio Process | | | | |
|---|---|---|---|---|---|
| GO Term | Description | P-value | FDR q-value | Enrichment | Genes |
| | | | | | (prostacyclin) synthase, HMOX1 - heme oxygenase (decycling) 1, CA9 - carbonic anhydrase ix, CCL2 - chemokine (c-c motif) ligand 2, AQP1 - aquaporin 1 (colton blood group)] |
| GO:0030334 | regulation of cell migration | 2.53E−07 | 2.69E−04 | 3.71 | [CITED2 - cbp/p300-interacting transactivator, with glu/asp-rich carboxy-terminal domain, 2, SFRP2 - secreted frizzled-related protein 2, TNFRSF14 - tumor necrosis factor receptor superfamily, member 14, TPM1 - tropomyosin 1 (alpha), COL18A1 - collagen, type xviii, alpha 1, ACVRL1 - activin a receptor type ii-like 1, CCL2 - chemokine (c-c motif) ligand 2, IGFBP3 - insulin-like growth factor binding protein 3, BMPER - bmp binding endothelial regulator, RGCC - regulator of cell cycle, GREM1 - gremlin 1, dan family bmp antagonist, THBS4 - thrombospondin 4, CXCL16 - chemokine (c-x-c motif) ligand 16, ENPP2 - ectonucleotide pyrophosphatase/phosphodiesterase 2, APOD - apolipoprotein d, HMOX1 - heme oxygenase (decycling) 1, GAS6 - growth arrest-specific 6, F3 - coagulation factor iii (thromboplastin, tissue factor), AQP1 - aquaporin 1 (colton blood group), PYCARD - pyd and card domain containing, RIPK3 - receptor-interacting serine-threonine kinase 3] |
| GO:0060429 | epithelium development | 5.58E−04 | 4.25E−02 | 3.55 | [ERRFI1 - erbb receptor feedback inhibitor 1, CTGF - connective tissue growth factor, APCDD1 - adenomatosis polyposis coli down-regulated 1, FOXC1 - forkhead box c1, ALDH3A2 - aldehyde dehydrogenase 3 family, member a2, TFAP2C - transcription factor ap-2 gamma (activating enhancer binding protein 2 gamma), KRT34 - keratin 34, SMAD6 - smad family member 6, AQP1 - aquaporin 1 (colton blood group), BMPER - bmp binding endothelial regulator] |
| GO:0042326 | negative regulation of phosphorylation | 1.56E−04 | 1.88E−02 | 3.55 | [ERRFI1 - erbb receptor feedback inhibitor 1, GREM1 - gremlin 1, dan family bmp antagonist, SFRP2 - secreted frizzled-related protein 2, UCHL1 - ubiquitin carboxyl-terminal esterase l1 (ubiquitin thiolesterase), FAM129A - family with sequence similarity 129, member a, RGS4 - regulator of g-protein signaling 4, PPAP2B - phosphatidic acid phosphatase type 2b, DUSP1 - dual specificity phosphatase 1, SMAD6 - smad family member 6, MICAL1 - microtubule associated monooxygenase, calponin and lim domain containing 1, IGFBP3 - insulin-like growth factor binding protein 3, PYCARD - pyd and card domain containing] |
| GO:2000145 | regulation of cell motility | 5.93E−07 | 4.72E−04 | 3.52 | [CITED2 - cbp/p300-interacting transactivator, with glu/asp-rich carboxy-terminal domain, 2, SFRP2 - secreted frizzled-related protein 2, TNFRSF14 - tumor necrosis factor receptor superfamily, member 14, TPM1 - tropomyosin 1 (alpha), COL18A1 - collagen, type xviii, alpha 1, ACVRL1 - activin a receptor type ii-like 1, CCL2 - chemokine (c-c motif) ligand 2, IGFBP3 - insulin-like growth factor binding protein 3, BMPER - bmp binding endothelial regulator, RGCC - regulator of cell cycle, GREM1 - gremlin 1, dan family bmp antagonist, THBS4 - thrombospondin 4, CXCL16 - chemokine |

| | | Bio Process | | | |
|---|---|---|---|---|---|
| GO Term | Description | P-value | FDR q-value | Enrichment | Genes |
| | | | | | (c-x-c motif) ligand 16, ENPP2 - ectonucleotide pyrophosphatase/phosphodiesterase 2, APOD - apolipoprotein d, HMOX1 - heme oxygenase (decycling) 1, GAS6 - growth arrest-specific 6, F3 - coagulation factor iii (thromboplastin, tissue factor), AQP1 - aquaporin 1 (colton blood group), PYCARD - pyd and card domain containing, RIPK3 - receptor-interacting serine-threonine kinase 3] |
| GO:0030155 | regulation of cell adhesion | 9.07E−05 | 1.43E−02 | 3.52 | [CITED2 - cbp/p300-interacting transactivator, with glu/asp-rich carboxy-terminal domain, 2, SFRP2 - secreted frizzled-related protein 2, JAM2 - junctional adhesion molecule 2, TPM1 - tropomyosin 1 (alpha), ACVRL1 - activin a receptor type ii-like 1, ASS1 - argininosuccinate synthase 1, RGCC - regulator of cell cycle, APOD - apolipoprotein d, VIT - vitrin, CCDC80 - coiled-coil domain containing 80, ABI3BP - abi family, member 3 (nesh) binding protein, NUAK1 - nuak family, snf1-like kinase, 1, FBLN2 - fibulin 2] |
| GO:0051270 | regulation of cellular component movement | 1.94E−06 | 9.90E−04 | 3.27 | [CITED2 - cbp/p300-interacting transactivator, with glu/asp-rich carboxy-terminal domain, 2, SFRP2 - secreted frizzled-related protein 2, TNFRSF14 - tumor necrosis factor receptor superfamily, member 14, TPM1 - tropomyosin 1 (alpha), COL18A1 - collagen, type xviii, alpha 1, ACVRL1 - activin a receptor type ii-like 1, CCL2 - chemokine (c-c motif) ligand 2, IGFBP3 - insulin-like growth factor binding protein 3, BMPER - bmp binding endothelial regulator, RGCC - regulator of cell cycle, GREM1 - gremlin 1, dan family bmp antagonist, THBS4 - thrombospondin 4, CXCL16 - chemokine (c-x-c motif) ligand 16, ENPP2 - ectonucleotide pyrophosphatase/phosphodiesterase 2, APOD - apolipoprotein d, HMOX1 - heme oxygenase (decycling) 1, GAS6 - growth arrest-specific 6, F3 - coagulation factor iii (thromboplastin, tissue factor), AQP1 - aquaporin 1 (colton blood group), PYCARD - pyd and card domain containing, RIPK3 - receptor-interacting serine-threonine kinase 3] |
| GO:0010942 | positive regulation of cell death | 6.57E−05 | 1.16E−02 | 3.25 | [AKR1C3 - aldo-keto reductase family 1, member c3, ID3 - inhibitor of dna binding 3, dominant negative helix-loop-helix protein, BNIP3 - bcl2/adenovirus e1b 19 kda interacting protein 3, SFRP2 - secreted frizzled-related protein 2, PAWR - prkc, apoptosis, wt1, regulator, ARHGEF3 - rho guanine nucleotide exchange factor (gef) 3, COL18A1 - collagen, type xviii, alpha 1, SOX4 - sry (sex determining region y)-box 4, IGFBP3 - insulin-like growth factor binding protein 3, CTGF - connective tissue growth factor, RGCC - regulator of cell cycle, DUSP1 - dual specificity phosphatase 1, AXIN2 - axin 2, PYCARD - pyd and card domain containing, RIPK3 - receptor-interacting serine-threonine kinase 3] |
| GO:0010035 | response to inorganic substance | 2.26E−04 | 2.36E−02 | 3.21 | [AKR1C3 - aldo-keto reductase family 1, member c3, BNIP3 - bcl2/adenovirus e1b 19 kda interacting protein 3, COL18A1 - collagen, type xviii, alpha 1, KLF2 - kruppel-like factor 2 (lung), ASS1 - argininosuccinate synthase 1, MT1M - |

-continued

| | Bio Process | | | | |
|---|---|---|---|---|---|
| GO Term | Description | P-value | FDR q-value | Enrichment | Genes |
| | | | | | metallothionein 1m, TNFSF4 - tumor necrosis factor (ligand) superfamily, member 4, CD9 - cd9 molecule, DUSP1 - dual specificity phosphatase 1, HMOX1 - heme oxygenase (decycling) 1, AQP1 - aquaporin 1 (colton blood group), CYBRD1- cytochrome b reductase 1, TNFRSF11B - tumor necrosis factor receptor superfamily, member 11b] |
| GO:0040012 | regulation of locomotion | 2.76E−06 | 1.26E−03 | 3.2 | [CITED2 - cbp/p300-interacting transactivator, with glu/asp-rich carboxy-terminal domain, 2, SFRP2 - secreted frizzled-related protein 2, TNFRSF14 - tumor necrosis factor receptor superfamily, member 14, TPM1 - tropomyosin 1 (alpha), COL18A1 - collagen, type xviii, alpha 1, ACVRL1 - activin a receptor type ii-like 1, CCL2 - chemokine (c-c motif) ligand 2, IGFBP3 - insulin-like growth factor binding protein 3, BMPER - bmp binding endothelial regulator, RGCC - regulator of cell cycle, GREM1 - gremlin 1, dan family bmp antagonist, THBS4 - thrombospondin 4, CXCL16 - chemokine (c-x-c motif) ligand 16, ENPP2 - ectonucleotide pyrophosphatase/phosphodiesterase 2, APOD - apolipoprotein d, HMOX1 - heme oxygenase (decycling) 1, GAS6 - growth arrest-specific 6, F3 - coagulation factor iii (thromboplastin, tissue factor), AQP1 - aquaporin 1 (colton blood group), PYCARD - pyd and card domain containing, RIPK3 - receptor-interacting serine-threonine kinase 3] |
| GO:0001817 | regulation of cytokine production | 9.31E−05 | 1.43E−02 | 3.01 | [UBE2L6 - ubiquitin-conjugating enzyme e2l 6, TNFRSF14 - tumor necrosis factor receptor superfamily, member 14, HLA-DPA1 - major histocompatibility complex, class ii, dp alpha 1, NFKBIA - nuclear factor of kappa light polypeptide gene enhancer in b-cells inhibitor, alpha, SRGN - serglycin, CCL2 - chemokine (c-c motif) ligand 2, KLF2 - kruppel-like factor 2 (lung), CARD9 - caspase recruitment domain family, member 9, RGCC - regulator of cell cycle, TNFSF4 - tumor necrosis factor (ligand) superfamily, member 4, ADORA2B - adenosine a2b receptor, APOD - apolipoprotein d, HMOX1 - heme oxygenase (decycling) 1, GAS6 - growth arrest-specific 6, PYCARD - pyd and card domain containing, RIPK3 - receptor-interacting serine-threonine kinase 3] |
| GO:0043068 | positive regulation of programmed cell death | 4.29E−04 | 3.52E−02 | 3 | [AKR1C3 - aldo-keto reductase family 1, member c3, ID3 - inhibitor of dna binding 3, dominant negative helix-loop-helix protein, BNIP3 - bcl2/adenovirus e1b 19 kda interacting protein 3, SFRP2 - secreted frizzled-related protein 2, PAWR - prkc, apoptosis, wt1, regulator, ARHGEF3 - rho guanine nucleotide exchange factor (gef) 3, COL18A1 - collagen, type xviii, alpha 1, SOX4 - sry (sex determining region y)-box 4, IGFBP3 - insulin-like growth factor binding protein 3, RGCC - regulator of cell cycle, DUSP1 - dual specificity phosphatase 1, PYCARD - pyd and card domain containing, RIPK3 - receptor-interacting serine-threonine kinase 3] |
| GO:0008283 | cell proliferation | 6.05E−05 | 1.09E−02 | 2.77 | [CITED2 - cbp/p300-interacting transactivator, with glu/asp-rich carboxy-terminal domain, 2, MAP7 - microtubule- |

-continued

| | | Bio Process | | | |
|---|---|---|---|---|---|
| GO Term | Description | P-value | FDR q-value | Enrichment | Genes |
| | | | | | associated protein 7, FOXC1 - forkhead box c1, SFRP2 - secreted frizzled-related protein 2, UCHL1 - ubiquitin carboxyl-terminal esterase l1 (ubiquitin thiolesterase), COL8A2 - collagen, type viii, alpha 2, SOX4 - sry (sex determining region y)-box 4, ACVRL1 - activin a receptor type ii-like 1, IGFBP3 - insulin-like growth factor binding protein 3, BMPER - bmp binding endothelial regulator, CTGF - connective tissue growth factor, TNFSF4 - tumor necrosis factor (ligand) superfamily, member 4, HAND2 - heart and neural crest derivatives expressed 2, TFAP2C - transcription factor ap-2 gamma (activating enhancer binding protein 2 gamma), HMOX1 - heme oxygenase (decycling) 1, OSR2 - odd-skipped related 2 (*drosophila*), GAS6 - growth arrest-specific 6, AXIN2 - axin2, BCAT1 - branched chain amino-acid transaminase 1, cytosolic] |
| GO:0008285 | negative regulation of cell proliferation | 1.14E−04 | 1.59E−02 | 2.73 | [SFRP2 - secreted frizzled-related protein 2, ADAMTS1 - adam metallopeptidase with thrombospondin type 1 motif, 1, PAWR - prkc, apoptosis, wt1, regulator, TNFRSF14 - tumor necrosis factor receptor superfamily, member 14, COL18A1 - collagen, type xviii, alpha 1, SLIT3 - slit homolog 3 (*drosophila*), SOX4 - sry (sex determining region y)-box 4, ACVRL1 - activin a receptor type ii-like 1, IGFBP3 - insulin-like growth factor binding protein 3, WFDC1 - wap four-disulfide core domain 1, RGCC - regulator of cell cycle, GREM1 - gremlin 1, dan family bmp antagonist, APOD - apolipoprotein d, CD9 - cd9 molecule, HMOX1 - heme oxygenase (decycling) 1, SMAD6 - smad family member 6, AXIN2 - axin 2, GAS1 - growth arrest-specific 1] |
| GO:0048468 | cell development | 6.35E−04 | 4.70E−02 | 2.63 | [CITED2 - cbp/p300-interacting transactivator, with glu/asp-rich carboxy-terminal domain, 2, MAP7 - microtubule-associated protein 7, SFRP2 - secreted frizzled-related protein 2, FOXC1 - forkhead box c1, UCHL1 - ubiquitin carboxyl-terminal esterase l1 (ubiquitin thiolesterase), GSTM3 - glutathione s-transferase mu 3 (brain), SHROOM3 - shroom family member 3, RCAN1 - regulator of calcineurin 1, SOX4 - sry (sex determining region y)-box 4, HAND2 - heart and neural crest derivatives expressed 2, TFAP2C - transcription factor ap-2 gamma (activating enhancer binding protein 2 gamma), CD9 - cd9 molecule, HSPA2 - heat shock 70 kda protein 2, COL11A1 - collagen, type xi, alpha 1, FHL2 - four and a half lim domains 2] |
| GO:0008284 | positive regulation of cell proliferation | 9.52E−05 | 1.44E−02 | 2.52 | [AKR1C3 - aldo-keto reductase family 1, member c3, SFRP2 - secreted frizzled-related protein 2, COL18A1 - collagen, type xviii, alpha 1, HLA-DPA1 - major histocompatibility complex, class ii, dp alpha 1, SOX4 - sry (sex determining region y)-box 4, ACVRL1 - activin a receptor type ii-like 1, CCL2 - chemokine (c-c motif) ligand 2, CTGF - connective tissue growth factor, GREM1 - gremlin 1, dan family bmp antagonist, ALDH3A1 - aldehyde dehydrogenase 3 family, member a1, THBS4 - thrombospondin 4, TNFSF4 - tumor necrosis factor (ligand) superfamily, member 4, HMOX1 - heme |

-continued

| | | Bio Process | | | |
|---|---|---|---|---|---|
| GO Term | Description | P-value | FDR q-value | Enrichment | Genes |
| | | | | | oxygenase (decycling) 1, OSR2 - odd-skipped related 2 (*drosophila*), GAS6 - growth arrest-specific 6, TNS3 - tensin 3, F3 - coagulation factor iii (thromboplastin, tissue factor), MARCKSL1 - marcks-like 1, GAS1 - growth arrest-specific 1, AQP1 - aquaporin 1 (colton blood group), PYCARD - pyd and card domain containing] |
| GO:0016477 | cell migration | 3.85E−04 | 3.27E−02 | 2.47 | [SORBS2 - sorbin and sh3 domain containing 2, APCDD1 - adenomatosis polyposis coli down-regulated 1, FOXC1 - forkhead box c1, JAM2 - junctional adhesion molecule 2, ACVRL1 - activin a receptor type ii-like 1, PROS 1 - protein s (alpha), CDH2 - cadherin 2, type 1, n-cadherin (neuronal), CCL2 - chemokine (c-c motif) ligand 2, CENPV - centromere protein v, CTGF - connective tissue growth factor, GREM1 - gremlin 1, dan family bmp antagonist, THBS4 - thrombospondin 4, CXCL16 - chemokine (c-x-c motif) ligand 16, HAND2 - heart and neural crest derivatives expressed 2, NR2F1 - nuclear receptor subfamily 2, group f, member 1, PPAP2B - phosphatidic acid phosphatase type 2b, GAS6 - growth arrest-specific 6, TNS3 - tensin 3] |
| GO:0042127 | regulation of cell proliferation | 5.13E−07 | 4.67E−04 | 2.44 | [AKR1C3 - aldo-keto reductase family 1, member c3, ADAMTS1 - adam metallopeptidase with thrombospondin type 1 motif, 1, PAWR - prkc, apoptosis, wt1, regulator, COL18A1 - collagen, type xviii, alpha 1, ACVRL1 - activin a receptor type ii-like 1, CTGF - connective tissue growth factor, RGCC - regulator of cell cycle, WFDC1 - wap four-disulfide core domain 1, TNFSF4 - tumor necrosis factor (ligand) superfamily, member 4, HAND2 - heart and neural crest derivatives expressed 2, CD9 - cd9 molecule, TNS3 - tensin 3, AXIN2 - axin 2, PYCARD - pyd and card domain containing, RIPK3 - receptor-interacting serine-threonine kinase 3, SFRP2 - secreted frizzled-related protein 2, TNFRSF14 - tumor necrosis factor receptor superfamily, member 14, HLA-DPA1 - major histocompatibility complex, class ii, dp alpha 1, SLIT3 - slit homolog 3 (*drosophila*), NFKBIA - nuclear factor of kappa light polypeptide gene enhancer in b-cells inhibitor, alpha, SOX4 - sry (sex determining region y)-box 4, CCL2 - chemokine (c-c motif) ligand 2, IGFBP3 - insulin-like growth factor binding protein 3, GREM1 - gremlin 1, dan family bmp antagonist, ALDH3A1 - aldehyde dehydrogenase 3 family, member a1, THBS4 - thrombospondin 4, APOD - apolipoprotein d, NUAK1 - nuak family, snf1-like kinase, 1, OSR - odd-skipped related 2 (*drosophila*), HMOX1 - heme oxygenase (decycling) 1, SMAD6 - smad family member 6, GAS6 - growth arrest-specific 6, F3 - coagulation factor iii (thromboplastin, tissue factor), MARCKSL1 - marcks-like 1, GAS1 - growth arrest-specific 1, AQP1 - aquaporin 1 (colton blood group)] |
| GO:0023057 | negative regulation of signaling | 8.06E−05 | 1.30E−02 | 2.36 | [ERRFI1 - erbb receptor feedback inhibitor 1, APCDD1 - adenomatosis polyposis coli down-regulated 1, SFRP2 - secreted frizzled-related protein 2, UCHL1 - ubiquitin carboxyl-terminal esterase l1 |

Bio Process

| GO Term | Description | P-value | FDR q-value | Enrichment | Genes |
|---|---|---|---|---|---|
| | | | | | (ubiquitin thiolesterase), PAWR - prkc, apoptosis, wt1, regulator, SLIT3 - slit homolog 3 (*drosophila*), NFKBIA - nuclear factor of kappa light polypeptide gene enhancer in b-cells inhibitor, alpha, CDH2 - cadherin 2, type 1, n-cadherin (neuronal), CYP26B1 - cytochrome p450, family 26, subfamily b, polypeptide 1, IGFBP3 - insulin-like growth factor binding protein 3, BMPER - bmp binding endothelial regulator, PRICKLE 1 - prickle homolog 1 (*drosophila*), GREM1 - gremlin 1, dan family bmp antagonist, DKK3 - dickkopf wnt signaling pathway inhibitor 3, APOD - apolipoprotein d, RGS4 - regulator of g-protein signaling 4, DUSP1 - dual specificity phosphatase 1, HMOX1 - heme oxygenase (decycling) 1, SMAD6 - smad family member 6, GAS6 - growth arrest-specific 6, AXIN2 - axin 2, GAS1 - growth arrest-specific 1, PYCARD - pyd and card domain containing, IFI6 - interferon, alpha-inducible protein 6] |
| GO:0010648 | negative regulation of cell communication | 8.34E−05 | 1.33E−02 | 2.36 | [ERRFI1 - erbb receptor feedback inhibitor 1, APCDD1 - adenomatosis polyposis coli down-regulated 1, SFRP2 - secreted frizzled-related protein 2, UCHL1 - ubiquitin carboxyl-terminal esterase l1 (ubiquitin thiolesterase), PAWR - prkc, apoptosis, wt1, regulator, SLIT3 - slit homolog 3 (*drosophila*), NFKBIA - nuclear factor of kappa light polypeptide gene enhancer in b-cells inhibitor, alpha, CDH2 - cadherin 2, type 1, n-cadherin (neuronal), CYP26B1 - cytochrome p450, family 26, subfamily b, polypeptide 1, IGFBP3 - insulin-like growth factor binding protein 3, BMPER - bmp binding endothelial regulator, PRICKLE 1 - prickle homolog 1 (*drosophila*), GREM1 - gremlin 1, dan family bmp antagonist, DKK3 - dickkopf wnt signaling pathway inhibitor 3, APOD - apolipoprotein d, RGS4 - regulator of g-protein signaling 4, DUSP1 - dual specificity phosphatase 1, HMOX1 - heme oxygenase (decycling) 1, SMAD6 - smad family member 6, GAS6 - growth arrest-specific 6, AXIN2 - axin 2, GAS1 - growth arrest-specific 1, PYCARD - pyd and card domain containing, IFI6 - interferon, alpha-inducible protein 6] |
| GO:0060548 | negative regulation of cell death | 4.72E−04 | 3.73E−02 | 2.36 | [CITED2 - cbp/p300-interacting transactivator, with glu/asp-rich carboxy-terminal domain, 2, BNIP3 - bcl2/adenovirus e1b 19 kda interacting protein 3, FOXC1 - forkhead box c1, SFRP2 - secreted frizzled-related protein 2, EGR2 - early growth response 2, NFKBIA - nuclear factor of kappa light polypeptide gene enhancer in b-cells inhibitor, alpha, SOX4 - sry (sex determining region y)-box 4, MICAL1 - microtubule associated monooxygenase, calponin and lim domain containing 1, CCL2 - chemokine (c-c motif) ligand 2, CTGF - connective tissue growth factor, HAND2 - heart and neural crest derivatives expressed 2, TNFAIP8 - tumor necrosis factor, alpha-induced protein 8, DUSP1 - dual specificity phosphatase 1, HMOX1 - heme oxygenase (decycling) 1, SMAD6 - smad family member 6, GAS6 - growth arrest-specific 6, FHL2 - four and a |

-continued

| | | Bio Process | | | |
|---|---|---|---|---|---|
| GO Term | Description | P-value | FDR q-value | Enrichment | Genes |
| GO:0009605 | response to external stimulus | 3.86E−06 | 1.59E−03 | 2.3 | half lim domains 2, GAS1 - growth arrest-specific 1, AQP1 - aquaporin 1 (colton blood group)] [CITED2 - cbp/p300-interacting transactivator, with glu/asp-rich carboxy-terminal domain, 2, AKR1C3 - aldo-keto reductase family 1, member c3, BNIP3 - bcl2/adenovirus e1b 19 kda interacting protein 3, SHROOM3 - shroom family member 3, BAIAP2L1 - bai1-associated protein 2-like 1, RCAN1 - regulator of calcineurin 1, TNFSF4 - tumor necrosis factor (ligand) superfamily, member 4, ENPP2 - ectonucleotide pyrophosphatase/phosphodiesterase 2, CXCL16 - chemokine (c-x-c motif) ligand 16, MX1 - myxovirus (influenza virus) resistance 1, interferon-inducible protein p78 (mouse), COTL1 - coactosin-like 1 (dictyostelium), OAS2 - 2'-5'-oligoadenylate synthetase 2, 69/71 kda, PYCARD - pyd and card domain containing, BHLHE40 - basic helix-loop-helix family, member e40, SFRP2 - secreted frizzled-related protein 2, AKR1C4 - aldo-keto reductase family 1, member c4, TNFRSF14 - tumor necrosis factor receptor superfamily, member 14, PENK - proenkephalin, SLIT3 - slit homolog 3 (*drosophila*), NFKBIA - nuclear factor of kappa light polypeptide gene enhancer in b-cells inhibitor, alpha, ASS1 - argininosuccinate synthase 1, CCL2 - chemokine (c-c motif) ligand 2, CARD9 - caspase recruitment domain family, member 9, ALDH3A1 - aldehyde dehydrogenase 3 family, member a1, ADORA2B - adenosine a2b receptor, RDH5 - retinol dehydrogenase 5 (11-cis/9-cis), TNFAIP8 - tumor necrosis factor, alpha-induced protein 8, HMOX1 - heme oxygenase (decycling) 1, IFI44 - interferon-induced protein 44, COL11A1 - collagen, type xi, alpha 1, GAS6 - growth arrest-specific 6, ANPEP - alanyl (membrane) aminopeptidase, AQP1 - aquaporin 1 (colton blood group), TNFRSF11B - tumor necrosis factor receptor superfamily, member 11b] |
| GO:1901700 | response to oxygen-containing compound | 2.31E−05 | 5.36E−03 | 2.3 | [AKR1C3 - aldo-keto reductase family 1, member c3, BNIP3 - bcl2/adenovirus e1b 19 kda interacting protein 3, MAP7 - microtubule-associated protein 7, TPM1 - tropomyosin 1 (alpha), COL18A1 - collagen, type xviii, alpha 1, KLF2 - kruppel-like factor 2 (lung), CYP26B1 - cytochrome p450, family 26, subfamily b, polypeptide 1, CTGF - connective tissue growth factor, WFDC1 - wap four-disulfide core domain 1, TNFSF4 - tumor necrosis factor (ligand) superfamily, member 4, CD9 - cd9 molecule, COL4A1 - collagen, type iv, alpha 1, CA9 - carbonic anhydrase ix, PYCARD - pyd and card domain containing, AKR1C4 - aldo-keto reductase family 1, member c4, SLIT3 - slit homolog 3 (*drosophila*), EGR2 - early growth response 2, NFKBIA - nuclear factor of kappa light polypeptide gene enhancer in b-cells inhibitor, alpha, SOX4 - sry (sex determining region y)-box 4, ASS1 - argininosuccinate synthase 1, CCL2 - chemokine (c-c motif) ligand 2, CARD9 - caspase recruitment domain family, member 9, ALDH3A1 - aldehyde dehydrogenase 3 family, member a1, APOD - |

Bio Process

| GO Term | Description | P-value | FDR q-value | Enrichment | Genes |
|---|---|---|---|---|---|
| | | | | | apolipoprotein d, DUSP1 - dual specificity phosphatase 1, HMOX1 - heme oxygenase (decycling) 1, GAS6 - growth arrest-specific 6, AQP1 - aquaporin 1 (colton blood group), ADCY4 - adenylate cyclase 4] |
| GO:0040011 | locomotion | 3.52E−04 | 3.18E−02 | 2.29 | [APCDD1 - adenomatosis polyposis coli down-regulated 1, SORBS2 - sorbin and sh3 domain containing 2, FOXC1 - forkhead box c1, JAM2 - junctional adhesion molecule 2, RCAN1 - regulator of calcineurin 1, SLIT3 - slit homolog 3 (*drosophila*), ACVRL1 - activin a receptor type ii-like 1, PROS1 - protein s (alpha), CDH2 - cadherin 2, type 1, n-cadherin (neuronal), CCL2 - chemokine (c-c motif) ligand 2, CENPV - centromere protein v, CTGF - connective tissue growth factor, GREM1 - gremlin 1, dan family bmp antagonist, THBS4 - thrombospondin 4, HAND2 - heart and neural crest derivatives expressed 2, ENPP2 - ectonucleotide pyrophosphatase/phosphodiesterase 2, CXCL16 - chemokine (c-x-c motif) ligand 16, NR2F1 - nuclear receptor subfamily 2, group f, member 1, PPAP2B - phosphatidic acid phosphatase type 2b, GAS6 - growth arrest-specific 6, TNS3 - tensin 3] |
| GO:0042981 | regulation of apoptotic process | 1.12E−05 | 3.49E−03 | 2.26 | [CITED2 - cbp/p300-interacting transactivator, with glu/asp-rich carboxy-terminal domain, 2, AKR1C3 - aldo-keto reductase family 1, member c3, BNIP3 - bcl2/adenovirus e1b 19 kda interacting protein 3, PAWR - prkc, apoptosis, wt1, regulator, COL18A1 - collagen, type xviii, alpha 1, MICAL1 - microtubule associated monooxygenase, calponin and lim domain containing 1, CTGF - connective tissue growth factor, RGCC - regulator of cell cycle, HAND2 - heart and neural crest derivatives expressed 2, PTGIS - prostaglandin i2 (prostacyclin) synthase, PYCARD - pyd and card domain containing, RIPK3 - receptor-interacting serine-threonine kinase 3, ID3 - inhibitor of dna binding 3, dominant negative helix-loop-helix protein, FOXC1 - forkhead box c1, SFRP2 - secreted frizzled-related protein 2, ARHGEF3 - rho guanine nucleotide exchange factor (gef) 3, EGR2 - early growth response 2, NFKBIA - nuclear factor of kappa light polypeptide gene enhancer in b-cells inhibitor, alpha, SOX4 - sry (sex determining region y)-box 4, CCL2 - chemokine (c-c motif) ligand 2, IGFBP3 - insulin-like growth factor binding protein 3, CARD9 - caspase recruitment domain family, member 9, TNFAIP8 - tumor necrosis factor, alpha-induced protein 8, DUSP1 - dual specificity phosphatase 1, HMOX1 - heme oxygenase (decycling) 1, SMAD6 - smad family member 6, GAS6 - growth arrest-specific 6, FHL2 - four and a half lim domains 2, F3 - coagulation factor iii (thromboplastin, tissue factor), GAS1 - growth arrest-specific 1, AQP1 - aquaporin 1 (colton blood group), IFI6 - interferon, alpha-inducible protein 6] |
| GO:0009719 | response to endogenous stimulus | 1.61E−05 | 4.28E−03 | 2.26 | [CITED2 - cbp/p300-interacting transactivator, with glu/asp-rich carboxy-terminal domain, 2, GSTM2 - glutathione s-transferase mu 2 (muscle), AKR1C3 - |

-continued

| | | Bio Process | | | |
|---|---|---|---|---|---|
| GO Term | Description | P-value | FDR q-value | Enrichment | Genes |
| | | | | | aldo-keto reductase family 1, member c3, GSTM3 - glutathione s-transferase mu 3 (brain), RCAN1 - regulator of calcineurin 1, ACVRL1 - activin a receptor type ii-like 1, EEF1A1 - eukaryotic translation elongation factor 1 alpha 1, KLF2 - kruppel-like factor 2 (lung), CTGF - connective tissue growth factor, WFDC1 - wap four-disulfide core domain 1, TNFSF4 - tumor necrosis factor (ligand) superfamily, member 4, NR2F1 - nuclear receptor subfamily 2, group f, member 1, COL4A1 - collagen, type iv, alpha 1, CA9 - carbonic anhydrase ix, AKR1C4 - aldo-keto reductase family 1, member c4, SLIT3 - slit homolog 3 (drosophila), EGR2 - early growth response 2, NFKBIA - nuclear factor of kappa light polypeptide gene enhancer in b-cells inhibitor, alpha, ASS1 - argininosuccinate synthase 1, CCL2 - chemokine (c-c motif) ligand 2, CARD9 - caspase recruitment domain family, member 9, ALDH3A1 - aldehyde dehydrogenase 3 family, member a1, CLEC3B - c-type lectin domain family 3, member b, DUSP1 - dual specificity phosphatase 1, HMOX1 - heme oxygenase (decycling) 1, SMAD6 - smad family member 6, FHL2 - four and a half lim domains 2, AQP1 - aquaporin 1 (colton blood group), TNFRSF11B - tumor necrosis factor receptor superfamily, member 11b, ADCY4 - adenylate cyclase 4, STMN2 - stathmin-like 2] |
| GO:0007155 | cell adhesion | 4.13E−04 | 3.44E−02 | 2.26 | [SORBS2 - sorbin and sh3 domain containing 2, JAM2 - junctional adhesion molecule 2, COL8A2 - collagen, type viii, alpha 2, COL18A1 - collagen, type xviii, alpha 1, ISLR - immunoglobulin superfamily containing leucine-rich repeat, ANTXR1 - anthrax toxin receptor 1, CDH2 - cadherin 2, type 1, n-cadherin (neuronal), CCL2 - chemokine (c-c motif) ligand 2, MFAP4 - microfibrillar-associated protein 4, CTGF - connective tissue growth factor, THBS4 - thrombospondin 4, CLDN11 - claudin 11, CD9 - cd9 molecule, PPAP2B - phosphatidic acid phosphatase type 2b, NUAK1 - nuak family, snf1-like kinase, 1, CSRP1 - cysteine and glycine-rich protein 1, SMAD6 - smad family member 6, COL11A1 - collagen, type xi, alpha 1, GAS6 - growth arrest-specific 6, ALCAM - activated leukocyte cell adhesion molecule, COL15A1 - collagen, type xv, alpha 1] |
| GO:0022610 | biological adhesion | 4.33E−04 | 3.54E−02 | 2.25 | [SORBS2 - sorbin and sh3 domain containing 2, JAM2 - junctional adhesion molecule 2, COL8A2 - collagen, type viii, alpha 2, COL18A1 - collagen, type xviii, alpha 1, ISLR - immunoglobulin superfamily containing leucine-rich repeat, ANTXR1 - anthrax toxin receptor 1, CDH2 - cadherin 2, type 1, n-cadherin (neuronal), CCL2 - chemokine (c-c motif) ligand 2, MFAP4 - microfibrillar-associated protein 4, CTGF - connective tissue growth factor, THBS4 - thrombospondin 4, CLDN11 - claudin 11, CD9 - cd9 molecule, PPAP2B - phosphatidic acid phosphatase type 2b, NUAK1 - nuak family, snf1-like kinase, 1, CSRP1 - cysteine and glycine-rich protein 1, SMAD6 - smad family member 6, |

-continued

| | | Bio Process | | | |
|---|---|---|---|---|---|
| GO Term | Description | P-value | FDR q-value | Enrichment | Genes |
| GO:0043067 | regulation of programmed cell death | 1.32E−05 | 3.65E−03 | 2.24 | COL11A1 - collagen, type xi, alpha 1, GAS6 - growth arrest-specific 6, ALCAM - activated leukocyte cell adhesion molecule, COL15A1 - collagen, type xv, alpha 1]<br>[CITED2 - cbp/p300-interacting transactivator, with glu/asp-rich carboxy-terminal domain, 2, AKR1C3 - aldo-keto reductase family 1, member c3, BNIP3 - bcl2/adenovirus e1b 19 kda interacting protein 3, PAWR - prkc, apoptosis, wt1, regulator, COL18A1 - collagen, type xviii, alpha 1, MICAL1 - microtubule associated monooxygenase, calponin and lim domain containing 1, CTGF - connective tissue growth factor, RGCC - regulator of cell cycle, HAND2 - heart and neural crest derivatives expressed 2, PTGIS - prostaglandin i2 (prostacyclin) synthase, PYCARD - pyd and card domain containing, RIPK3 - receptor-interacting serine-threonine kinase 3, ID3 - inhibitor of dna binding 3, dominant negative helix-loop-helix protein, FOXC1 - forkhead box c1, SFRP2 - secreted frizzled-related protein 2, ARHGEF3 - rho guanine nucleotide exchange factor (gef) 3, EGR2 - early growth response 2, NFKBIA - nuclear factor of kappa light polypeptide gene enhancer in b-cells inhibitor, alpha, SOX4 - sry (sex determining region y)-box 4, CCL2 - chemokine (c-c motif) ligand 2, IGFBP3 - insulin-like growth factor binding protein 3, CARD9 - caspase recruitment domain family, member 9, TNFAIP8 - tumor necrosis factor, alpha-induced protein 8, DUSP1 - dual specificity phosphatase 1, HMOX1 - heme oxygenase (decycling) 1, SMAD6 - smad family member 6, GAS6 - growth arrest-specific 6, FHL2 - four and a half lim domains 2, F3 - coagulation factor iii (thromboplastin, tissue factor), GAS1 - growth arrest-specific 1, AQP1 - aquaporin 1 (colton blood group), IFI6 - interferon, alpha-inducible protein 6] |
| GO:0010941 | regulation of cell death | 1.13E−05 | 3.41E−03 | 2.23 | [CITED2 - cbp/p300-interacting transactivator, with glu/asp-rich carboxy-terminal domain, 2, AKR1C3 - aldo-keto reductase family 1, member c3, BNIP3 - bcl2/adenovirus e1b 19 kda interacting protein 3, PAWR - prkc, apoptosis, wt1, regulator, COL18A1 - collagen, type xviii, alpha 1, MICAL1 - microtubule associated monooxygenase, calponin and lim domain containing 1, CTGF - connective tissue growth factor, RGCC - regulator of cell cycle, HAND2 - heart and neural crest derivatives expressed 2, PTGIS - prostaglandin i2 (prostacyclin) synthase, AXIN2 - axin 2, PYCARD - pyd and card domain containing, RIPK3 - receptor-interacting serine-threonine kinase 3, ID3 - inhibitor of dna binding 3, dominant negative helix-loop-helix protein, FOXC1 - forkhead box c1, SFRP2 - secreted frizzled-related protein 2, ARHGEF3 - rho guanine nucleotide exchange factor (gef) 3, EGR2 - early growth response 2, NFKBIA - nuclear factor of kappa light polypeptide gene enhancer in b-cells inhibitor, alpha, SOX4 - sry (sex determining region y)-box 4, CCL2 - chemokine (c-c motif) ligand 2, IGFBP3 - insulin-like growth factor binding protein 3, CARD9 - caspase |

-continued

| Bio Process | | | | | |
|---|---|---|---|---|---|
| GO Term | Description | P-value | FDR q-value | Enrichment | Genes |
| | | | | | recruitment domain family, member 9, TNFAIP8 - tumor necrosis factor, alpha-induced protein 8, DUSP1 - dual specificity phosphatase 1, HMOX1 - heme oxygenase (decycling) 1, SMAD6 - smad family member 6, GAS6 - growth arrest-specific 6, FHL2 - four and a half lim domains 2, F3 - coagulation factor iii (thromboplastin, tissue factor), GAS1 - growth arrest-specific 1, AQP1 - aquaporin 1 (colton blood group), IFI6 - interferon, alpha-inducible protein 6] |

Molecular Function

| GO Term | Description | P-value | FDR q-value | Enrichment | Genes |
|---|---|---|---|---|---|
| GO:0001968 | fibronectin binding | 7.36E−06 | 3.00E−02 | 17.89 | CTGF, CTSK, SFRP2, CCDC80, IGFBP3 |
| GO:0005201 | extracellular matrix structural constituent | 1.07E−05 | 2.18E−02 | 9.21 | LUM, COL8A2, COL4A1, COL11A1, FBLN2, COL15A1, FBLN1 |

Cellular Component

| GO Term | Description | P-value | FDR q-value | Enrichment | Genes |
|---|---|---|---|---|---|
| GO:0005604 | basement membrane | 1.57E−05 | 2.29E−03 | 8.7 | [THBS4 - thrombospondin 4, ADAMTS1 - adam metallopeptidase with thrombospondin type 1 motif, 1, COL8A2 - collagen, type viii, alpha 2, CCDC80 - coiled-coil domain containing 80, COL4A1 - collagen, type iv, alpha 1, COL18A1 - collagen, type xviii, alpha 1, FBLN1 - fibulin 1] |
| GO:0044420 | extracellular matrix part | 1.34E−07 | 2.45E−05 | 8 | [THBS4 - thrombospondin 4, LUM - lumican, ADAMTS1 - adam metallopeptidase with thrombospondin type 1 motif, 1, COL8A2 - collagen, type viii, alpha 2, CCDC80 - coiled-coil domain containing 80, COL4A1 - collagen, type iv, alpha 1, COL18A1 - collagen, type xviii, alpha 1, COL11A1 - collagen, type xi, alpha 1, COL15A1 - collagen, type xv, alpha 1, FBLN1 - fibulin 1, MFAP4 - microfibrillar-associated protein 4] |
| GO:0005581 | collagen trimer | 5.80E−05 | 7.73E−03 | 7.11 | [LUM - lumican, COL8A2 - collagen, type viii, alpha 2, COL23A1 - collagen, type xxiii, alpha 1, COL4A1 - collagen, type iv, alpha 1, COL18A1 - collagen, type xviii, alpha 1, COL11A1 - collagen, type xi, alpha 1, COL15A1 - collagen, type xv, alpha 1] |
| GO:0031012 | extracellular matrix | 2.66E−07 | 4.33E−05 | 4.5 | [SFRP2 - secreted frizzled-related protein 2, COL8A2 - collagen, type viii, alpha 2, COL18A1 - collagen, type xviii, alpha 1, MFAP4 - microfibrillar-associated protein 4, CTGF - connective tissue growth factor, THBS4 - thrombospondin 4, LUM - lumican, CLEC3B - c-type lectin domain family 3, member b, VIT - vitrin, CCDC80 - coiled-coil domain containing 80, COL4A1 - collagen, type iv, alpha 1, ABI3BP - abi family, member 3 (nesh) binding protein, F3 - coagulation factor iii (thromboplastin, tissue factor), |

| GO Term | Description | P-value | FDR q-value | Enrichment | Genes |
|---|---|---|---|---|---|
| GO:0005788 | endoplasmic reticulum lumen | 2.04E−04 | 2.31E−02 | 4.45 | FBLN2 - fibulin2, COL15A1 - collagen, type xv, alpha 1, FBLN1 - fibulin 1, TNFRSF11B - tumor necrosis factor receptor superfamily, member 11b] [RDH5 - retinol dehydrogenase 5 (11-cis/9-cis), GPX7 - glutathione peroxidase 7, COL23A1 - collagen, type xxiii, alpha 1, COL8A2 - collagen, type viii, alpha 2, COL4A1 - collagen, type iv, alpha 1, COL18A1 - collagen, type xviii, alpha 1, COL11A1 - collagen, type xi, alpha 1, GAS6 - growth arrest-specific 6, COL15A1 - collagen, type xv, alpha 1] |
| GO:0005615 | extracellular space | 3.94E−10 | 2.89E−07 | 3.09 | [LOXL4 - lysyl oxidase-like 4, TPI1 - triosephosphate isomerase 1, KRT34 - keratin 34, COL18A1 - collagen, type xviii, alpha 1, EEF1A1 - eukaryotic translation elongation factor 1 alpha 1, PROS1 - protein s (alpha), SRGN - serglycin, CTGF - connective tissue growth factor, WFDC1 - wap four-disulfide core domain 1, TNFSF4 - tumor necrosis factor (ligand) superfamily, member 4, LUM - lumican, ENPP2 - ectonucleotide pyrophosphatase/phosphodiesterase 2, CXCL16 - chemokine (c-x-c motif) ligand 16, DKK3 - dickkopf wnt signaling pathway inhibitor 3, PTGIS - prostaglandin i2 (prostacyclin) synthase, CD9 - cd9 molecule, ENO2 - enolase 2 (gamma, neuronal), FBLN1 - fibulin 1, CTSK - cathepsin k, SFRP2 - secreted frizzled-related protein 2, CFB - complement factor b, SLIT3 - slit homolog 3 (*drosophila*), CTSZ - cathepsin z, CCL2 - chemokine (c-c motif) ligand 2, IGFBP3 - insulin-like growth factor binding protein 3, BMPER - bmp binding endothelial regulator, GREM1 - gremlin 1, dan family bmp antagonist, ALDH3A1 - aldehyde dehydrogenase 3 family, member a1, THBS4 - thrombospondin 4, CLEC3B - c-type lectin domain family 3, member b, APOD - apolipoprotein d, ABI3BP - abi family, member 3 (nesh) binding protein, HMOX1 - heme oxygenase (decycling) 1, ANPEP - alanyl (membrane) aminopeptidase, GAS6 - growth arrest-specific 6, F3 - coagulation factor iii (thromboplastin, tissue factor), COL15A1 - collagen, type xv, alpha 1, TNFRSF11B - tumor necrosis factor receptor superfamily, member 11b] |
| GO:0044432 | endoplasmic reticulum part | 3.38E−04 | 3.53E−02 | 2.15 | [LSS - lanosterol synthase (2,3-oxidosqualene-lanosterol cyclase), MOXD1 - monooxygenase, dbh-like 1, KCNK2 - potassium channel, subfamily k, member 2, PLOD2 - procollagen-lysine, 2-oxoglutarate 5-dioxygenase 2, COL23A1 - collagen, type xxiii, alpha 1, UCHL1 - ubiquitin carboxyl-terminal esterase l1 (ubiquitin thiolesterase), COL8A2 - collagen, type viii, alpha 2, COL18A1 - collagen, type xviii, alpha 1, HLA-DPA1 - major histocompatibility complex, class ii, dp alpha 1, PROS1 - protein s (alpha), CYP26B1 - cytochrome p450, family 26, subfamily b, polypeptide 1, ALDH3A2 - aldehyde dehydrogenase 3 family, member a2, EPHX1 - epoxide hydrolase 1, microsomal (xenobiotic), GPX7 - glutathione peroxidase 7, CPT1C - carnitine palmitoyltransferase 1c, RDH5 - retinol dehydrogenase 5 (11-cis/9-cis), MX1 - myxovirus (influenza virus) |

| GO Term | Description | P-value | FDR q-value | Enrichment | Genes |
|---|---|---|---|---|---|
| | | | | | resistance 1, interferon-inducible protein p78 (mouse), PTGIS - prostaglandin i2 (prostacyclin) synthase, COL4A1 - collagen, type iv, alpha 1, HMOX1 - heme oxygenase (decycling) 1, COL11A1 - collagen, type xi, alpha 1, GAS6 - growth arrest-specific 6, PLA2G4C - phospholipase a2, group ivc (cytosolic, calcium-independent), COL15A1 - collagen, type xv, alpha 1] |
| GO:0044421 | extracellular region part | 2.65E-13 | 3.89E-10 | 2.14 | SCPEP1, GSTM2, AKR1C3, PGK1, LOXL4, PGM1, GSTM3, COL18A1, PGA5, PGAM1 - phosphoglycerate mutase 1 (brain), ANTXR1 - anthrax toxin receptor 1, TKT - transketolase, SRGN - serglycin, CDH2 - cadherin 2, type 1, n-cadherin (neuronal), CTGF - connective tissue growth factor, DKK3 - dickkopf wnt signaling pathway inhibitor 3, CLDN11 - claudin 11, CCDC80 - coiled-coil domain containing 80, GSTT2 - glutathione s-transferase theta 2, COTL1 - coactosin-like 1 (dictyostelium), ENO2 - enolase 2 (gamma, neuronal), FBLN1 - fibulin 1, CTSK - cathepsin k, AKR1C4 - aldo-keto reductase family 1, member c4, PLOD2 - procollagen-lysine, 2-oxoglutarate 5-dioxygenase 2, CFB - complement factor b, CTSZ - cathepsin z, CCL2 - chemokine (c-c motif) ligand 2, ALDH3A1 - aldehyde dehydrogenase 3 family, member a 1, GREM1 - gremlin 1, dan family bmp antagonist, CLEC3B - c-type lectin domain family 3, member b, ALDH3A2 - aldehyde dehydrogenase 3 family, member a2, VIT - vitrin, APOD - apolipoprotein d, PFKP - phosphofructokinase, platelet, ABI3BP - abi family, member 3 (nesh) binding protein, MYO1D - myosin id, MARCKSL1 - marcks-like 1, F3 - coagulation factor iii (thromboplastin, tissue factor), ALCAM - activated leukocyte cell adhesion molecule, AQP1 - aquaporin 1 (colton blood group), TNFRSF11B - tumor necrosis factor receptor superfamily, member 11b, ADAMTS1 - adam metallopeptidase with thrombospondin type 1 motif, 1, TPI1 - triosephosphate isomerase 1, KRT34 - keratin 34, BAIAP2L1 - bai1-associated protein 2-like 1, EEF1A1 - eukaryotic translation elongation factor 1 alpha 1, ISLR - immunoglobulin superfamily containing leucine-rich repeat, PROS1 - protein s (alpha), WFDC1 - wap four-disulfide core domain 1, SERINC2 - serine incorporator 2, TNFSF4 - tumor necrosis factor (ligand) superfamily, member 4, CXCL16 - chemokine (c-x-c motif) ligand 16, ENPP2 - ectonucleotide pyrophosphatase/phosphodiesterase 2, LUM - lumican, ACYP1 - acylphosphatase 1, erythrocyte (common) type, PTGIS - prostaglandin i2 (prostacyclin) synthase, COL4A1 - collagen, type iv, alpha 1, CD9 - cd9 molecule, TUBB6 - tubulin, beta 6 class v, CYBRD1 - cytochrome b reductase 1, SFRP2 - secreted frizzled-related protein 2, SBSN - suprabasin, UCHL1 - ubiquitin carboxyl-terminal esterase l1 (ubiquitin thiolesterase), QPCT - glutaminyl-peptide cyclotransferase, COL8A2 - collagen, type viii, alpha 2, FAM129A - family with sequence similarity 129, member a, SLIT3 - slit |

| GO Term | Description | P-value | FDR q-value | Enrichment | Genes |
|---|---|---|---|---|---|
| | | | | | homolog 3 (*drosophila*), ASS1 - argininosuccinate synthase 1, IGFBP3 - insulin-like growth factor binding protein 3, ADIRF - adipogenesis regulatory factor, BMPER - bmp binding endothelial regulator, MFAP4 - microfibrillar-associated protein 4, THBS4 - thrombospondin 4, PPAP2B - phosphatidic acid phosphatase type 2b, HSPA2 - heat shock 70 kda protein 2, CSRP1 - cysteine and glycine-rich protein 1, HMOX1 - heme oxygenase (decycling) 1, COL11A1 - collagen, type xi, alpha 1, ANPEP - alanyl (membrane) aminopeptidase, GAS6 - growth arrest-specific 6, GSTT2B - glutathione s-transferase theta 2b (gene/pseudogene), FBLN2 - fibulin 2, COL15A1 - collagen, type xv, alpha 1] |
| GO:0070062 | extracellular vesicular exosome | 2.07E−08 | 6.07E−06 | 2.04 | [SCPEP1 - serine carboxypeptidase 1, GSTM2 - glutathione s-transferase mu 2 (muscle), AKR1C3 - aldo-keto reductase family 1, member c3, PGK1 - phosphoglycerate kinase 1, LOXL4 - lysyl oxidase-like 4, PGM1 - phosphoglucomutase 1, GSTM3 - glutathione s-transferase mu 3 (brain), COL18A1 - collagen, type xviii, alpha 1, PGA5 - pepsinogen 5, group i (pepsinogen a), PGAM1 - phosphoglycerate mutase 1 (brain), ANTXR1 - anthrax toxin receptor 1, CDH2 - cadherin 2, type 1, n-cadherin (neuronal), TKT - transketolase, CLDN11 - claudin 11, GSTT2 - glutathione s-transferase theta 2, COTL1 - coactosin-like 1 (*dictyostelium*), ENO2 - enolase 2 (gamma, neuronal), FBLN1 - fibulin 1, AKR1C4 - aldo-keto reductase family 1, member c4, PLOD2 - procollagen-lysine, 2-oxoglutarate 5-dioxygenase 2, CFB - complement factor b, CTSZ - cathepsin z, CLEC3B - c-type lectin domain family 3, member b, ALDH3A2 - aldehyde dehydrogenase 3 family, member a2, APOD - apolipoprotein d, PFKP - phosphofructokinase, platelet, MYO1D - myosin id, F3 - coagulation factor iii (thromboplastin, tissue factor), MARCKSL1 - marcks-like 1, ALCAM - activated leukocyte cell adhesion molecule, AQP1 - aquaporin 1 (colton blood group), KRT34 - keratin 34, TPI1 - triosephosphate isomerase 1, BAIAP2L1 - bai1-associated protein 2-like 1, EEF1A1 - eukaryotic translation elongation factor 1 alpha 1, ISLR - immunoglobulin superfamily containing leucine-rich repeat, PROS1 - protein s (alpha), SERINC2 - serine incorporator 2, LUM - lumican, ACYP1 - acylphosphatase 1, erythrocyte (common) type, CD9 - cd9 molecule, TUBB6 - tubulin, beta 6 class v, CYBRD1 - cytochrome b reductase 1, SBSN - suprabasin, QPCT - glutaminyl-peptide cyclotransferase, FAM129A - family with sequence similarity 129, member a, UCHL1 - ubiquitin carboxyl-terminal esterase l1 (ubiquitin thiolesterase), ASS1 - argininosuccinate synthase 1, IGFBP3 - insulin-like growth factor binding protein 3, MFAP4 - microfibrillar-associated protein 4, ADIRF - adipogenesis regulatory factor, THBS4 - thrombospondin 4, PPAP2B - phosphatidic acid phosphatase type 2b, HSPA2 - heat shock 70 kda protein 2, |

| GO Term | Description | P-value | FDR q-value | Enrichment | Genes |
|---|---|---|---|---|---|
| GO:0065010 | extracellular membrane-bounded organelle | 2.07E−08 | 7.59E−06 | 2.04 | CSRP1 - cysteine and glycine-rich protein 1, ANPEP - alanyl (membrane) aminopeptidase, GAS6 - growth arrest-specific 6, GSTT2B - glutathione s-transferase theta 2b (gene/pseudogene), FBLN2 - fibulin2, COL15A1 - collagen, type xv, alpha 1] [SCPEP1 - serine carboxypeptidase 1, GSTM2 - glutathione s-transferase mu 2 (muscle), AKR1C3 - aldo-keto reductase family 1, member c3, PGK1 - phosphoglycerate kinase 1, LOXL4 - lysyl oxidase-like 4, PGM1 - phosphoglucomutase 1, GSTM3 - glutathione s-transferase mu 3 (brain), COL18A1 - collagen, type xviii, alpha 1, PGA5 - pepsinogen 5, group i (pepsinogen a), PGAM1 - phosphoglycerate mutase 1 (brain), ANTXR1 - anthrax toxin receptor 1, CDH2 - cadherin 2, type 1, n-cadherin (neuronal), TKT - transketolase, CLDN11 - claudin 11, GSTT2 - glutathione s-transferase theta 2, COTL1 - coactosin-like 1 (*dictyostelium*), ENO2 - enolase 2 (gamma, neuronal), FBLN1 - fibulin 1, AKR1C4 - aldo-keto reductase family 1, member c4, PLOD2 - procollagen-lysine, 2-oxoglutarate 5-dioxygenase 2, CFB - complement factor b, CTSZ - cathepsin z, CLEC3B - c-type lectin domain family 3, member b, ALDH3A2 - aldehyde dehydrogenase 3 family, member a2, APOD - apolipoprotein d, PFKP - phosphofructokinase, platelet, MYO1D - myosin id, F3 - coagulation factor iii (thromboplastin, tissue factor), MARCKSL1 - marcks-like 1, ALCAM - activated leukocyte cell adhesion molecule, AQP1 - aquaporin 1 (colton blood group), KRT34 - keratin 34, TPI1 - triosephosphate isomerase 1, BAIAP2L1 - bai1-associated protein 2-like 1, EEF1A1 - eukaryotic translation elongation factor 1 alpha 1, ISLR - immunoglobulin superfamily containing leucine-rich repeat, PROS1 - protein s (alpha), SERINC2 - serine incorporator 2, LUM - lumican, ACYP1 - acylphosphatase 1, erythrocyte (common) type, CD9 - cd9 molecule, TUBB6 - tubulin, beta 6 class v, CYBRD1 - cytochrome b reductase 1, SBSN - suprabasin, QPCT - glutaminyl-peptide cyclotransferase, FAM129A - family with sequence similarity 129, member a, UCHL1 - ubiquitin carboxyl-terminal esterase l1 (ubiquitin thiolesterase), ASS1 - argininosuccinate synthase 1, IGFBP3 - insulin-like growth factor binding protein 3, MFAP4 - microfibrillar-associated protein 4, ADIRF - adipogenesis regulatory factor, THBS4 - thrombospondin 4, PPAP2B - phosphatidic acid phosphatase type 2b, HSPA2 - heat shock 70 kda protein 2, CSRP1 - cysteine and glycine-rich protein 1, ANPEP - alanyl (membrane) aminopeptidase, GAS6 - growth arrest-specific 6, GSTT2B - glutathione s-transferase theta 2b (gene/pseudogene), FBLN2 - fibulin2, COL15A1 - collagen, type xv, alpha 1] |
| GO:0043230 | extracellular organelle | 2.07E−08 | 1.01E−05 | 2.04 | [SCPEP1 - serine carboxypeptidase 1, GSTM2 - glutathione s-transferase mu 2 (muscle), AKR1C3 - aldo-keto reductase family 1, member c3, PGK1 - phosphoglycerate kinase 1, LOXL4 - |

| GO Term | Description | P-value | FDR q-value | Enrichment | Genes |
|---|---|---|---|---|---|
| | | | | | lysyl oxidase-like 4, PGM1 - phosphoglucomutase 1, GSTM3 - glutathione s-transferase mu 3 (brain), COL18A1 - collagen, type xviii, alpha 1, PGA5 - pepsinogen 5, group i (pepsinogen a), PGAM1 - phosphoglycerate mutase 1 (brain), ANTXR1 - anthrax toxin receptor 1, CDH2 - cadherin 2, type 1, n-cadherin (neuronal), TKT - transketolase, CLDN11 - claudin 11, GSTT2 - glutathione s-transferase theta 2, COTL1 - coactosin-like 1 (*dictyostelium*), ENO2 - enolase 2 (gamma, neuronal), FBLN1 - fibulin 1, AKR1C4 - aldo-keto reductase family 1, member c4, PLOD2 - procollagen-lysine, 2-oxoglutarate 5-dioxygenase 2, CFB - complement factor b, CTSZ - cathepsin z, CLEC3B - c-type lectin domain family 3, member b, ALDH3A2 - aldehyde dehydrogenase 3 family, member a2, APOD - apolipoprotein d, PFKP - phosphofructokinase, platelet, MYO1D - myosin id, F3 - coagulation factor iii (thromboplastin, tissue factor), MARCKSL1 - marcks-like 1, ALCAM - activated leukocyte cell adhesion molecule, AQP1 - aquaporin 1 (colton blood group), KRT34 - keratin 34, TPI1 - triosephosphate isomerase 1, BAIAP2L1 - bai1-associated protein 2-like 1, EEF1A1 - eukaryotic translation elongation factor 1 alpha 1, ISLR - immunoglobulin superfamily containing leucine-rich repeat, PROS1 - protein s (alpha), SERINC2 - serine incorporator 2, LUM - lumican, ACYP1 - acylphosphatase 1, erythrocyte (common) type, CD9 - cd9 molecule, TUBB6 - tubulin, beta 6 class v, CYBRD1 - cytochrome b reductase 1, SBSN - suprabasin, QPCT - glutaminyl-peptide cyclotransferase, FAM129A - family with sequence similarity 129, member a, UCHL1 - ubiquitin carboxyl-terminal esterase l1 (ubiquitin thiolesterase), ASS1 - argininosuccinate synthase 1, IGFBP3 - insulin-like growth factor binding protein 3, MFAP4 - microfibrillar-associated protein 4, ADIRF - adipogenesis regulatory factor, THBS4 - thrombospondin 4, PPAP2B - phosphatidic acid phosphatase type 2b, HSPA2 - heat shock 70 kda protein 2, CSRP1 - cysteine and glycine-rich protein 1, ANPEP - alanyl (membrane) aminopeptidase, GAS6 - growth arrest-specific 6, GSTT2B - glutathione s-transferase theta 2b (gene/pseudogene), FBLN2 - fibulin2, COL15A1 - collagen, type xv, alpha 1] |
| GO:0005576 | extracellular region | 1.74E−04 | 2.12E−02 | 2.02 | [COL18A1 - collagen, type xviii, alpha 1, PROS1 - protein s (alpha), SRGN - serglycin, PDGFRL - platelet-derived growth factor receptor-like, CTGF - connective tissue growth factor, OLFML1 - olfactomedin-like 1, CXCL16 - chemokine (c-x-c motif) ligand 16, LUM - lumican, GPX7 - glutathione peroxidase 7, MEGF6 - multiple egf-like-domains 6, COL4A1 - collagen, type iv, alpha 1, PSG6 - pregnancy specific beta-1-glycoprotein 6, FBLN1 - fibulin 1, CTSK - cathepsin k, COL8A2 - collagen, type viii, alpha 2, CFB - complement factor b, PENK - proenkephalin, IL1R1 - interleukin 1 receptor, type i, CCL2 - chemokine (c-c motif) ligand 2, IGFBP3 - |

| GO Term | Description | P-value | FDR q-value | Enrichment | Genes |
|---|---|---|---|---|---|
| | | | | | insulin-like growth factor binding protein 3, CPA4 - carboxypeptidase a4, MFAP4 - microfibrillar-associated protein 4, THBS4 - thrombospondin 4, CLEC3B - c-type lectin domain family 3, member b, APOD - apolipoprotein d, COL11A1 - collagen, type xi, alpha 1, GAS6 - growth arrest-specific 6, FBLN2 - fibulin 2, COL15A1 - collagen, type xv, alpha 1, TNFRSF11B - tumor necrosis factor receptor superfamily, member 11b] |
| GO:0031982 | vesicle | 6.79E−08 | 1.66E−05 | 1.89 | [GSTM2 - glutathione s-transferase mu 2 (muscle), SCPEP1 - serine carboxypeptidase 1, AKR1C3 - aldo-keto reductase family 1, member c3, PGK1 - phosphoglycerate kinase 1, LOXL4 - lysyl oxidase-like 4, GSTM3 - glutathione s-transferase mu 3 (brain), PGM1 - phosphoglucomutase 1, COL18A1 - collagen, type xviii, alpha 1, PGA5 - pepsinogen 5, group i (pepsinogen a), PGAM1 - phosphoglycerate mutase 1 (brain), ANTXR1 - anthrax toxin receptor 1, TKT - transketolase, CDH2 - cadherin 2, type 1, n-cadherin (neuronal), SRGN - serglycin, CLDN11 - claudin 11, GSTT2 - glutathione s-transferase theta 2, COTL1 - coactosin-like 1 (*dictyostelium*), ENO2 - enolase 2 (gamma, neuronal), FBLN1 - fibulin 1, AKR1C4 - aldo-keto reductase family 1, member c4, PLOD2 - procollagen-lysine, 2-oxoglutarate 5-dioxygenase 2, CFB - complement factor b, CTSZ - cathepsin z, TBC1D2 - tbc1 domain family, member 2, CLEC3B - c-type lectin domain family 3, member b, ALDH3A2 - aldehyde dehydrogenase 3 family, member a2, APOD - apolipoprotein d, PFKP - phosphofructokinase, platelet, MYO1D - myosin id, MARCKSL1 - marcks-like 1, F3 - coagulation factor iii (thromboplastin, tissue factor), ALCAM - activated leukocyte cell adhesion molecule, AQP1 - aquaporin 1 (colton blood group), STMN2 - stathmin-like 2, ADAMTS1 - adam metallopeptidase with thrombospondin type 1 motif, 1, KRT34 - keratin 34, TPI1 - triosephosphate isomerase 1, BAIAP2L1 - bai1-associated protein 2-like 1, EEF1A1 - eukaryotic translation elongation factor 1 alpha 1, ISLR - immunoglobulin superfamily containing leucine-rich repeat, PROS1 - protein s (alpha), SERINC2 - serine incorporator 2, LUM - lumican, ACYP1 - acylphosphatase 1, erythrocyte (common) type, CD9 - cd9 molecule, TRPV2 - transient receptor potential cation channel, subfamily v, member 2, TUBB6 - tubulin, beta 6 class v, AXIN2 - axin 2, CYBRD1 - cytochrome b reductase 1, SBSN - suprabasin, UCHL1 - ubiquitin carboxyl-terminal esterase l1 (ubiquitin thiolesterase), QPCT - glutaminyl-peptide cyclotransferase, FAM129A - family with sequence similarity 129, member a, ASS1 - argininosuccinate synthase 1, IGFBP3 - insulin-like growth factor binding protein 3, ADIRF - adipogenesis regulatory factor, MFAP4 - microfibrillar-associated protein 4, THBS4 - thrombospondin 4, PPAP2B - phosphatidic acid phosphatase type 2b, HSPA2 - heat shock 70 kda protein 2, CSRP1 - cysteine and glycine- |

| GO Term | Description | P-value | FDR q-value | Enrichment | Genes |
|---|---|---|---|---|---|
| | | | | | rich protein 1, GAS6 - growth arrest-specific 6, ANPEP - alanyl (membrane) aminopeptidase, GSTT2B - glutathione s-transferase theta 2b (gene/pseudogene), FBLN2 - fibulin2, COL15A1 - collagen, type xv, alpha 1] |
| GO:0031988 | membrane-bounded vesicle | 1.18E−07 | 2.47E−05 | 1.89 | [SCPEP1 - serine carboxypeptidase 1, GSTM2 - glutathione s-transferase mu 2 (muscle), AKR1C3 - aldo-keto reductase family 1, member c3, PGK1 - phosphoglycerate kinase 1, LOXL4 - lysyl oxidase-like 4, PGM1 - phosphoglucomutase 1, GSTM3 - glutathione s-transferase mu 3 (brain), COL18A1 - collagen, type xviii, alpha 1, PGA5 - pepsinogen 5, group i (pepsinogen a), PGAM1 - phosphoglycerate mutase 1 (brain), ANTXR1 - anthrax toxin receptor 1, CDH2 - cadherin 2, type 1, n-cadherin (neuronal), SRGN - serglycin, TKT - transketolase, CLDN11 - claudin 11, GSTT2 - glutathione s-transferase theta 2, COTL1 - coactosin-like 1 (*dictyostelium*), ENO2 - enolase 2 (gamma, neuronal), FBLN1 - fibulin 1, AKR1C4 - aldo-keto reductase family 1, member c4, PLOD2 - procollagen-lysine, 2-oxoglutarate 5-dioxygenase 2, CFB - complement factor b, CTSZ - cathepsin z, TBC1D2 - tbc1 domain family, member 2, CLEC3B - c-type lectin domain family 3, member b, ALDH3A2 - aldehyde dehydrogenase 3 family, member a2, APOD - apolipoprotein d, PFKP - phosphofructokinase, platelet, MYO1D - myosin id, F3 - coagulation factor iii (thromboplastin, tissue factor), MARCKSL1 - marcks-like 1, ALCAM - activated leukocyte cell adhesion molecule, AQP1 - aquaporin 1 (colton blood group), KRT34 - keratin 34, TPI1 - triosephosphate isomerase 1, BAIAP2L1 - bai1-associated protein 2-like 1, ISLR - immunoglobulin superfamily containing leucine-rich repeat, EEF1A1 - eukaryotic translation elongation factor 1 alpha 1, PROS1 - protein s (alpha), SERINC2 - serine incorporator 2, LUM - lumican, ACYP1 - acylphosphatase 1, erythrocyte (common) type, TRPV2 - transient receptor potential cation channel, subfamily v, member 2, CD9 - cd9 molecule, TUBB6 - tubulin, beta 6 class v, AXIN2 - axin 2, CYBRD1 - cytochrome b reductase 1, SBSN - suprabasin, FAM129A - family with sequence similarity 129, member a, QPCT - glutaminyl-peptide cyclotransferase, UCHL1 - ubiquitin carboxyl-terminal esterase l1 (ubiquitin thiolesterase), ASS1 - argininosuccinate synthase 1, IGFBP3 - insulin-like growth factor binding protein 3, MFAP4 - microfibrillar-associated protein 4, ADIRF - adipogenesis regulatory factor, THBS4 - thrombospondin 4, PPAP2B - phosphatidic acid phosphatase type 2b, HSPA2 - heat shock 70 kda protein 2, CSRP1 - cysteine and glycine-rich protein 1, ANPEP - alanyl (membrane) aminopeptidase, GAS6 - growth arrest-specific 6, GSTT2B - glutathione s-transferase theta 2b (gene/pseudogene), FBLN2 - fibulin 2, COL15A1 - collagen, type xv, alpha 1] |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

We claim:

1. A device comprising a hydrogel and a population of fibroblasts, wherein the hydrogel comprises pores, and wherein the population of fibroblasts is seeded into or onto the hydrogel, and wherein the population of fibroblasts comprises diabetic ulcer fibroblasts, which express fibronectin at a level at least two-fold more than nondiabetic, nonulcerated foot-derived fibroblasts.

2. The device of claim 1, wherein the pores comprise micropores, macropores, or a combination thereof.

3. The device of claim 1, wherein the population of fibroblasts comprises a fibroblast that is derived from a portion of the skin of the subject.

4. The device of claim 1, wherein the subject is a mammal.

5. The device of claim 4, wherein the subject is a human.

6. The device of claim 1, wherein the population of fibroblasts comprises fibroblasts that have been cultured in vitro.

7. The device of claim 1, wherein the population of fibroblasts comprises a genetically modified fibroblast.

8. The device of claim 1, wherein the device further comprises a bioactive composition.

9. The device of claim 8, wherein the bioactive composition comprises vascular endothelial growth factor (VEGF), hepatocyte growth factor (HGF), fibroblast growth factor 2 (FGF2), or a combination thereof.

10. The device of claim 1, wherein said hydrogel comprises an alginate hydrogel.

11. A method of treating a wound in a diabetic patient in need thereof, the method comprising administering the device of claim 1 to the diabetic patient, thereby treating the wound in the diabetic patient.

12. The method of claim 11, wherein the patient suffers from an ulcer.

13. The method of claim 12, wherein the ulcer is located in an extremity of the patient.

14. The method of claim 11, wherein the device is administered by injection, implantation, or placement on a wound bed.

15. The method of claim 11, wherein the population of fibroblasts comprises an autologous fibroblast.

16. The method of claim 11, wherein the population of fibroblasts comprises an allogeneic or xenogeneic fibroblast.

17. The method of claim 16, wherein the population of fibroblasts comprises at least 10% autologous fibroblasts.

18. The method of claim 16, wherein the population of fibroblasts comprises at least 10% allogeneic fibroblasts.

19. The method of claim 16, wherein the population of fibroblasts comprises at least 10% xenogeneic fibroblasts.

\* \* \* \* \*

UNITED STATES PATENT AND TRADEMARK OFFICE
CERTIFICATE OF CORRECTION

PATENT NO. : 10,130,661 B2
APPLICATION NO. : 14/709258
DATED : November 20, 2018
INVENTOR(S) : Veves et al.

It is certified that error appears in the above-identified patent and that said Letters Patent is hereby corrected as shown below:

In the Specification

Column 1, Line numbers 12-15, please replace:
"The invention was supported, in whole, or in part, by NIH grant numbers 1 R24 DK091210-01A1, RO1 DE017413-01A1, and RO1 DK98055-06A1. The Government has certain rights in the invention."

With:
-- This invention was made with government support under DK091210 and DE017413 and DK098055 awarded by National Institutes of Health (NIH). The government has certain rights in this invention. --

Signed and Sealed this
Twentieth Day of September, 2022

Katherine Kelly Vidal
*Director of the United States Patent and Trademark Office*

SEQUENCE LISTING

```
<160> NUMBER OF SEQ ID NOS: 32

<210> SEQ ID NO 1
<211> LENGTH: 9
<212> TYPE: PRT
<213> ORGANISM: Unknown
<220> FEATURE:
<223> OTHER INFORMATION: Description of Unknown:
      Proteoglycan attachment peptide

<400> SEQUENCE: 1

Gly Gly Gly Gly Arg Gly Asp Ser Pro
1               5

<210> SEQ ID NO 2
<211> LENGTH: 6
<212> TYPE: PRT
<213> ORGANISM: Unknown
<220> FEATURE:
<223> OTHER INFORMATION: Description of Unknown:
      Proteoglycan attachment peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 2

Xaa Asx Asx Xaa Asx Xaa
1               5

<210> SEQ ID NO 3
<211> LENGTH: 6
<212> TYPE: PRT
<213> ORGANISM: Unknown
<220> FEATURE:
<223> OTHER INFORMATION: Description of Unknown:
      Proteoglycan attachment peptide

<400> SEQUENCE: 3

Pro Arg Arg Ala Arg Val
1               5

<210> SEQ ID NO 4
<211> LENGTH: 19
<212> TYPE: PRT
<213> ORGANISM: Unknown
<220> FEATURE:
<223> OTHER INFORMATION: Description of Unknown:
      Proteoglycan attachment peptide

<400> SEQUENCE: 4
```

```
Tyr Glu Lys Pro Gly Ser Pro Pro Arg Glu Val Val Pro Arg Pro Arg
1               5                   10                  15

Pro Gly Val

<210> SEQ ID NO 5
<211> LENGTH: 28
<212> TYPE: PRT
<213> ORGANISM: Unknown
<220> FEATURE:
<223> OTHER INFORMATION: Description of Unknown:
      Proteoglycan attachment peptide

<400> SEQUENCE: 5

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 6
<211> LENGTH: 17
<212> TYPE: PRT
<213> ORGANISM: Unknown
<220> FEATURE:
<223> OTHER INFORMATION: Description of Unknown:
      Proteoglycan attachment peptide

<400> SEQUENCE: 6

Arg Ile Gln Asn Leu Leu Lys Ile Thr Asn Leu Arg Ile Lys Phe Val
1               5                   10                  15

Lys

<210> SEQ ID NO 7
<211> LENGTH: 4
<212> TYPE: PRT
<213> ORGANISM: Unknown
<220> FEATURE:
<223> OTHER INFORMATION: Description of Unknown:
      Fibronectin peptide

<400> SEQUENCE: 7

Arg Gly Asp Ser
1

<210> SEQ ID NO 8
<211> LENGTH: 4
<212> TYPE: PRT
<213> ORGANISM: Unknown
<220> FEATURE:
<223> OTHER INFORMATION: Description of Unknown:
      Fibronectin peptide

<400> SEQUENCE: 8

Arg Glu Asp Val
1

<210> SEQ ID NO 9
<211> LENGTH: 4
<212> TYPE: PRT
<213> ORGANISM: Unknown
<220> FEATURE:
<223> OTHER INFORMATION: Description of Unknown:
      Vitronectin peptide

<400> SEQUENCE: 9

Arg Gly Asp Val
```

-continued

```
<210> SEQ ID NO 10
<211> LENGTH: 5
<212> TYPE: PRT
<213> ORGANISM: Unknown
<220> FEATURE:
<223> OTHER INFORMATION: Description of Unknown:
      Laminin A peptide

<400> SEQUENCE: 10

Leu Arg Gly Asp Asn
1               5

<210> SEQ ID NO 11
<211> LENGTH: 5
<212> TYPE: PRT
<213> ORGANISM: Unknown
<220> FEATURE:
<223> OTHER INFORMATION: Description of Unknown:
      Laminin A peptide

<400> SEQUENCE: 11

Ile Lys Val Ala Val
1               5

<210> SEQ ID NO 12
<211> LENGTH: 5
<212> TYPE: PRT
<213> ORGANISM: Unknown
<220> FEATURE:
<223> OTHER INFORMATION: Description of Unknown:
      Laminin B1 peptide

<400> SEQUENCE: 12

Tyr Ile Gly Ser Arg
1               5

<210> SEQ ID NO 13
<211> LENGTH: 5
<212> TYPE: PRT
<213> ORGANISM: Unknown
<220> FEATURE:
<223> OTHER INFORMATION: Description of Unknown:
      Laminin B1 peptide

<400> SEQUENCE: 13

Pro Asp Ser Gly Arg
1               5

<210> SEQ ID NO 14
<211> LENGTH: 10
<212> TYPE: PRT
<213> ORGANISM: Unknown
<220> FEATURE:
<223> OTHER INFORMATION: Description of Unknown:
      Laminin B2 peptide

<400> SEQUENCE: 14

Arg Asn Ile Ala Glu Ile Ile Lys Asp Ala
1               5                   10

<210> SEQ ID NO 15
<211> LENGTH: 4
<212> TYPE: PRT
<213> ORGANISM: Unknown
<220> FEATURE:
<223> OTHER INFORMATION: Description of Unknown:
```

```
                                Collagen 1 peptide

<400> SEQUENCE: 15

Arg Gly Asp Thr
  1

<210> SEQ ID NO 16
<211> LENGTH: 4
<212> TYPE: PRT
<213> ORGANISM: Unknown
<220> FEATURE:
<223> OTHER INFORMATION: Description of Unknown:
      Collagen 1 peptide

<400> SEQUENCE: 16

Asp Gly Glu Ala
  1

<210> SEQ ID NO 17
<211> LENGTH: 4
<212> TYPE: PRT
<213> ORGANISM: Unknown
<220> FEATURE:
<223> OTHER INFORMATION: Description of Unknown:
      Thrombospondin peptide
<220> FEATURE:
<221> NAME/KEY: MOD_RES
<222> LOCATION: (3)..(3)
<223> OTHER INFORMATION: Any amino acid

<400> SEQUENCE: 17

Val Thr Xaa Gly
  1

<210> SEQ ID NO 18
<211> LENGTH: 8815
<212> TYPE: DNA
<213> ORGANISM: Homo sapiens

<400> SEQUENCE: 18
gcccgcgccg gctgtgctgc acaggggag gagagggaac cccaggcgcg agcgggaaga       60
ggggacctgc agccacaact tctctggtcc tctgcatccc ttctgtccct ccacccgtcc     120
ccttccccac cctctggccc ccaccttctt ggaggcgaca accccgggga ggcattagaa     180 gggattttc ccgcaggttg cgaagggaag caaacttggt ggcaacttgc ctcccggtgc      240
gggcgtctct cccccaccgt ctcaacatgc ttaggggtcc ggggcccggg ctgctgctgc     300
tggccgtcca gtgcctgggg acagcggtgc cctccacggg agcctcgaag agcaagaggc     360
aggctcagca aatggttcag ccccagtccc cggtggctgt cagtcaaagc aagcccggtt     420
gttatgacaa tggaaaacac tatcagataa atcaacagtg ggagcggacc tacctaggca     480
atgcgttggt ttgtacttgt tatggaggaa gccgaggttt taactgcgag agtaaacctg     540
aagctgaaga gacttgcttt gacaagtaca ctgggaacac ttaccgagtg ggtgacactt     600
atgagcgtcc taaagactcc atgatctggg actgtacctg catcggggct gggcgaggga     660
gaataagctg taccatcgca aaccgctgcc atgaagggg tcagtcctac aagattggtg      720
acacctggag gagaccacat gagactggtg gttacatgtt agagtgtgtg tgtcttggta     780
atggaaaagg agaatggacc tgcaagccca gctgagaa gtgttttgat catgctgctg      840
ggacttccta tgtggtcgga gaaacgtggg agaagcccta ccaaggctgg atgatggtag     900
attgtacttg cctgggagaa ggcagcggac gcatcacttg cacttctaga aatagatgca     960
```

-continued

```
acgatcagga cacaaggaca tcctatagaa ttggagacac ctggagcaag aaggataatc    1020
gaggaaacct gctccagtgc atctgcacag gcaacggccg aggagagtgg aagtgtgaga    1080
ggcacacctc tgtgcagacc acatcgagcg gatctggccc cttcaccgat gttcgtgcag    1140
ctgtttacca accgcagcct cacccccagc ctcctcccta tggccactgt gtcacagaca    1200
gtggtgtggt ctactctgtg gggatgcagt ggctgaagac acaaggaaat aagcaaatgc    1260
tttgcacgtg cctgggcaac ggagtcagct gccaagagac agctgtaacc cagacttacg    1320
gtggcaactc aaatggagag ccatgtgtct taccattcac ctacaatggc aggacgttct    1380
actcctgcac cacagaaggg cgacaggacg gacatctttg gtgcagcaca acttcgaatt    1440
atgagcagga ccagaaatac tctttctgca cagaccacac tgttttggtt cagactcgag    1500
gaggaaattc caatggtgcc ttgtgccact tccccttcct atacaacaac cacaattaca    1560
ctgattgcac ttctgagggc agaagagaca acatgaagtg gtgtgggacc acacagaact    1620
atgatgccga ccagaagttt gggttctgcc ccatggctgc ccacgaggaa atctgcacaa    1680
ccaatgaagg ggtcatgtac cgcattggag atcagtggga taagcagcat gacatgggtc    1740
acatgatgag gtgcacgtgt gttgggaatg gtcgtgggga atggacatgc attgcctact    1800
cgcagcttcg agatcagtgc attgttgatg acatcactta caatgtgaac gacacattcc    1860
acaagcgtca tgaagagggg cacatgctga actgtacatg cttcggtcag ggtcggggca    1920
ggtggaagtg tgatcccgtc gaccaatgcc aggattcaga gactgggacg ttttatcaaa    1980
ttggagattc atgggagaag tatgtgcatg gtgtcagata ccagtgctac tgctatggcc    2040
gtggcattgg ggagtggcat tgccaacctt tacagaccta tccaagctca gtggtcctg    2100 tcgaagtatt tatcactgag actccgagtc agcccaactc ccaccccatc cagtggaatg    2160
caccacagcc atctcacatt tccaagtaca ttctcaggtg gagacctaaa aattctgtag    2220
gccgttggaa ggaagctacc ataccaggcc acttaaactc ctacaccatc aaaggcctga    2280
agcctggtgt ggtatacgag ggccagctca tcagcatcca gcagtacggc caccaagaag    2340
tgactcgctt tgacttcacc accaccagca ccagcacacc tgtgaccagc aacaccgtga    2400
caggagagac gactcccttt tctcctcttg tggccacttc tgaatctgtg accgaaatca    2460
cagccagtag cttttgtggtc tcctgggtct cagcttccga caccgtgtcg ggattccggg    2520
tggaatatga gctgagtgag gagggagatg agccacagta cctggatctt ccaagcacag    2580
ccacttctgt gaacatccct gacctgcttc ctggccgaaa atacattgta aatgtctatc    2640
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tcccgtcaa cctgcctggc gagcacgggc    3120
agaggctgcc catcagcagg aacacctttg cagaagtcac cgggctgtcc cctggggtca    3180
cctattactt caagtctttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
```

```
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccagggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agaggtgccc caactcactg   4080
acctaagctt tgttgatata accgattcaa gcatcggcct gaggtggacc ccgctaaact   4140
cttccaccat tattgggtac cgcatcacag tagttgcggc aggagaaggt atccctattt   4200
ttgaagattt tgtggactcc tcagtaggat actacacagt cacagggctg gagccgggca   4260
ttgactatga tatcagcgtt atcactctca ttaatggcgg cgagagtgcc cctactacac   4320
tgacacaaca aacggctgtt cctcctccca ctgacctgcg attcaccaac attggtccag   4380
acaccatgcg tgtcacctgg gctccacccc catccattga tttaaccaac ttcctggtgc   4440
gttactcacc tgtgaaaaat gaggaagatg ttgcagagtt gtcaatttct ccttcagaca   4500
atgcagtggt cttaacaaat ctcctgcctg gtacagaata tgtagtgagt gtctccagtg   4560
tctacgaaca acatgagagc acctcttta gaggaagaca gaaaacaggt cttgattccc   4620
caactggcat tgactttct gatattactg ccaactcttt tactgtgcac tggattgctc   4680
ctcgagccac catcactggc tacaggatcc gccatcatcc cgagcacttc agtgggagac   4740
ctcgagaaga tcgggtgccc cactctcgga attccatcac cctcaccaac ctcactccag   4800
gcacagagta tgtggtcagc atcgttgctc ttaatggcag agaggaaagt cccttattga   4860
ttggccaaca atcaacagtt tctgatgttc cgagggacct ggaagttgtt gctgcgaccc   4920
ccaccagcct actgatcagc tgggatgctc ctgctgtcac agtgagatat acaggatca   4980 cttacggaga gacaggagga aatagccctg tccaggagtt cactgtgcct gggagcaagt   5040
ctacagctac catcagcggc cttaaacctg gagttgatta taccatcact gtgtatgctg   5100
tcactggccg tggagacagc cccgcaagca gcaagccaat ttccattaat taccgaacag   5160
aaattgacaa accatcccag atgcaagtga ccgatgttca ggacaacagc attagtgtca   5220
agtggctgcc ttcaagttcc cctgttactg gttacagagt aaccaccact cccaaaaatg   5280
gaccaggacc aacaaaaact aaaactgcag gtccagatca aacagaaatg actattgaag   5340
gcttgcagcc cacagtggag tatgtggtta gtgtctatgc tcagaatcca gcggagaga   5400 gtcagcctct ggttcagact gcagtaacca acattgatcg ccctaaagga ctggcattca   5460
ctgatgtgga tgtcgattcc atcaaaattg cttgggaaag cccacagggg caagtttcca   5520
ggtacagggt gacctactcg agccctgagg atggaatcca tgagctattc cctgcacctg   5580
atggtgaaga agacactgca gagctgcaag gcctcagacc gggttctgag tacacagtca   5640
gtgtggttgc cttgcacgat gatatggaga gccagcccct gattggaacc cagtccacag   5700
```

-continued

```
ctattcctgc caccaactgac ctgaagttca ctcaggtcac acccacaagc ctgagcgccc   5760
agtggacacc acccaatgtt cagctcactg gatatcgagt gcgggtgacc cccaaggaga   5820
agaccggacc aatgaaagaa atcaaccttg ctcctgacag ctcatccgtg gttgtatcag   5880
gacttatggt ggccaccaaa tatgaagtga gtgtctatgc tcttaaggac actttgacaa   5940
gcagaccagc tcagggagtt gtcaccactc tggagaatgt cagcccacca agaagggctc   6000
gtgtgacaga tgctactgag accaccatca ccattagctg gagaaccaag actgagacga   6060
tcactggctt ccaagttgat gccgttccag ccaatggcca gactccaatc cagagaacca   6120
tcaagccaga tgtcagaagc tacaccatca caggtttaca accaggcact gactacaaga   6180
tctacctgta caccttgaat gacaatgctc ggagctcccc tgtggtcatc gacgcctcca   6240
ctgccattga tgcaccatcc aacctgcgtt tcctggccac cacacccaat tccttgctgg   6300
tatcatggca gccgccacgt gccaggatta ccggctacat catcaagtat gagaagcctg   6360
ggtctcctcc cagagaagtg gtccctcggc ccgccctgg tgtcacagag gctactatta   6420
ctggcctgga accgggaacc gaatatacaa tttatgtcat tgccctgaag aataatcaga   6480
agagcgagcc cctgattgga aggaaaaaga cagacgagct tccccaactg gtaacccttc   6540 cacacccccaa tcttcatgga ccagagatct tggatgttcc ttccacagtt caaaagaccc   6600
ctttcgtcac ccacccctggg tatgacactg gaaatggtat tcagcttcct ggcacttctg   6660
gtcagcaacc cagtgttggg caacaaatga tctttgagga acatggttt aggcggacca   6720 caccgcccac aacggccacc cccataaggc ataggccaag accataccccg ccgaatgtag   6780 gtgaggaaat ccaaattggt cacatccccca gggaagatgt agactatcac ctgtaccccac   6840 acggtccggg actcaatcca aatgcctcta caggacaaga agctctctct cagacaacca   6900
tctcatgggc cccattccag gacacttctg agtacatcat ttcatgtcat cctgttggca   6960
ctgatgaaga accccttacag ttcagggttc ctggaacttc taccagtgcc actctgacag   7020
gcctcaccag aggtgccacc tacaacatca tagtggaggc actgaaagac cagcagaggc   7080
ataaggttcg ggaagaggtt gttaccgtgg gcaactctgt caacgaaggc ttgaaccaac   7140
ctacggatga ctcgtgcttt gacccctaca cagtttccca ttatgccgtt ggagatgagt   7200
gggaacgaat gtctgaatca ggctttaaac tgttgtgcca gtgcttaggc tttggaagtg   7260
gtcatttcag atgtgattca tctagatggt gccatgacaa tggtgtgaac tacaagattg   7320
gagagaagtg ggaccgtcag ggagaaaatg gccagatgat gagctgcaca tgtcttggga   7380
acggaaaagg agaattcaag tgtgaccctc atgaggcaac gtgttatgat gatgggaaga   7440
cataccacgt aggagaacag tggcagaagg aatatctcgg tgccatttgc tcctgcacat   7500
gctttggagg ccagcggggc tggcgctgtg acaactgccg cagacctggg ggtgaaccca   7560
gtcccgaagg cactactggc cagtcctaca accagtattc tcagagatac catcagagaa   7620
caaacactaa tgttaattgc ccaattgagt gcttcatgcc tttagatgta caggctgaca   7680
gagaagattc ccgagagtaa atcatctttc caatccagag gaacaagcat gtctctctgc   7740
caagatccat ctaaactgga gtgatgttag cagacccagc ttagagttct tctttctttc   7800
ttaagccctt tgctctggag gaagttctcc agcttcagct caactcacag cttctccaag   7860
catcaccctg ggagtttcct gagggttttc tcataaatga gggctgcaca ttgcctgttc   7920
tgcttcgaag tattcaatac cgctcagtat tttaaatgaa gtgattctaa gatttggttt   7980
gggatcaata ggaaagcata tgcagccaac caagatgcaa atgttttgaa atgatatgac   8040
caaaatttta agtaggaaag tcacccaaac acttctgctt tcacttaagt gtctggcccg   8100
```

-continued

```
caatactgta ggaacaagca tgatcttgtt actgtgatat tttaaatatc cacagtactc    8160
acttttccca aatgatccta gtaattgcct agaaatatct ttctcttacc tgttatttat    8220 caattttttcc cagtattttt atacggaaaa aattgtattg aaaacactta gtatgcagtt    8280
gataagagga atttggtata attatggtgg gtgattattt tttatactgt atgtgccaaa    8340
gctttactac tgtggaaaga caactgtttt aataaaagat ttacattcca caacttgaag    8400
ttcatctatt tgatataaga caccttcggg ggaaataatt cctgtgaata ttcttttttca   8460 attcagcaaa catttgaaaa tctatgatgt gcaagtctaa ttgttgattt cagtacaaga    8520
ttttctaaat cagttgctac aaaaactgat tggttttgt cacttcatct cttcactaat     8580
ggagatagct ttacactttc tgctttaata gatttaagtg gaccccaata tttattaaaa    8640
ttgctagttt accgttcaga agtataatag aaataatctt tagttgctct tttctaacca    8700
ttgtaattct tcccttcttc cctccacctt tccttcattg aataaacctc tgttcaaaga    8760
gattgcctgc aagggaaata aaatgactaa agatattaaa aaaaaaaaaa aaaaa         8815
```

<210> SEQ ID NO 19
<211> LENGTH: 376
<212> TYPE: PRT
<213> ORGANISM: Homo sapiens

<400> SEQUENCE: 19

```
Met Cys Glu Glu Glu Thr Thr Ala Leu Val Cys Asp Asn Gly Ser Gly
1               5                   10                  15

Leu Cys Lys Ala Gly Phe Ala Gly Asp Asp Ala Pro Arg Ala Val Phe
            20                  25                  30

Pro Ser Ile Val Gly Arg Pro Arg His Gln Gly Val Met Val Gly Met
        35                  40                  45

Gly Gln Lys Asp Ser Tyr Val Gly Asp Glu Ala Gln Ser Lys Arg Gly
    50                  55                  60

Ile Leu Thr Leu Lys Tyr Pro Ile Glu His Gly Ile Ile Thr Asn Trp
65                  70                  75                  80

Asp Asp Met Glu Lys Ile Trp His His Ser Phe Tyr Asn Glu Leu Arg
                85                  90                  95

Val Ala Pro Glu Glu His Pro Thr Leu Leu Thr Glu Ala Pro Leu Asn
            100                 105                 110

Pro Lys Ala Asn Arg Glu Lys Met Thr Gln Ile Met Phe Glu Thr Phe
        115                 120                 125

Asn Val Pro Ala Met Tyr Val Ala Ile Gln Ala Val Leu Ser Leu Tyr
    130                 135                 140

Ala Ser Gly Arg Thr Thr Gly Ile Val Leu Asp Ser Gly Asp Gly Val
145                 150                 155                 160

Thr His Asn Val Pro Ile Tyr Glu Gly Tyr Ala Leu Pro His Ala Ile
                165                 170                 175

Met Arg Leu Asp Leu Ala Gly Arg Asp Leu Thr Asp Tyr Leu Met Lys
            180                 185                 190

Ile Leu Thr Glu Arg Gly Tyr Ser Phe Val Thr Thr Ala Glu Arg Glu
        195                 200                 205

Ile Val Arg Asp Ile Lys Glu Lys Leu Cys Tyr Val Ala Leu Asp Phe
    210                 215                 220

Glu Asn Glu Met Ala Thr Ala Ala Ser Ser Ser Leu Glu Lys Ser
225                 230                 235                 240

Tyr Glu Leu Pro Asp Gly Gln Val Ile Thr Ile Gly Asn Glu Arg Phe
```

```
                245                 250                 255
Arg Cys Pro Glu Thr Leu Phe Gln Pro Ser Phe Ile Gly Met Glu Ser
            260                 265                 270

Ala Gly Ile His Glu Thr Thr Tyr Asn Ser Ile Met Lys Cys Asp Ile
        275                 280                 285

Asp Ile Arg Lys Asp Leu Tyr Ala Asn Asn Val Leu Ser Gly Gly Thr
    290                 295                 300

Thr Met Tyr Pro Gly Ile Ala Asp Arg Met Gln Lys Glu Ile Thr Ala
305                 310                 315                 320

Leu Ala Pro Ser Thr Met Lys Ile Lys Ile Ile Ala Pro Pro Glu Arg
                325                 330                 335

Lys Tyr Ser Val Trp Ile Gly Gly Ser Ile Leu Ala Ser Leu Ser Thr
            340                 345                 350

Phe Gln Gln Met Trp Ile Ser Lys Pro Glu Tyr Asp Glu Ala Gly Pro
        355                 360                 365

Ser Ile Val His Arg Lys Cys Phe
    370                 375

<210> SEQ ID NO 20
<211> LENGTH: 1304
<212> TYPE: DNA
<213> ORGANISM: Homo sapiens

<400> SEQUENCE: 20
aggtttctta aaaaaaacac acagagaaat attgtgctcc agccccagc tcattccacc      60
gctcccacca tgtgtgaaga agagaccacc gcccttgtgt gtgacaatgg ctctggcctg    120
tgcaaggcag gctttgcagg agatgatgcc cccagggctg tcttcccctc cattgtgggc    180
cgccctagac atcagggtgt gatggtggga atgggccaga agacagcta tgtggggac     240
gaggctcaga gcaagcgtgg gatcctaact ctcaagtacc ctattgaaca tggcatcatc    300
accaactggg atgacatgga gaagatctgg caccactcct tctacaatga gcttcgagta    360
gcaccagaag agcaccccac cctgctcaca gaggccccc  taaaccccaa agcaaacaga    420
gagaagatga cccagatcat gttcgaaacc ttcaatgtcc ctgccatgta tgttgctatt    480
caggctgtgc tctcactcta tgcatccggc cgtaccacag gcatcgttct ggattcgggg    540
gatggcgtca cccacaatgt ccccatctat gagggctatg cactgcccca tgccatcatg    600
cgtcttgacc tggctggacg ggatctcaca gactacctca tgaagattct cacagaaaga    660
ggctattcct ttgtgaccac agctgagaga gaaattgtac gagacatcaa ggagaagctg    720
tgctatgtag ccctggattt cgagaatgag atggccacag cagcttcatc ttcttccctg    780
gagaaaagct acgagttgcc tgatgggcag gtcatcacta ttggcaacga gcgcttccgc    840
tgcccggaga ccctcttcca gccttccttc attggcatgg agtcagctgg aattcatgaa    900
acaacataca attccatcat gaagtgtgac attgacatcc gcaaagattt gtatgctaac    960
aatgtcctct ctgggggcac taccatgtac cctggcattg ctgacaggat gcagaaggaa   1020
atcacagcct ggctcccag  caccatgaag atcaagatta tcgctcctcc tgagcggaag   1080
tactcagtct ggattggcgg ctccatcctg gcctctctct ccaccttcca gcaaatgtgg   1140
atcagcaagc cagagtatga tgaggcaggg ccctccattg tccacaggaa atgcttctaa   1200
agtcagaggg ccttctctgg ggatccccac aagactgctg tcaccagcca cagatcatta   1260
aaaccttcaa gccgaaaaaa aaaaaaaaaa aaaaaaaaa aaaa                       1304
```

```
<210> SEQ ID NO 21
<211> LENGTH: 402
<212> TYPE: PRT
<213> ORGANISM: Homo sapiens

<400> SEQUENCE: 21

Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
            20                  25                  30

His Leu Ala Ser Asp Phe Gly Val Arg Val Phe Gln Gln Val Ala Gln
                35                  40                  45

Ala Ser Lys Asp Arg Asn Val Val Phe Ser Pro Tyr Gly Val Ala Ser
        50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
        355                 360                 365

Arg Met Ala Pro Glu Glu Ile Ile Met Asp Arg Pro Phe Leu Phe Val
370                 375                 380
```

Val Arg His Asn Pro Thr Gly Thr Val Leu Phe Met Gly Gln Val Met
385                 390                 395                 400

Glu Pro

<210> SEQ ID NO 22
<211> LENGTH: 2876
<212> TYPE: DNA
<213> ORGANISM: Homo sapiens

<400> SEQUENCE: 22

```
gaattcctgc agctcagcag ccgccgccag agcaggacga accgccaatc gcaaggcacc      60
tctgagaact tcaggatgca gatgtctcca gccctcacct gcctagtcct gggcctggcc     120
cttgtctttg gtgaagggtc tgctgtgcac catcccccat cctacgtggc ccacctggcc     180
tcagacttcg gggtgagggt gtttcagcag gtggcgcagg cctccaagga ccgcaacgtg     240
gtttctctca cctatggggt ggcctcggtg ttggccatgc tccagctgac aacaggagga     300
gaaacccagc agcagattca agcagctatg ggattcaaga ttgatgacaa gggcatggcc     360
ccgcccctcc ggcatctgta caaggagctc atggggccat ggaacaagga tgagatcagc     420
accacagacg cgatcttcgt ccagcgggat ctgaagctgg tccagggctt catgccccac     480
ttcttcaggc tgttccggag cacggtcaag caagtggact tttcagaggt ggagagagcc     540
agattcatca tcaatgactg ggtgaagaca cacacaaaag gtatgatcag caacttgctt     600
gggaaaggag ccgtggacca gctgacacgg ctggtgctgg tgaatgccct ctacttcaac     660
ggccagtgga agactccctt ccccgactcc agcacccacc gccgcctctt ccacaaatca     720
gacggcagca ctgtctctgt gcccatgatg gctcagacca caagttcaa ctatactgag     780
ttcaccacgc ccgatggcca ttactacgac atcctggaac tgcctacca cggggacacc     840
ctcagcatgt tcattgctgc cccttatgaa aagaggtgc ctctctctgc cctcaccaac     900
attctgagtg cccagctcat cagccactgg aaaggcaaca tgaccaggct gccccgcctc     960
ctggttctgc ccaagttctc cctggagact gaagtcgacc tcaggaagcc cctagagaac    1020
ctgggaatga ccgacatgtt cagacagttt caggctgact tcacgagtct ttcagaccaa    1080
gagcctctcc acgtcgcgca ggcgctgcag aaagtgaaga tcgaggtgaa cgagagtggc    1140
acggtggcct cctcatccac agctgtcata gtctcagccc gcatggcccc cgaggagatc    1200
atcatggaca gaccccttcc tctttgtggtc cggcacaacc ccacaggaac agtccttttc    1260
atgggccaag tgatggaacc ctgaccctgg ggaaagacgc cttcatctgg acaaaactg     1320
gagatgcatc gggaaagaag aaactccgaa gaaaagaatt ttagtgttaa tgactctttc    1380
tgaaggaaga aagacatttt gccttttgtt aaaagatggt aaaccagatc tgtctccaag    1440
accttggcct ctccttggag gacctttagg tcaaactccc tagtctccac ctgagaccct    1500
gggagagaag tttgaagcac aactccctta aggtctccaa accagacggt gacgcctgcg    1560
ggaccatctg ggcacctgc ttccacccgt ctctctgccc actcgggtct gcagacctgg    1620
ttcccactga ggccctttgc aggatggaac tacggggctt acaggagctt tgtgtgcct     1680
ggtagaaact atttctgttc cagtcacatt gccatcactc ttgtactgcc tgccaccgcg    1740
gaggaggctg tgacaggcc aaaggccagt ggaagaaaca cctttcatc tcagagtcca    1800
ctgtggcact ggccacccct ccccagtaca ggggtgctgc aggtggcaga gtgaatgtcc    1860
cccatcatgt ggcccaactc tcctggcctg gccatctccc tccccagaaa cagtgtgcat    1920
gggttatttt ggagtgtagg tgacttgttt actcattgaa gcagatttct gcttcctttt    1980
```

-continued

```
attttttatag gaatagagga agaaatgtca gatgcgtgcc cagctcttca cccccccaatc    2040 tcttggtggg gaggggtgta cctaaatatt tatcatatcc ttgcccttga gtgcttgtta    2100
gagagaaaga gaactactaa ggaaaataat attatttaaa ctcgctccta gtgtttcttt    2160
gtggtctgtg tcaccgtatc tcaggaagtc cagccacttg actggcacac accccctccgg    2220 acatccagcg tgacggagcc cacactgcca ccttgtggcc gcctgagacc ctcgcgcccc    2280
ccgcgccccc cgcgccccctc ttttttccccct tgatggaaat tgaccataca atttcatcct    2340
ccttcagggg atcaaaagga cggagtgggg ggacagagac tcagatgagg acagagtggt    2400
ttccaatgtg ttcaatagat ttaggagcag aaatgcaagg ggctgcatga cctaccagga    2460
cagaactttc cccaattaca gggtgactca cagccgcatt ggtgactcac ttcaatgtgt    2520
catttccggc tgctgtgtgt gagcagtgga cacgtgaggg gggggtgggt gagagagaca    2580
ggcagctcgg attcaactac cttagataat atttctgaaa acctaccagc cagagggtag    2640
ggcacaaaga tggatgtaat gcactttggg aggccaaggc gggaggattg cttgagccca    2700
ggagttcaag accagcctgg gcaacatacc aagaccccccg tctctttaaa aatatatata    2760
ttttaaatat acttaaatat atatttctaa tatctttaaa tatatatata tattttaaag    2820
accaatttat gggagaattg cacacagatg tgaaatgaat gtaatctaat agaagc    2876
```

<210> SEQ ID NO 23
<211> LENGTH: 390
<212> TYPE: PRT
<213> ORGANISM: Homo sapiens

<400> SEQUENCE: 23

```
Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220
```

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
        260                 265                 270

Ser Ser Arg His Arg Arg Ala Leu Asp Thr Asn Tyr Cys Phe Ser Ser
    275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 24
<211> LENGTH: 2583
<212> TYPE: DNA
<213> ORGANISM: Homo sapiens

<400> SEQUENCE: 24
agccggtccc cgccgccgcc gcccttcgcg ccctgggcca tctccctccc acctccctcc      60
gcggagcagc cagacagcga gggccccggc cggggcaggg gggacgccc cgtccggggc      120 accccccgg ctctgagccg cccgcgggc cggcctcggc ccggagcgga ggaaggagtc      180
gccgaggagc agcctgaggc cccagagtct gagacgagcc gccgccgccc cgccactgc      240 ggggaggagg gggaggagga gcgggaggag ggacgagctg gtcgggagaa gaggaaaaaa      300
acttttgaga cttttccgtt gccgctggga gccggaggcg cggggacctc ttggcgcgac      360
gctgccccgc gaggaggcag gacttgggga ccccagaccg cctcccttg ccgccggga      420 cgcttgctcc ctccctgccc cctacacggc gtccctcagg cgcccccatt ccggaccagc      480
cctcgggagt cgccgacccg gcctcccgca aagactttc cccagacctc gggcgcaccc      540
cctgcacgcc gccttcatcc ccggcctgtc tcctgagccc ccgcgcatcc tagacccttt      600
ctcctccagg agacggatct ctctccgacc tgccacagat ccctattca agaccaccca      660 ccttctggta ccagatcgcg cccatctagg ttatttccgt gggatactga dacacccccg      720
gtccaagcct cccctccacc actgcgccct tctccctgag acctcagct ttccctcgag      780 gccctcctac cttttgccgg gagaccccca gccctgcag gggcggggcc tccccaccac      840
accagccctg ttcgcgctct cggcagtgcc gggggggcgcc gcctcccca tgccgccctc      900 cgggctgcgg ctgctgccgc tgctgctacc gctgctgtgg ctactggtgc tgacgcctgg      960
ccggccggcc gcgggactat ccacctgcaa gactatcgac atggagctgg tgaagcggaa      1020
gcgcatcgag gccatccgcg gccagatcct gtccaagctg cggctcgcca gcccccgag      1080 ccagggggag gtgccgcccg gccgctgccc cgaggccgtg ctcgccctgt acaacagcac      1140

```
ccgcgaccgg gtggccgggg agagtgcaga accggagccc gagcctgagg ccgactacta    1200
cgccaaggag gtcacccgcg tgctaatggt ggaaacccac aacgaaatct atgacaagtt    1260
caagcagagt acacacagca tatatatgtt cttcaacaca tcagagctcc gagaagcggt    1320
acctgaaccc gtgttgctct cccgggcaga gctgcgtctg ctgaggctca agttaaaagt    1380
ggagcagcac gtggagctgt accagaaata cagcaacaat tcctggcgat acctcagcaa    1440
ccggctgctg gcacccagcg actcgccaga gtggttatct tttgatgtca ccggagttgt    1500
gcggcagtgg ttgagccgtg aggggaaat tgagggcttt cgccttagcg cccactgctc     1560
ctgtgacagc agggataaca cactgcaagt ggacatcaac gggttcacta ccggccgccg    1620
aggtgacctg gccaccattc atggcatgaa ccggcctttc ctgcttctca tggccacccc    1680
gctggagagg gcccagcatc tgcaaagctc ccggcaccgc cgagccctgg acaccaacta    1740
ttgcttcagc tccacggaga agaactgctg cgtgcggcag ctgtacattg acttccgcaa    1800
ggacctcggc tggaagtgga tccacgagcc caagggctac catgccaact tctgcctcgg    1860
gccctgcccc tacatttgga gcctggacac gcagtacagc aaggtcctgg ccctgtacaa    1920
ccagcataac ccgggcgcct cggcggcgcc gtgctgcgtg ccgcaggcgc tggagccgct    1980
gcccatcgtg tactacgtgg gccgcaagcc caaggtggag cagctgtcca acatgatcgt    2040
gcgctcctgc aagtgcagct gaggtcccgc ccgccccgc ccgcccggg caggcccggc      2100 cccaccccgc ccgcccccg ctgccttgcc catgggggct gtatttaagg cacccgtgc      2160 cccaagccca cctggggccc cattaaagat ggagagagga ctgcggatct ctgtgtcatt    2220
gggcgcctgc ctggggtctc catccctgac gttccccac tcccactccc tctctctccc    2280
tctctgcctc ctcctgcctg tctgcactat tcctttgccc ggcatcaagg cacaggggac    2340
cagtggggaa cactactgta gttagatcta tttattgagc accttgggca ctgttgaagt    2400
gccttacatt aatgaactca ttcagtcacc atagcaacac tctgagatgc agggactctg    2460
ataacaccca ttttaaaggt gaggaaacaa gcccagagag gttaagggag gagttcctgc    2520
ccaccaggaa cctgctttag tgggggatag tgaagaagac aataaaagat agtagttcag    2580
gcc                                                                   2583

<210> SEQ ID NO 25
<211> LENGTH: 22
<212> TYPE: RNA
<213> ORGANISM: Homo sapiens

<400> SEQUENCE: 25
uagcuuauca gacugauguu ga                                             22

<210> SEQ ID NO 26
<211> LENGTH: 21
<212> TYPE: RNA
<213> ORGANISM: Homo sapiens

<400> SEQUENCE: 26
ugagaugaag cacuguagcu c                                              21

<210> SEQ ID NO 27
<211> LENGTH: 22
<212> TYPE: RNA
<213> ORGANISM: Homo sapiens

<400> SEQUENCE: 27
```

-continued

```
uagcaccauu ugaaaucggu ua                                                    22

<210> SEQ ID NO 28
<211> LENGTH: 23
<212> TYPE: RNA
<213> ORGANISM: Homo sapiens

<400> SEQUENCE: 28
uuaaugcuaa ucgugauagg ggu                                                   23

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Arg Gly Asp Ser His
1               5

<210> SEQ ID NO 30
<211> LENGTH: 10
<212> TYPE: PRT
<213> ORGANISM: Unknown
<220> FEATURE:
<223> OTHER INFORMATION: Description of Unknown:
      Laminin peptide

<400> SEQUENCE: 30

Arg Asn Ile Ala Glu Ile Ile Lys Asp Ile
1               5                   10

<210> SEQ ID NO 31
<211> LENGTH: 16
<212> TYPE: PRT
<213> ORGANISM: Unknown
<220> FEATURE:
<223> OTHER INFORMATION: Description of Unknown:
      Immobilized ligand peptide
<220> FEATURE:
<223> OTHER INFORMATION: N-term Ac

<400> SEQUENCE: 31

Gly Cys Arg Asp Gly Pro Gln Gly Ile Trp Gly Gln Asp Arg Cys Gly
1               5                   10                  15

<210> SEQ ID NO 32
<211> LENGTH: 2386
<212> TYPE: PRT
<213> ORGANISM: Homo sapiens

<400> SEQUENCE: 32

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80
```

```
Gly Ser Arg Gly Phe Asn Cys Glu Ser Lys Pro Glu Ala Glu Thr
                85                  90                  95
Cys Phe Asp Lys Tyr Thr Gly Asn Thr Tyr Arg Val Gly Asp Thr Tyr
            100                 105                 110
Glu Arg Pro Lys Asp Ser Met Ile Trp Asp Cys Thr Cys Ile Gly Ala
        115                 120                 125
Gly Arg Gly Arg Ile Ser Cys Thr Ile Ala Asn Arg Cys His Glu Gly
    130                 135                 140
Gly Gln Ser Tyr Lys Ile Gly Asp Thr Trp Arg Pro His Glu Thr
145                 150                 155                 160
Gly Gly Tyr Met Leu Glu Cys Val Cys Leu Gly Asn Gly Lys Gly Glu
            165                 170                 175
Trp Thr Cys Lys Pro Ile Ala Glu Lys Cys Phe Asp His Ala Ala Gly
        180                 185                 190
Thr Ser Tyr Val Val Gly Glu Thr Trp Glu Lys Pro Tyr Gln Gly Trp
    195                 200                 205
Met Met Val Asp Cys Thr Cys Leu Gly Glu Gly Ser Gly Arg Ile Thr
    210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
            245                 250                 255
Gln Cys Ile Cys Thr Gly Asn Gly Arg Gly Glu Trp Lys Cys Glu Arg
        260                 265                 270
His Thr Ser Val Gln Thr Thr Ser Ser Gly Ser Gly Pro Phe Thr Asp
    275                 280                 285
Val Arg Ala Ala Val Tyr Gln Pro Gln Pro His Pro Gln Pro Pro Pro
    290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
            325                 330                 335
Gly Asn Gly Val Ser Cys Gln Glu Thr Ala Val Thr Gln Thr Tyr Gly
        340                 345                 350
Gly Asn Ser Asn Gly Glu Pro Cys Val Leu Pro Phe Thr Tyr Asn Gly
    355                 360                 365
Arg Thr Phe Tyr Ser Cys Thr Thr Glu Gly Arg Gln Asp Gly His Leu
    370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
            405                 410                 415
Gly Ala Leu Cys His Phe Pro Phe Leu Tyr Asn Asn His Asn Tyr Thr
        420                 425                 430
Asp Cys Thr Ser Glu Gly Arg Arg Asp Asn Met Lys Trp Cys Gly Thr
    435                 440                 445
Thr Gln Asn Tyr Asp Ala Asp Gln Lys Phe Gly Phe Cys Pro Met Ala
    450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
            485                 490                 495
Thr Cys Val Gly Asn Gly Arg Gly Glu Trp Thr Cys Ile Ala Tyr Ser
```

-continued

```
                500             505             510
Gln Leu Arg Asp Gln Cys Ile Val Asp Asp Ile Thr Tyr Asn Val Asn
            515                 520                 525
Asp Thr Phe His Lys Arg His Glu Glu Gly His Met Leu Asn Cys Thr
            530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
            595                 600                 605
Ser Gly Pro Val Glu Val Phe Ile Thr Glu Thr Pro Ser Gln Pro Asn
            610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
            675                 680                 685
His Gln Glu Val Thr Arg Phe Asp Phe Thr Thr Thr Ser Thr Ser Thr
            690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
                740                 745                 750
Glu Tyr Glu Leu Ser Glu Glu Gly Asp Glu Pro Gln Tyr Leu Asp Leu
            755                 760                 765
Pro Ser Thr Ala Thr Ser Val Asn Ile Pro Asp Leu Leu Pro Gly Arg
            770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Thr Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
            835                 840                 845
Val Glu Gly Ser Ser Thr Glu Leu Asn Leu Pro Glu Thr Ala Asn Ser
            850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
            915                 920                 925
```

```
Pro Pro Glu Ser Ala Val Thr Gly Tyr Arg Val Asp Val Ile Pro Val
    930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
                980                 985                 990
Gln Thr Thr Lys Leu Asp Ala Pro Thr Asn Leu Gln Phe Val Asn Glu
        995                 1000                1005
Thr Asp Ser Thr Val Leu Val Arg Trp Thr Pro Pro Arg Ala Gln
    1010                1015                1020
Ile Thr Gly Tyr Arg Leu Thr Val Gly Leu Thr Arg Arg Gly Gln
    1025                1030                1035
Pro Arg Gln Tyr Asn Val Gly Pro Ser Val Ser Lys Tyr Pro Leu
    1040                1045                1050
Arg Asn Leu Gln Pro Ala Ser Glu Tyr Thr Val Ser Leu Val Ala
    1055                1060                1065
Ile Lys Gly Asn Gln Glu Ser Pro Lys Ala Thr Gly Val Phe Thr
    1070                1075                1080
Thr Leu Gln Pro Gly Ser Ser Ile Pro Pro Tyr Asn Thr Glu Val
    1085                1090                1095
Thr Glu Thr Thr Ile Val Ile Thr Trp Thr Pro Ala Pro Arg Ile
    1100                1105                1110
Gly Phe Lys Leu Gly Val Arg Pro Ser Gln Gly Gly Glu Ala Pro
    1115                1120                1125
Arg Glu Val Thr Ser Asp Ser Gly Ser Ile Val Val Ser Gly Leu
    1130                1135                1140
Thr Pro Gly Val Glu Tyr Val Tyr Thr Ile Gln Val Leu Arg Asp
    1145                1150                1155
Gly Gln Glu Arg Asp Ala Pro Ile Val Asn Lys Val Val Thr Pro
    1160                1165                1170
Leu Ser Pro Pro Thr Asn Leu His Leu Glu Ala Asn Pro Asp Thr
    1175                1180                1185
Gly Val Leu Thr Val Ser Trp Glu Arg Ser Thr Thr Pro Asp Ile
    1190                1195                1200
Thr Gly Tyr Arg Ile Thr Thr Thr Pro Thr Asn Gly Gln Gln Gly
    1205                1210                1215
Asn Ser Leu Glu Glu Val Val His Ala Asp Gln Ser Ser Cys Thr
    1220                1225                1230
Phe Asp Asn Leu Ser Pro Gly Leu Glu Tyr Asn Val Ser Val Tyr
    1235                1240                1245
Thr Val Lys Asp Asp Lys Glu Ser Val Pro Ile Ser Asp Thr Ile
    1250                1255                1260
Ile Pro Ala Val Pro Pro Pro Thr Asp Leu Arg Phe Thr Asn Ile
    1265                1270                1275
Gly Pro Asp Thr Met Arg Val Thr Trp Ala Pro Pro Pro Ser Ile
    1280                1285                1290
Asp Leu Thr Asn Phe Leu Val Arg Tyr Ser Pro Val Lys Asn Glu
    1295                1300                1305
Glu Asp Val Ala Glu Leu Ser Ile Ser Pro Ser Asp Asn Ala Val
    1310                1315                1320
```

```
Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635

Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
    1685                1690                1695

Thr Val Ser Val Val Ala Leu His Asp Asp Met Glu Ser Gln Pro
    1700                1705                1710

Leu Ile Gly Thr Gln Ser Thr Ala Ile Pro Ala Pro Thr Asp Leu
```

```
            1715                1720                1725

Lys Phe Thr Gln Val Thr Pro Thr Ser Leu Ser Ala Gln Trp Thr
            1730                1735                1740

Pro Pro Asn Val Gln Leu Thr Gly Tyr Arg Val Arg Val Thr Pro
            1745                1750                1755

Lys Glu Lys Thr Gly Pro Met Lys Glu Ile Asn Leu Ala Pro Asp
            1760                1765                1770

Ser Ser Ser Val Val Val Ser Gly Leu Met Val Ala Thr Lys Tyr
            1775                1780                1785

Glu Val Ser Val Tyr Ala Leu Lys Asp Thr Leu Thr Ser Arg Pro
            1790                1795                1800

Ala Gln Gly Val Val Thr Thr Leu Glu Asn Val Ser Pro Pro Arg
            1805                1810                1815

Arg Ala Arg Val Thr Asp Ala Thr Glu Thr Thr Ile Thr Ile Ser
            1820                1825                1830

Trp Arg Thr Lys Thr Glu Thr Ile Thr Gly Phe Gln Val Asp Ala
            1835                1840                1845

Val Pro Ala Asn Gly Gln Thr Pro Ile Gln Arg Thr Ile Lys Pro
            1850                1855                1860

Asp Val Arg Ser Tyr Thr Ile Thr Gly Leu Gln Pro Gly Thr Asp
            1865                1870                1875

Tyr Lys Ile Tyr Leu Tyr Thr Leu Asn Asp Asn Ala Arg Ser Ser
            1880                1885                1890

Pro Val Val Ile Asp Ala Ser Thr Ala Ile Asp Ala Pro Ser Asn
            1895                1900                1905

Leu Arg Phe Leu Ala Thr Thr Pro Asn Ser Leu Leu Val Ser Trp
            1910                1915                1920

Gln Pro Pro Arg Ala Arg Ile Thr Gly Tyr Ile Ile Lys Tyr Glu
            1925                1930                1935

Lys Pro Gly Ser Pro Pro Arg Glu Val Val Pro Arg Pro Arg Pro
            1940                1945                1950

Gly Val Thr Glu Ala Thr Ile Thr Gly Leu Glu Pro Gly Thr Glu
            1955                1960                1965

Tyr Thr Ile Tyr Val Ile Ala Leu Lys Asn Asn Gln Lys Ser Glu
            1970                1975                1980

Pro Leu Ile Gly Arg Lys Lys Thr Asp Glu Leu Pro Gln Leu Val
            1985                1990                1995

Thr Leu Pro His Pro Asn Leu His Gly Pro Glu Ile Leu Asp Val
            2000                2005                2010

Pro Ser Thr Val Gln Lys Thr Pro Phe Val Thr His Pro Gly Tyr
            2015                2020                2025

Asp Thr Gly Asn Gly Ile Gln Leu Pro Gly Thr Ser Gly Gln Gln
            2030                2035                2040

Pro Ser Val Gly Gln Gln Met Ile Phe Glu Glu His Gly Phe Arg
            2045                2050                2055

Arg Thr Thr Pro Pro Thr Thr Ala Thr Pro Ile Arg His Arg Pro
            2060                2065                2070

Arg Pro Tyr Pro Pro Asn Val Gly Glu Glu Ile Gln Ile Gly His
            2075                2080                2085

Ile Pro Arg Glu Asp Val Asp Tyr His Leu Tyr Pro His Gly Pro
            2090                2095                2100

Gly Leu Asn Pro Asn Ala Ser Thr Gly Gln Glu Ala Leu Ser Gln
            2105                2110                2115
```

-continued

```
Thr Thr Ile Ser Trp Ala Pro Phe Gln Asp Thr Ser Glu Tyr Ile
    2120                2125            2130

Ile Ser Cys His Pro Val Gly Thr Asp Glu Glu Pro Leu Gln Phe
    2135                2140            2145

Arg Val Pro Gly Thr Ser Thr Ser Ala Thr Leu Thr Gly Leu Thr
    2150                2155            2160

Arg Gly Ala Thr Tyr Asn Val Ile Val Glu Ala Leu Lys Asp Gln
    2165                2170            2175

Gln Arg His Lys Val Arg Glu Glu Val Val Thr Val Gly Asn Ser
    2180                2185            2190

Val Asn Glu Gly Leu Asn Gln Pro Thr Asp Asp Ser Cys Phe Asp
    2195                2200            2205

Pro Tyr Thr Val Ser His Tyr Ala Val Gly Asp Glu Trp Glu Arg
    2210                2215            2220

Met Ser Glu Ser Gly Phe Lys Leu Leu Cys Gln Cys Leu Gly Phe
    2225                2230            2235

Gly Ser Gly His Phe Arg Cys Asp Ser Ser Arg Trp Cys His Asp
    2240                2245            2250

Asn Gly Val Asn Tyr Lys Ile Gly Glu Lys Trp Asp Arg Gln Gly
    2255                2260            2265

Glu Asn Gly Gln Met Met Ser Cys Thr Cys Leu Gly Asn Gly Lys
    2270                2275            2280

Gly Glu Phe Lys Cys Asp Pro His Glu Ala Thr Cys Tyr Asp Asp
    2285                2290            2295

Gly Lys Thr Tyr His Val Gly Glu Gln Trp Gln Lys Glu Tyr Leu
    2300                2305            2310

Gly Ala Ile Cys Ser Cys Thr Cys Phe Gly Gly Gln Arg Gly Trp
    2315                2320            2325

Arg Cys Asp Asn Cys Arg Arg Pro Gly Gly Glu Pro Ser Pro Glu
    2330                2335            2340

Gly Thr Thr Gly Gln Ser Tyr Asn Gln Tyr Ser Gln Arg Tyr His
    2345                2350            2355

Gln Arg Thr Asn Thr Asn Val Asn Cys Pro Ile Glu Cys Phe Met
    2360                2365            2370

Pro Leu Asp Val Gln Ala Asp Arg Glu Asp Ser Arg Glu
    2375                2380            2385
```